(12) United States Patent
Wu et al.

(10) Patent No.: US 10,537,594 B2
(45) Date of Patent: Jan. 21, 2020

(54) TARGETED TRANSPLANTATION OF MITOCHONDRIA TO HEPATOCYTES

(71) Applicant: University of Connecticut, Farmington, CT (US)

(72) Inventors: George Y Wu, Avon, CT (US); Catherine H Wu, Avon, CT (US); Nidhi Gupta, Mountain View, CA (US)

(73) Assignee: University of Connecticut, Farmington, CT (US)

( * ) Notice: Subject to any disclaimer, the term of this patent is extended or adjusted under 35 U.S.C. 154(b) by 97 days.

(21) Appl. No.: 15/553,717

(22) PCT Filed: Feb. 26, 2016

(86) PCT No.: PCT/US2016/019845
§ 371 (c)(1),
(2) Date: Aug. 25, 2017

(87) PCT Pub. No.: WO2016/138420
PCT Pub. Date: Sep. 1, 2016

(65) Prior Publication Data
US 2018/0036344 A1 Feb. 8, 2018

Related U.S. Application Data

(60) Provisional application No. 62/126,068, filed on Feb. 27, 2015.

(51) Int. Cl.
*A61K 35/12* (2015.01)
*A61K 47/64* (2017.01)
*C12N 5/12* (2006.01)

(52) U.S. Cl.
CPC ............. *A61K 35/12* (2013.01); *A61K 47/64* (2017.08); *A61K 47/6455* (2017.08); *C12N 5/12* (2013.01)

(58) Field of Classification Search
CPC .......... C12N 15/80; C12N 15/52; C12N 5/12; A61K 35/12; A61K 38/1709; A61K 47/64; A61K 47/6455
See application file for complete search history.

(56) References Cited

U.S. PATENT DOCUMENTS

| | | | | |
|---|---|---|---|---|
| 5,166,320 A * | 11/1992 | Wu | ........................ | A61K 47/62 424/537 |
| 2013/0149778 A1* | 6/2013 | Chang | ................ | A61K 49/0097 435/366 |
| 2014/0193511 A1 | 7/2014 | Yivgi-Ohana et al. | | |

OTHER PUBLICATIONS

Su Dani, The challenge of vector development in gene therapy, Vector development in gene therapy Brazilian Journal of Medical and Biological Research (1999) 32: 133-145.*

Web Md, Liver diseases: Types of liver problems and their causes, accessed online Apr. 11, 2019.*
Ashwell, et al., "The role of surface carbohydrates in the hepatic recognition and transport of circulating glycoproteins," Advances in enzymology and related subjects, pp. 99-128, 1974.
Beauregard, et al., pH-dependent Perforation of Macrophage Phagosomes by Listeriolysin O from Listeria monocytogenes, J Exp Med, pp. 186-1159, 1997.
Benbrik, et al., "Cellular and mitochondrial toxicity of zidovudine (AZT), didanosine (ddI) and zalcitabine (ddC) on cultured human muscle cells," Journal of Neurological Sciences, vol. 149, 19-25, 1997.
Chariot, et al., "Zidovudine-induced mitochondrial disorder with massive liver seteatosis, myopathy, lactic acidosis, and mitochondrial DNA depletion," Journal of Hepatology, vol. 30, pp. 156-160, 1999.
Choi, et al., "Reactive Oxygen Species Suppress Hepatitis C Virus RNA Replicatio in human Hepatoma Cells," Hepatology, vol. 39, No. 1, pp. 81-89, 2004.
Costabile, et al., Measuring the 50% Haemolytic Complement (CH50) Activity of Serum, Journal of Visualized Experiments, 3 pages, 2010.
Hashinguchi, et al., "Espablishment of Human Cell Lines Lacking Mictochondrial DNA," Methods Mol Biol, pp. 383-391, 2009.
Jacobs, et al., "Listeriolysin O: cholesterol inhibits cytolysis but not binding to cellular membranes," Molecular Microbiology, vol. 28, No. 6, pp. 1081-1089, 1998.
Labbe, et al., "Drug-induced liver injury through mitochondrial dysfunction; mechanisms and detection during preclinical safety studies," Fundamental & Clinical Pharmacology, vol. 22, pp. 335-353, 2008.
Piasek, et al., "Effects of Colchicine on Endocytosis and Cellular Inactivation of Horseradish Peroxidase inCultured Chondrocytes," The Journal of Cell Biology, vol. 81, No. 2, pp. 426-437, 1979.
Untergasser, et al., "Primer3—new capabilities and interfaces," Nucleic Acids Research, vol. 40, No. 15, 12 pages, 2012.
Walton, et al., "A Method for Purification of Listeriolysin O from a Hypersecretor Strain of Listeria monocytogenes," Protein Expression and Purification, vol. 15, pp. 243-245, 1999.
Whitehead, et al., "A simple technique for the isolation of orosomucoid from normal and pathological sera," Biochimica et biophysica acta, vol. 124, pp. 209-211, 1966.
Ye, et al., "Primer-BLAST: A tool to design target-specific primers for polymerase chain reaction," BMC Bioinformatics, vol. 13, No. 134, 11 pages, 2012.
International Search Report for PCT/US2016/019845, dated Jul. 20, 2016.

* cited by examiner

*Primary Examiner* — Rachael E Bredefeld
*Assistant Examiner* — Erinne R Dabkowski
(74) *Attorney, Agent, or Firm* — McDonnell Boehnen Hulbert & Berghoff LLP

(57) ABSTRACT

The present disclosure relates to, inter alia, compositions and kits comprising an asialoglycoprotein covalently attached to a polycation, and functional mammalian mitochondria that are at least partially purified and are electrostatically bound to the AsG-polycation molecule; as well as methods of their preparation and use.

22 Claims, 30 Drawing Sheets
Specification includes a Sequence Listing.

SEQUENCE LISTING

```
<160> NUMBER OF SEQ ID NOS: 4

<210> SEQ ID NO 1
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1
taatgaagga cttggcagat gaact                                        25

<210> SEQ ID NO 2
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 2
acggctttct ccctcttgct                                              20

<210> SEQ ID NO 3
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 3
aggcttaaaa gcagccatca                                              20

<210> SEQ ID NO 4
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 4
gacaatggtt atccgggttg                                              20
```

US 10,537,594 B2

TARGETED TRANSPLANTATION OF MITOCHONDRIA TO HEPATOCYTES

INCORPORATION OF SEQUENCE LISTING

The instant application contains a Sequence Listing, which has been submitted electronically in ASCII format and is hereby incorporated by reference in its entirety. Said ASCII copy, created on Feb. 24, 2016, is named 1900-422_SL.txt and is 1,323 bytes in size.

TECHNICAL FIELD

This invention relates to the field of diseases and conditions that can benefit from increased intracellular mitochondrial function.

BACKGROUND

Mitochondria are membrane-limited subcellular organelles that contain their own DNA and metabolic systems; they function as the powerhouses of mammalian cells. Organs that are most metabolically active have the highest need for energy, and also have the highest number of mitochondria per cell.

Genetic and acquired mitochondrial defects that results in dysfunction cause disease and frequently early death due to liver damage. Genetic defects are rare; but are usually fatal early in life. Acquired mitochondrial damage due to drug toxicity, however, is relatively common, and can lead to severe morbidity and death in adults. There are currently no cures for mitochondrial defects or damage.

SUMMARY

This disclosure provides a composition (such as a pharmaceutical composition) comprising: an asialoglycoprotein (AsG) covalently attached to a polycation, and functional mammalian mitochondria that are at least partially purified and are electrostatically bound to the AsG-polycation. In certain embodiments, the composition further comprises an endosomolytic agent that is covalently attached to an AsG by a cleavable bond.

In other aspects, this disclosure provides a method of making a pharmaceutical composition to treat or prevent a disease or condition that can benefit from increased cellular mitochondrial function, such as liver disease, comprising: at least partially purifying functional mammalian mitochondria from a cell; allowing an AsG to be covalently attached to a highly positively charged polycation; and allowing the AsG/polycation molecule to bind electrostatically with the mitochondria. In certain embodiments, the method further comprises providing an endosomolytic agent; in further embodiments, the endosomolytic agent is covalently attached to an AsG; and in yet further embodiments, the endosomolytic agent is covalently attached to an AsG by a cleavable bond.

In other aspects, this disclosure provides a method of transplanting mitochondria into a hepatocyte, comprising providing a pharmaceutical composition comprising functional mammalian mitochondria complexed with AsG-PL electrostatically; and delivering said composition to a hepatocyte. In certain embodiments, the composition further comprises an endosomolytic agent covalently attached to an AsG by a cleavable bond.

In certain aspects, this disclosure provides a kit comprising a pharmaceutical composition that comprises an asialoglycoprotein (AsG) covalently attached to a polycation; at least partially purified, functional mammalian mitochondria, electrostatically bound to the AsG/polycation; and instruction for using said composition to treat or prevent a disease or condition that can benefit from increased cellular mitochondrial function, such as liver disease.

In certain other aspects, a method is provided to treat or prevent a disease or condition that can benefit from increased cellular mitochondrial function, such as liver disease, comprising administering a therapeutically effective amount of a pharmaceutical composition disclosed herein to a patient in need thereof.

Numerous other aspects are provided in accordance with these and other aspects of the invention. Other features and aspects of the present invention will become more fully apparent from the following detailed description and the appended claims.

BRIEF DESCRIPTION OF THE DRAWINGS

Several drawings have been converted from color to black and white.

FIG. 7. Formation and stability of an asialoglycoprotein-polylysine (AsOR-PL) conjugate-mitochondrial complexes. Freshly isolated rat mitochondria were incubated with Fl-AsOR-PL or AsOR-PL, and repeatedly centrifuged and re-suspended in fresh medium.

FIG. 16A, endosomal marker; FIG. 16B, GFP.

FIG. 17C, DAPI nuclei, and FIG. 17D merged.

FIG. 18A, EEA1-Alexa 594 endosomal marker; FIG. 18B, GFP; FIG. 18C, DAPI nuclei, and FIG. 18D merged.

FIG. 19A, endosomal marker (anti-EEA1-Alexa Fluor 594); FIG. 19B, GFP.

FIG. 20B, merged.

FIG. 23. Co-administration of complexed mitochondria and controls in Huh 7-Mito (−) and SK Hep1-Mito (−) cells as measured by fluorescence and qPCR. Cells were incubated separately with media alone, mitochondria alone, Fl-AsOR-PL-mitochondria complex, complexed mitochondria plus AsOR-LLO, complexed mitochondria plus excess AsOR or complexed mitochondria plus AsOR-LLO plus excess AsOR at 37° C. for 2 h and maintained in supplement-free cell culture media. FIG. 23B, 10 d; FIG. 23D, 4 d. Mitochondrial DNA levels in FIG. 23E, Huh 7-Mito (−) cells at 10 d.

FIG. 25. Effects of transplanted Huh 7 mitochondria on cellular DNA levels in Mito (−) cells.

FIG. 26. Characterization of mitochondrial respiration. Cells were plated in XF24 cell culture microplates 1 day before mitochondria respiration measurements. Oxygen consumption rates (OCR) were measured with a Seahorse XFe Analyzer to determine mitochondrial respiration in FIG. 26A, Huh 7-Mito (−), SK Hep1-Mito (−) cells, and parental Huh 7 and SK Hep1 cells. OCR was measured after sequential addition of oligomycin, carbonyl cyanide-p-trifluoromethoxyphenyl-hydrazone (FCCP) or rotenone to evaluate mitochondrial respiration in cells. Oxygen consumption rates and effects of inhibitors of mitochondrial respiration in Huh 7-Mito (−) cells after co-administration of complexed mitochondria or controls FIG. 26B, 12 h; and FIG. 26C, 10 d.

DETAILED DESCRIPTION

As used herein, the word "a" or "plurality" before a noun represents one or more of the particular noun. For example, the phrase "a mammalian cell" represents "one or more mammalian cells."

The term "mammalian cell" is known in the art and can refer to any cell from or derived from any mammal including, for example, a human, a hamster, a mouse, a green monkey, a rat, a pig, a cow, a hamster, or a rabbit. In some embodiments, the mammalian cell can be an immortalized cell, a differentiated cell, an undifferentiated cell, a stem cell, etc.

As used herein, the terms "subject" and "patient" are used interchangeably. A patient or a subject can be a human patient or a human subject.

For the terms "for example" and "such as," and grammatical equivalences thereof, the phrase "and without limitation" is understood to follow unless explicitly stated otherwise. As used herein, the term "about" is meant to account for variations due to experimental error. All measurements reported herein are understood to be modified by the term "about," whether or not the term is explicitly used, unless explicitly stated otherwise. As used herein, the singular forms "a," "an," and "the" include plural referents unless the context clearly dictates otherwise.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Figure 1:
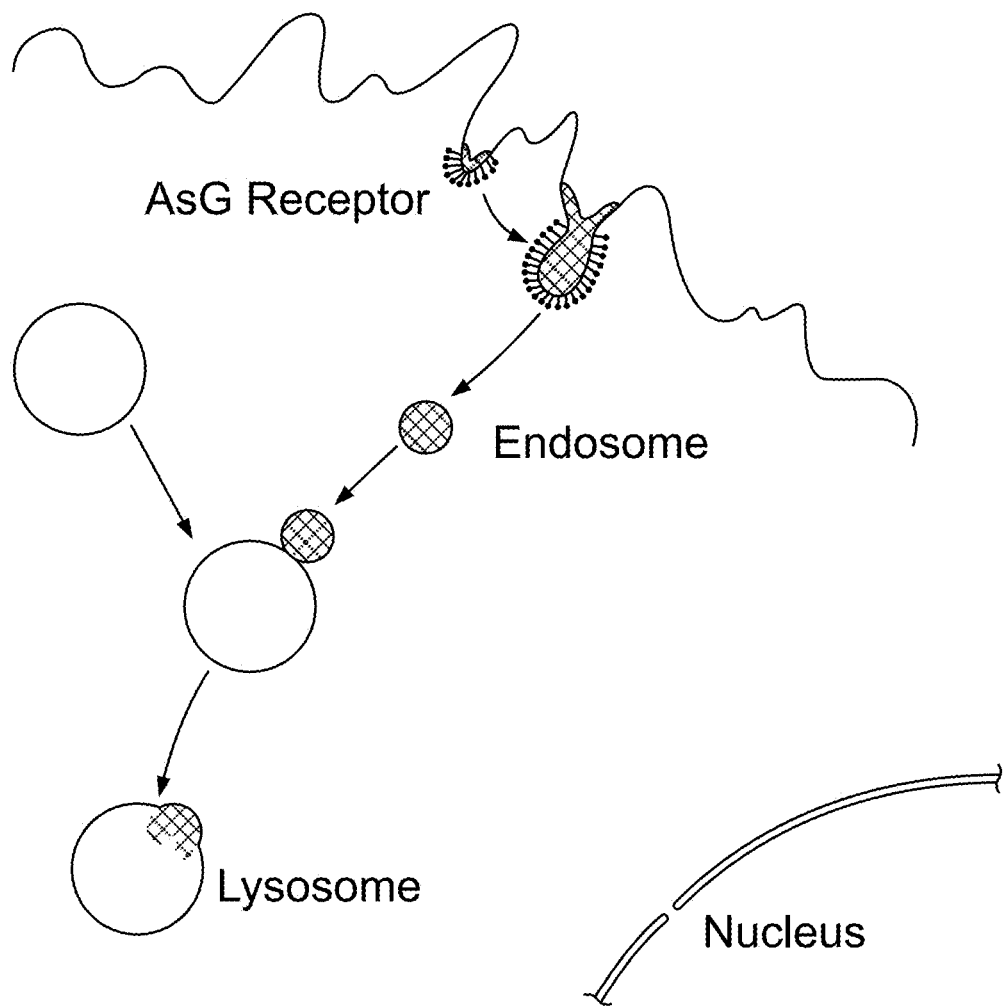
FIG. 1. A diagram of receptor-mediated endocytosis of asialoglycoproteins (AsG) by the asialoglycoprotein receptor.

Liver cells (hepatocytes) have unique cell surface receptors that recognize and bind proteins known as asialoglycoproteins (AsG), which have exposed galactose residues. Binding of AsG to its receptor triggers an invagination of the cell surface membrane and eventually isolating the receptor-glycoprotein complex in an intracellular membrane-limited vesicle, an endosome. Endosomes fuse with lysosomes containing degradative enzymes, resulting in breakdown of the glycoprotein. The asialoglycoprotein receptor system represents a natural mechanism by which substances outside cells can gain access to the interior of cells, See, e.g., FIG. 1.

Mammalian hepatocytes are highly differentiated cells. But unlike most differentiated cells, hepatocytes are capable of dividing when the organ is damaged. Because mitochondria have their own DNA, they are able to reproduce when the host cell divides. During host cell division, the number of mitochondria increases such that the daughter cells contain the same number of mitochondria as the original parent cell. Targeting healthy mitochondria to hepatocytes with defective or damaged mitochondria would confer on those cells a selective survival advantage. As a result, those cells would proliferate and eventually replace defective cells.

Patients with liver failure due to mitochondrial damage are only treated with supportive care or a liver transplant. There are currently no other treatments.

This disclosure provides a composition, including a pharmaceutical composition, comprising: an asialoglycoprotein (AsG) covalently attached to a polycation; and functional mammalian mitochondria that are at least partially purified and are bound to the AsG/polycation electrostatically.

In other aspects, this disclosure provides a method of making a pharmaceutical composition to treat or prevent a disease or condition that can benefit from increased cellular mitochondrial function, such as a liver disease (e.g., liver failure), comprising: at least partially purifying functional mitochondria from a cell; allowing AsG to be covalently attached to a polycation; and allowing the AsG, covalently bound to a highly positively charged polycation, to complex electrostatically with the mitochondria. In certain embodiments, the method further comprises providing an endosomolytic agent. In certain embodiments, the endosomolytic agent is allowed to be covalently attached to an AsG by a cleavable bond.

In other aspects, this disclosure provides a method of transplanting mitochondria into a hepatocyte, comprising providing functional mammalian mitochondria complexed with AsG-PL electrostatically; and delivering said composition to a hepatocyte. In certain embodiments, the composition further comprises an endosomolytic agent; in further embodiments, the endosomolytic agent is covalently attached to an AsG by a cleavable bond.

In certain embodiments, the AsG is any AsG that can bind to its receptor on a cell, such as a hepatocyte. In some embodiments, the AsG comprises asialoorosomucoid (AsOR).

The polycation can be any suitable polycation. In certain embodiments, the polycation is highly positively charged. In certain embodiments, the highly positively charged polycation is polylysine (PL), polyarginine, or polyornithine.

In certain embodiments, the composition further comprises an endosomolytic agent. In further embodiments, the endosomolytic agent is attached to an AsG; in yet further embodiments, the endosomolytic agent is covalently attached to an AsG; in yet further embodiments, the endosomolytic agent is covalently attached to an AsG by a cleavable bond. Any suitable endosomolytic agent can be used. In certain embodiments, the endosomolytic agent is listeriolysin. The term "listeriolysin" as used herein, includes listeriolysin, a fragment of listeriolysin having endosomolytic activity, a listeriolysin peptide having endosomolytic activity, fusion protein comprising listeriolysin, a fragment or a peptide thereof, having endosomolytic activity. See, e.g., U.S. Pat. No. 5,728,399. In certain embodiments, the endosomolytic agent is a fragment of listeriolysin having endosomolytic activity, a listeriolysin peptide having endosomolytic activity. A cleavable bond can be any cleavable bond, including, for example, a disulfide bond (cleaved, or severed, by reducing condition); acid-cleavable thio-maleamic acid, imine, acetal linker; etc. The cleavable bond can be formed by a chemical linker, by a protein, or by any bond cleavable under conditions within an endosome. The AsG molecule that is bound to an endosomolytic agent can be one that is also covalently bound to polycation or can be one that is not covalently bound to polycation. In certain embodiments, the bond cleavable under conditions that exist in endosome is a disulfide bond is one under conditions that exist in endosome, and can be a disulfide bond and an acid-labile bond, including, for example an imino-, acetal, or lactone bond.

Any method known in the art can be used to allow AsG to be covalently attached to a cation; to allow AsG/polycation to be electrostatically attached to mitochondria; and to allow an endosomolytic agent to be covalently attached to an AsG covalently by a cleavable bond.

The mitochondria can be obtained from any mammalian source, including from human cells and from rat cells. The mitochondria can be obtained from a cell from a healthy donor or isolated from a mammalian cell or tissue. In certain embodiments, the mammalian cell is a hepatocyte, white blood cell, stem cell or tissue. In certain embodiments, the mitochondria are rat or human mitochondria.

The at least partially purified mitochondria retain function, upon transplantation into another cell, such as a hepatocyte, and function as normal mitochondria. Any assay for whether the transplanted mitochondria are functional in their new host cells can be used to assess whether the mitochondria are functional.

The mitochondria are isolated and purified from a cell by any method that allows the mitochondria to retain function. The mitochondria are at least partially purified, such that no cells or nuclei are present. The mitochondria can be purified as disclosed, for example, in U.S. Patent Publication Number 2014/0193511.

Any suitable pharmaceutical compositions and formulations, as well as suitable methods for formulating and suitable route(s) and suitable site(s) of administration, are within the scope of this invention. Also, unless otherwise stated, any suitable dosage(s) and frequency of administration are contemplated.

The pharmaceutical compositions can include a pharmaceutically acceptable carrier (i.e., an excipient). A "pharmaceutically acceptable carrier" refers to, and includes, any and all solvents, any and all liquid vehicles, such as water, buffer, etc., dispersion media, coatings, antibacterial and antifungal agents, isotonic and absorption delaying agents, diluent, glidant, etc. The compositions can include a pharmaceutically acceptable salt, e.g., an acid addition salt or a base addition salt (see e.g., Berge et al. (1977) *J Pharm Sci* 66:1-19).

The terms "therapeutically effective amount" or "therapeutically effective dose," or similar terms used herein are intended to mean an amount of the disclosed pharmaceutical composition that will elicit the desired biological or medical response, such as, for example, successful treatment of liver disease caused by poor mitochondria function. Such response can be confirmed by methods known in the art.

In certain aspects, this disclosure provides a kit comprising a pharmaceutical composition disclosed herein and instruction for using said composition to treat or prevent a disease or condition that can benefit from increased cellular mitochondrial function, such as liver disease. In certain embodiments, the kit comprises an asialoglycoprotein (AsG), a polycation, and an endosomolytic agent, each in sterile solutions in separate containers, and also comprises a vial of cryopreserved mitochondria from a cell of a healthy donor or isolated from a suitable mammalian cell type, such as human white blood cells or human stem cells. The therapy kit could be stored in a freezer prior to use. In certain embodiments, when needed, the solutions and mitochondria would be carefully thawed, and immediately and thoroughly mixed, and injected intravenously into a peripheral vein of a patient with mitochondrial damage and liver disease, including liver failure.

In certain other aspects, a method is provided to treat or prevent a disease or condition that can benefit from increased cellular mitochondrial function, such as liver disease, comprising administering a therapeutically effective amount of a pharmaceutical composition disclosed herein to a patient in need thereof.

In certain embodiments, the disclosed compositions and methods may be used as therapy for patients who have mitochondrial dysfunction and liver failure due to a genetic defect. In certain embodiments, the disclosed compositions and methods may be used as therapy for patients who have acquired mitochondrial dysfunction and liver failure due to, for example, medications.

EXAMPLES

For this invention to be better understood, the following examples are set forth. These examples are for purposes of illustration only and are not be construed as limiting the scope of the invention in any manner.

Example 1

Targeting of Mitochondria to Hepatocytes and Uptake by the AsGR Pathway

Methods: An asialoglycoprotein, asialoorosomucoid (AsOR), was fluorescently labeled to make Fl-AsOR. Fl-AsOR was covalently linked to polylysine to create a positively charged conjugate Fl-AsOR-PL, capable of binding mitochondria, which are negatively charged. GFP-labeled rat mitochondria were isolated from HTC mito-GFP cells and mixed with Fl-AsOR-PL to form stable electrostatically bound complexes. To assess targeted delivery of mitochondria to hepatocytes, Fl-AsOR-PL-mitochondria complexes were incubated separately with Huh7 AsG receptor (+), and SK Hep1 cells AsG receptor (−) human hepatoma cell lines at 37° C., and cells sampled at various time points. After extensive washing, intracellular uptake of rat mitochondria was assayed by qPCR using primers specific for rat mitochondrial DNA, by dual photon confocal fluorescence microscopy to detect GFP, and by anti-EEA antibody followed by Alexafluor 594 to detect early endosomes.

Results: Fluorescence data showed that the Fl-AsOR-PL conjugate remained stably bound to mitochondria after multiple spin and re-suspension cycles.

Incubation of Fl-AsOR-PL-mitochondria complexes with cells showed that only Huh7 [AsG receptor (+)], but not SK Hep1 [AsG receptor (−)], cells had significant Fl-AsOR fluorescence, and that fluorescence increased with time. qPCR confirmed that rat mitochondrial DNA increased with time in Huh7, but not SK Hep1 cells. Incubation of Fl-AsOR-PL-mitochondria complexes with Huh7 cells in the presence of a large molar excess of free AsOR blocked the association of fluorescence with those cells. Confocal microscopy confirmed the presence of intracellular mitochondria. Overlapping GFP and Alexafluor 594 indicated the presence of Fl-AsOR-PL-mitochondria in endosomes. Co-targeting of an endosomolytic agent confirmed initial co-localization of mitochondria in endosomes, as well as intracellular rat mitochondria unassociated with endosomes.

Thus, coupling of polylysine to AsOR results in a strongly positively charged conjugate, Fl-AsOR-PL, which bound mitochondria in a stable non-covalent interaction. Fl-AsOR-PL-mitochondria complexes were taken up by hepatocytes by receptor-mediated endocytosis, and levels of endocytosed complexes increased with time. Co-targeting of an endosomolytic agent increased co-localization of mitochondria in endosomes and also increased the number of intracellular rat mitochondria not associated with endosomes.

Example 2

Targeting of Mitochondria to Hepatocytes and Uptake by the AsGR Pathway

Figure 2:
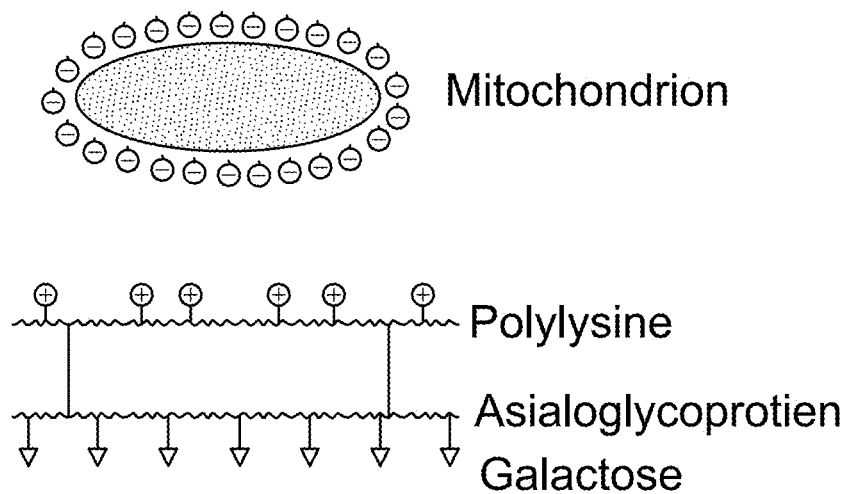
FIG. 2. A diagram of an asialoglycoprotein-polylysine (AsG-PL) conjugate for binding to mitochondria.

Asialoglycoproteins (AsG) can be used as a carrier targetable to deliver substances to the liver if they can be bound to the substance to be delivered. However, in the case of mitochondria, they are delicate organelles which can be damaged by chemicals. Therefore, it was important to develop a method by which AsG could be bound to mitochondria in a non-damaging interaction. As mitochondria are negatively charged, a method was devised by which an asialoglycoprotein is converted into a highly positively charged molecule. Then, by mixing this protein conjugate with mitochondria, the conjugate could bind to mitochondria in a strong, but non-damaging electrostatic (charge-charge) interaction forming protein-mitochondrial complexes, FIG. 2. AsG was converted into a positively charged molecule by chemically linking it to a peptide, polylysine (PL), consisting of polymer of the positively charged amino acid, lysine.

Preparation and Fluorescent Labeling of an Asialoglycoprotein-Polylysine (AsOR-PL) Conjugate An AsG, asialoorosomucoid (AsOR), was labeled with a fluorescent tag, dylight 650. Then, polylysine (average MW 1 kDa) was linked to the AsG, asialoorosomucoid (AsOR), using a covalent linker, carbodiimide, and purified by molecular sieve chromatography.

Figure 3:
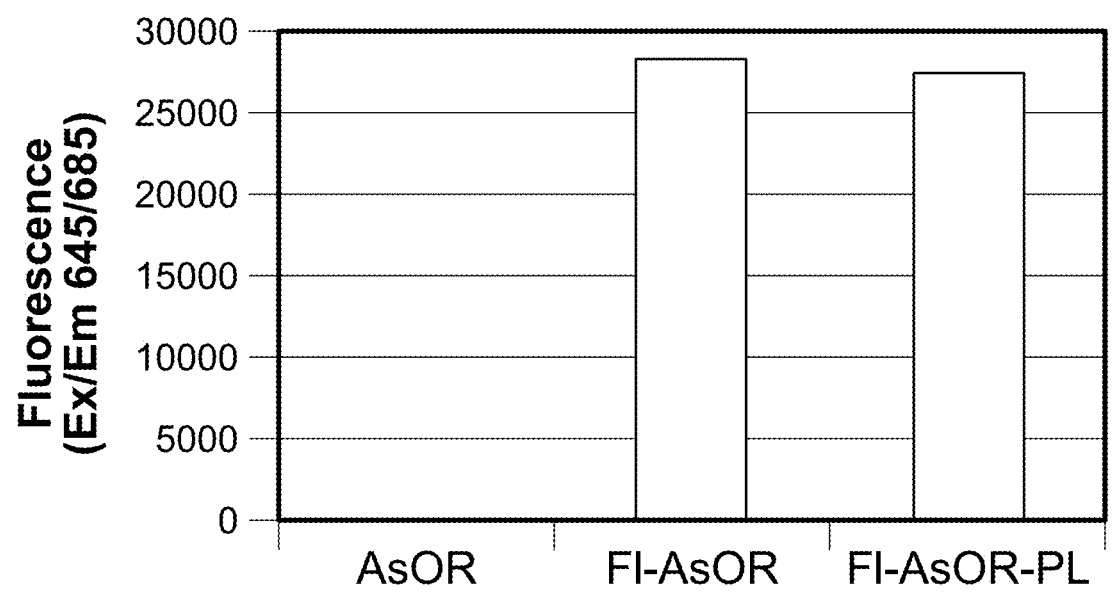
FIG. 3. Fluorescence of asialoorosomucoid (AsOR) conjugates measured with spectrophotometer (XFLUOR-4SAFIREII Version: V 4.62n). An AsG, asialoorosomucoid (AsOR), was labeled with a fluorescent tag, dylight 650. Then, polylysine was linked to the AsG, asialoorosomucoid (AsOR).

One μg of each protein was used to determine fluorescence intensity of dylight 650 labeled protein. FIG. 3 shows that AsOR itself, as expected, had no fluorescence. However both AsOR, and AsOR-polylysine conjugate labeled with the fluorescent tag had fluorescence, and the specific fluorescence (per mg) was similar for Fl-AsOR and Fl-AsOR-PL.

Conclusions: An AsOR-PL conjugate was successfully labeled with a fluorescent tag.

Figure 4:
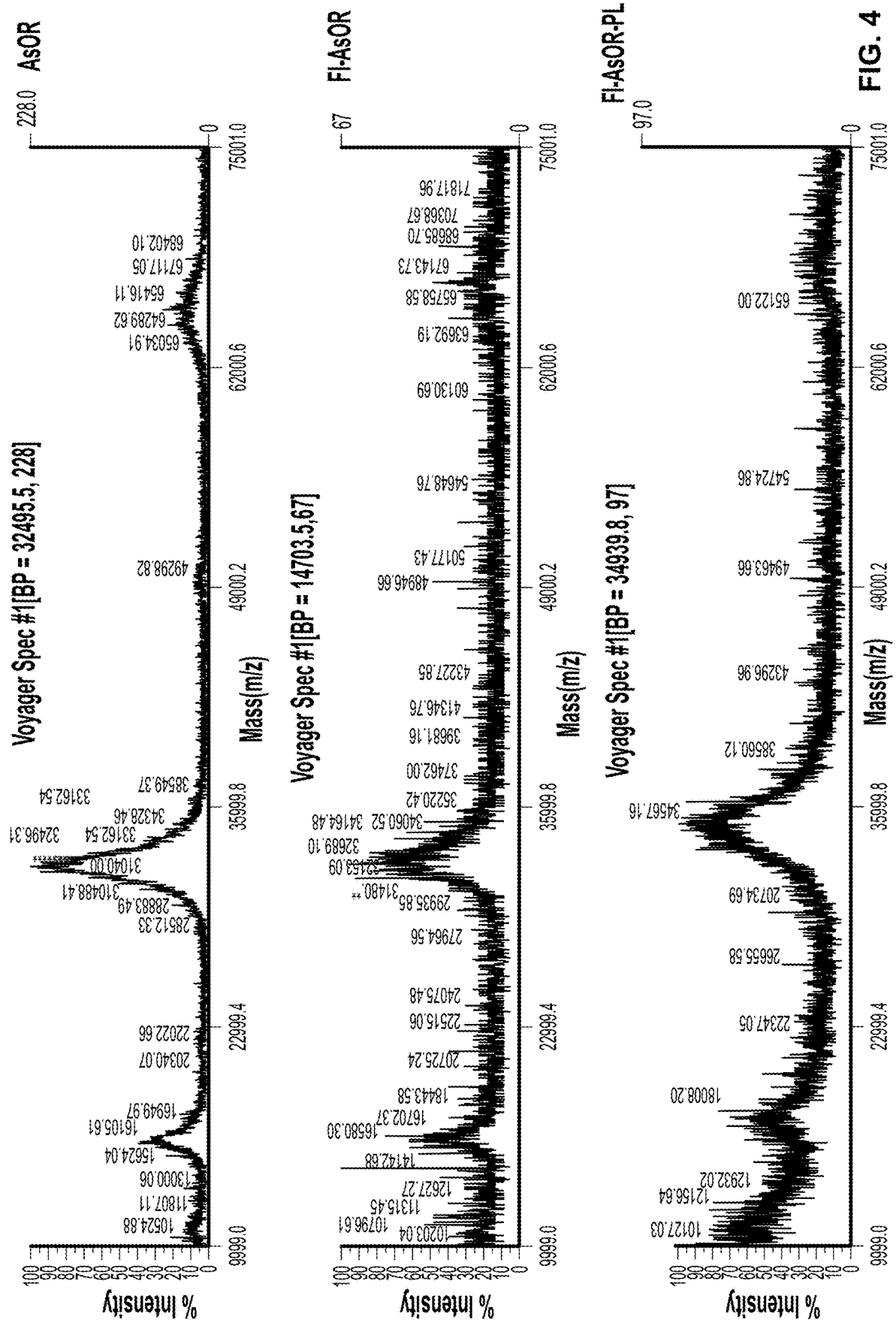
FIG. 4. Results of mass spectrometric analyses of ASOR conjugates. An AsG, asialoorosomucoid (AsOR), was labeled with a fluorescent tag, dylight 650. Then, polylysine (average MW 1 kDa) was linked to the AsG, asialoorosomucoid (AsOR), using a covalent linker, carbodiimide and purified by molecular sieve chromatography. Data shows that the average masses were: AsOR was 32.8 kDa; Fl-AsOR, 33.4 kDa; and Fl-AsOR-PL, 35.2 kDa.

Measurement of the Mass of a Fluorescent Asialoglycoprotein-Polylysine (Fl-AsOR-PL) Conjugate After coupling AsOR to PL, the purified conjugate was submitted for mass spectral analysis. FIG. 4 shows mass spectrometric data that indicates that the average mass of AsOR was 32.8 kDa. The average mass of Fl-AsOR was slightly higher, 33.4 kDa, and that of Fl-AsOR-PL was considerably higher, 35.2 kDa.

Conclusions: FL-AsOR was covalently linked to PL. Calculation of the mass spectral data revealed that on average, two dylight 650 tags were covalently bound per AsOR molecule, and two PL chains were bound per FL-AsOR-PL molecule.

Evaluation of Charge on Asialoglycoprotein-Polylysine (AsOR-PL) Conjugate

Figure 5:
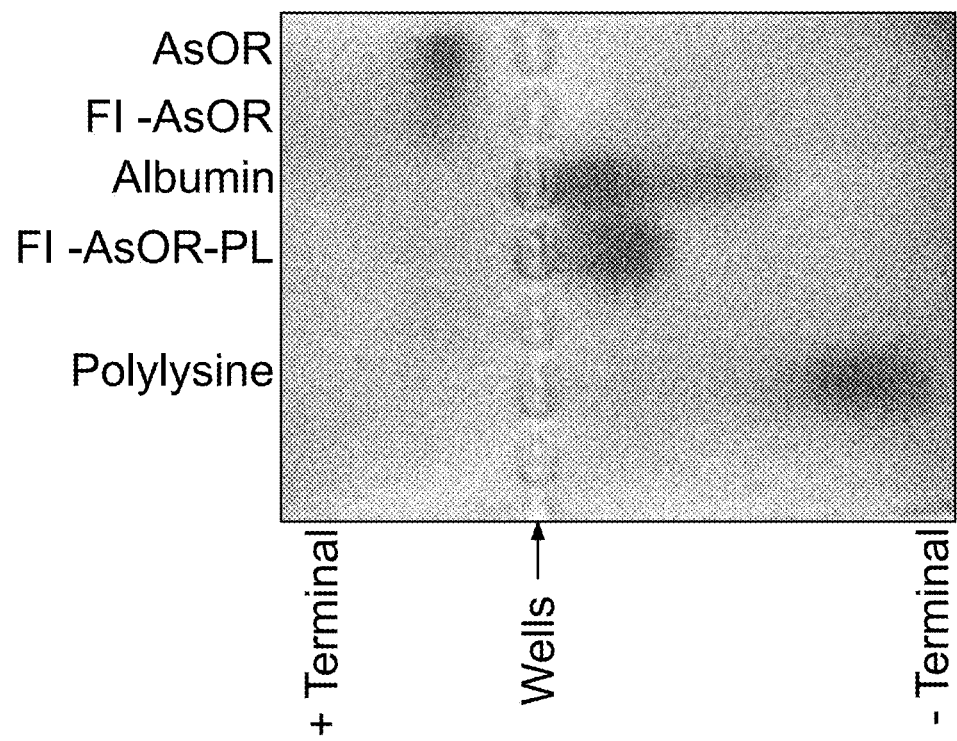
FIG. 5. An agarose gel electrophoresis of starting materials and Fl-AsOR-PL. Proteins were run on 0.8% agarose gels. Proteins were loaded near the middle of gel to assess migration in both directions.

Agarose gel electrophoresis was run to determine whether the AsOR-PL conjugate was positively charged. FIG. 5 shows that both AsOR and Fl-AsOR moved towards positive terminal indicating that they were negatively charged. In contrast, Fl-AsOR-PL, like PL, moved towards negative terminal. The Fl-AsOR-PL conjugate ran as a single band. There was no free AsOR or free PL.

Conclusions: AsOR was covalently linked to PL to form AsOR-PL conjugate, and the purification process eliminated all starting materials. In contrast to AsOR, the AsOR-PL conjugate was positively charged.

Evaluation of Uptake of AsOR-PL Conjugate

Figure 6:
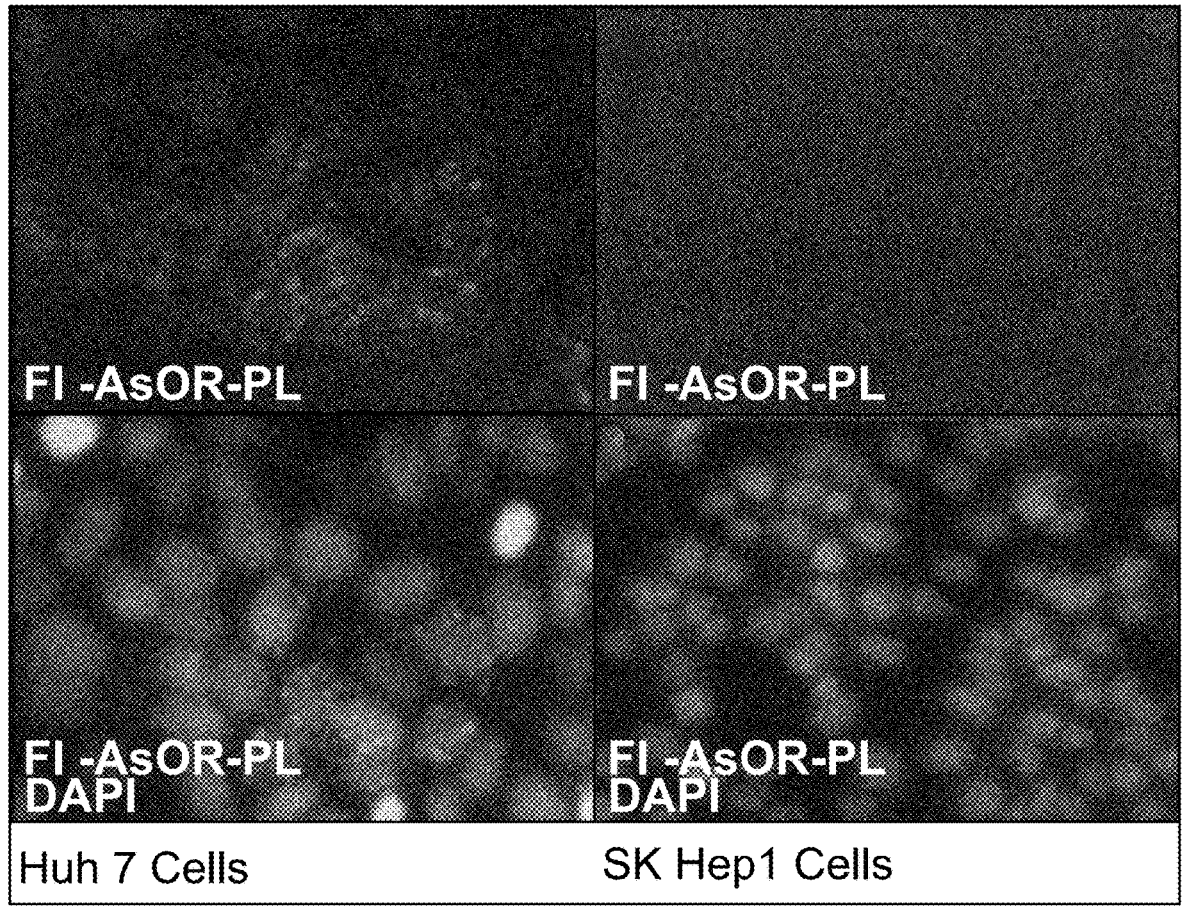
FIG. 6. Uptake of an asialoglycoprotein-polylysine (AsOR-PL) carrier. Fl-AsOR-PL was incubated with cells for 1 h at 37° C., and fluorescence microscopy was performed.

To test whether chemical linkage of PL to AsOR might have altered AsOR recognition by AsG receptors, binding of AsOR-PL to AsG receptors was studied using [AsG receptor (+)], SK Hep1 [AsG receptor (−)] cells. Fl-AsOR-PL was incubated with cells for 1 hour (h) at 37° C., and fluorescence microscopy was performed. DAPI was used to stain nuclei a different color (green) compared to that of AsOR (red). FIG. 6 shows that Huh7 [AsG receptor (+)] cells incubated with Fl-AsOR-PL resulted in numerous small punctate red structures, FIG. 6 upper left panel. Some structures surrounded nuclei shown in the lower panel indicating that those structures were intracellular, and the size suggested endosomal vesicles, FIG. 6 lower left panel. In contrast, SK Hep1 cells [AsG receptor (−)] lacked any detectable small punctate red structures, FIG. 6 upper panel; see also FIG. 6 lower right panel (DAPI staining).

Conclusions: AsOR-PL conjugates were capable of internalization. The resulting appearance of a punctate pattern is consistent with entry of AsOR-PL into endosomes. The fact that the fluorescence appeared only in Huh7 [AsG receptor (+)], but not SK Hep1 cells [AsG receptor (−)] is consistent with uptake of the former by AsG receptors. The AsOR-PL is taken up specifically by AsG (+) cells.

Figure 7A:
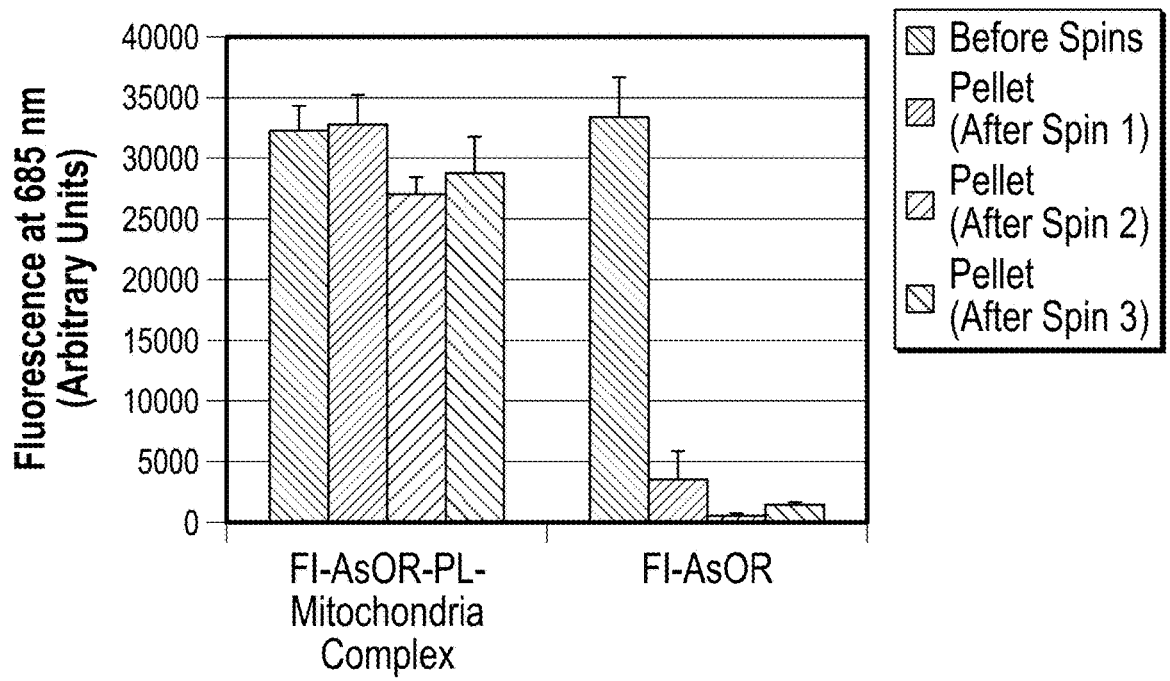
FIG. 7A. Protein-associated fluorescence levels in mitochondrial pellets.
Figure 7B:
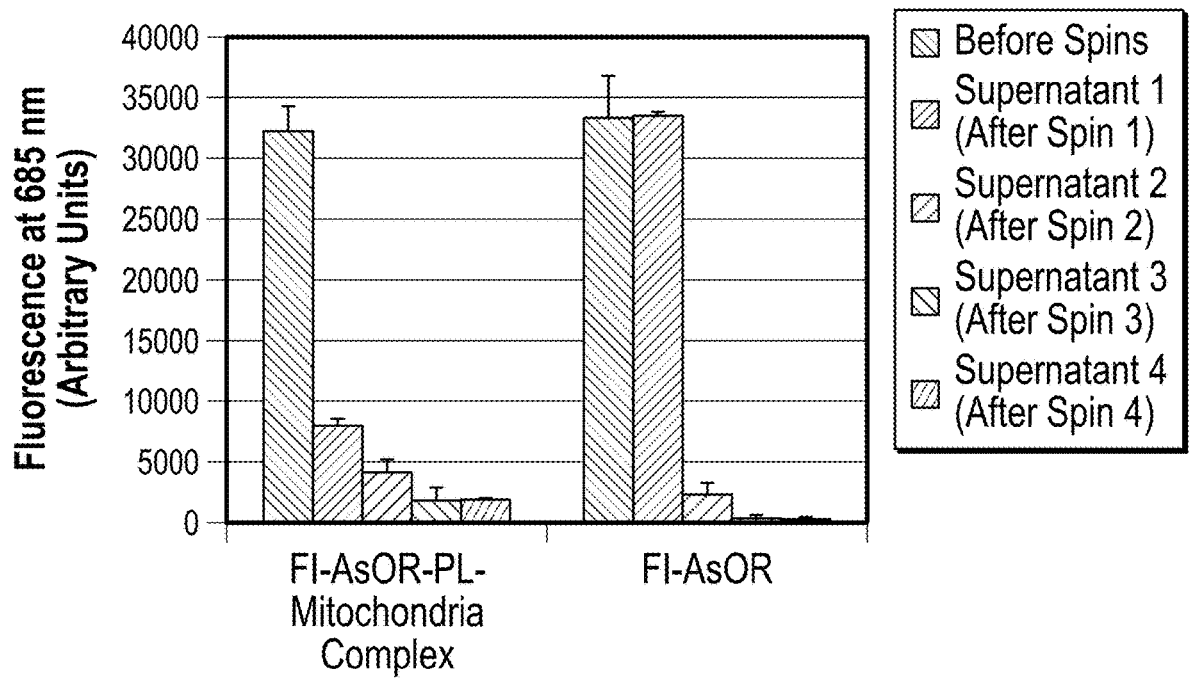
FIG. 7B. Protein-associated fluorescence levels in supernatants.

Formation and Stability of an Asialoglycoprotein-Polylysine (AsOR-PL) Conjugate—Mitochondrial Complexes To determine whether AsOR-PL could bind stably to mitochondria, mitochondria were isolated from rat hepatocytes, HTC cells. This non-human species as the source of mitochondrial was selected in order to be able to distinguish transplanted mitochondria from existing human host cell mitochondria. Freshly isolated rat mitochondria were incubated with Fl-AsOR-PL, and repeatedly centrifuged and re-suspended in fresh medium. FIG. 7A shows that the fluorescence of the Fl-AsOR-PL decreased by about 15% after the first spin, and then remained constant at approximately 27,000 units, in the pelleted mitochondria through the 3rd spin. Furthermore, little fluorescence remained in the supernatant, and what little fluorescence was present also remained constant as shown in FIG. 7B. In contrast, Fl-AsOR alone, lacking PL, and therefore, not be expected to bind strongly to mitochondria, decreased by more than 90% from 30,000 to 3,000 units after the first spin, and then was no longer detected with pelleted mitochondria after subsequent spins, as shown in FIG. 7A.

Conclusions: AsOR-PL conjugate remained associated with mitochondria despite repeated centrifugation. AsOR without PL remained in the supernatant, and did not associate with the mitochondrial pellet. Because of its small size, AsOR-PL alone cannot be pelleted by this centrifugation process. The finding of AsOR-PL associated with the mitochondrial pellet supports binding of AsOR-PL to mitochondria stable to the conditions of washing and spinning.

Measurement of the Average Size of AsOR-PL-Mitochondrial Complexes

Figure 8:
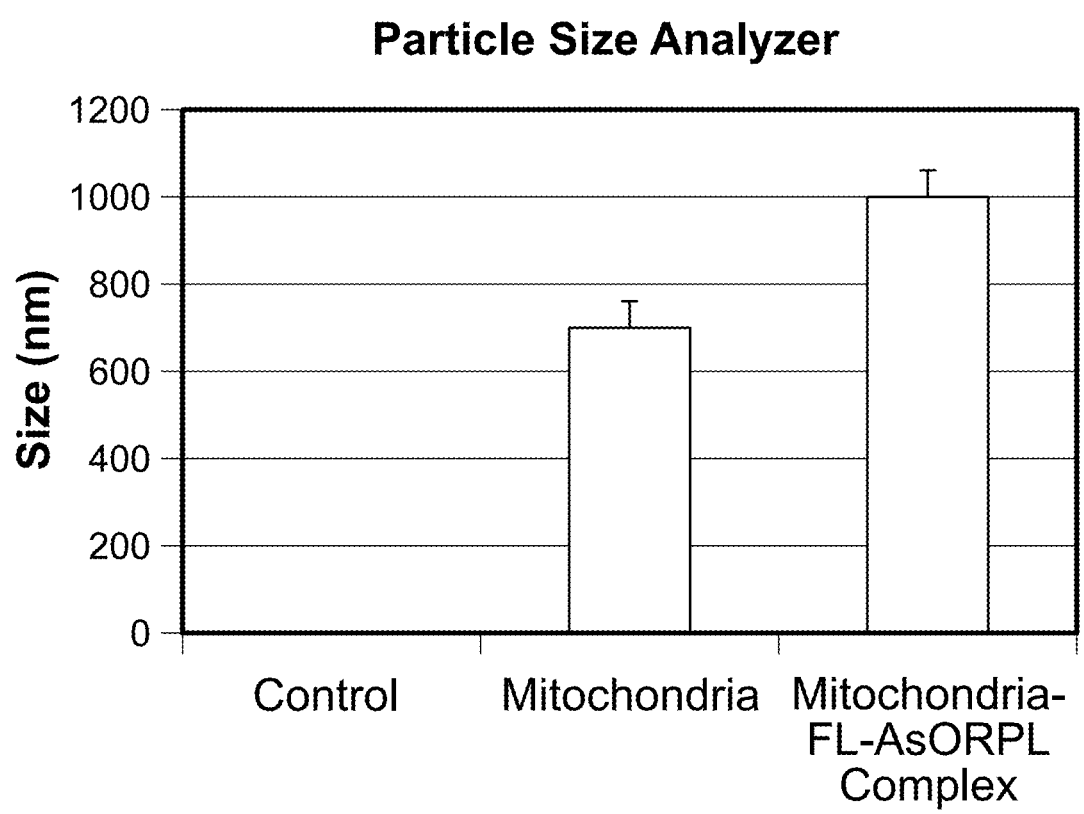
FIG. 8. Particle size analysis of AsOR-PL-mitochondrial complexes.

The size of protein-mitochondrial complexes was determined by particle size analysis. FIG. 8 shows that the mean diameter of mitochondria increased by approximately 300 nm when complexed with AsOR-PL. The mean diameter of mitochondria alone was 700+57.8 nm while AsOR-PL complexed mitochondria had a mean diameter of 1000+62 nm.

Conclusions: The formation of AsOR-PL complexes is associated with an increase in size. The fact that the average diameters did not increase as a multiple of 700 nm suggests that the increase in size was not simply due to aggregation of mitochondria.

Uptake of AsOR-PL-mitochondrial Complexes as Measured by Fluorescence

Figure 10A:
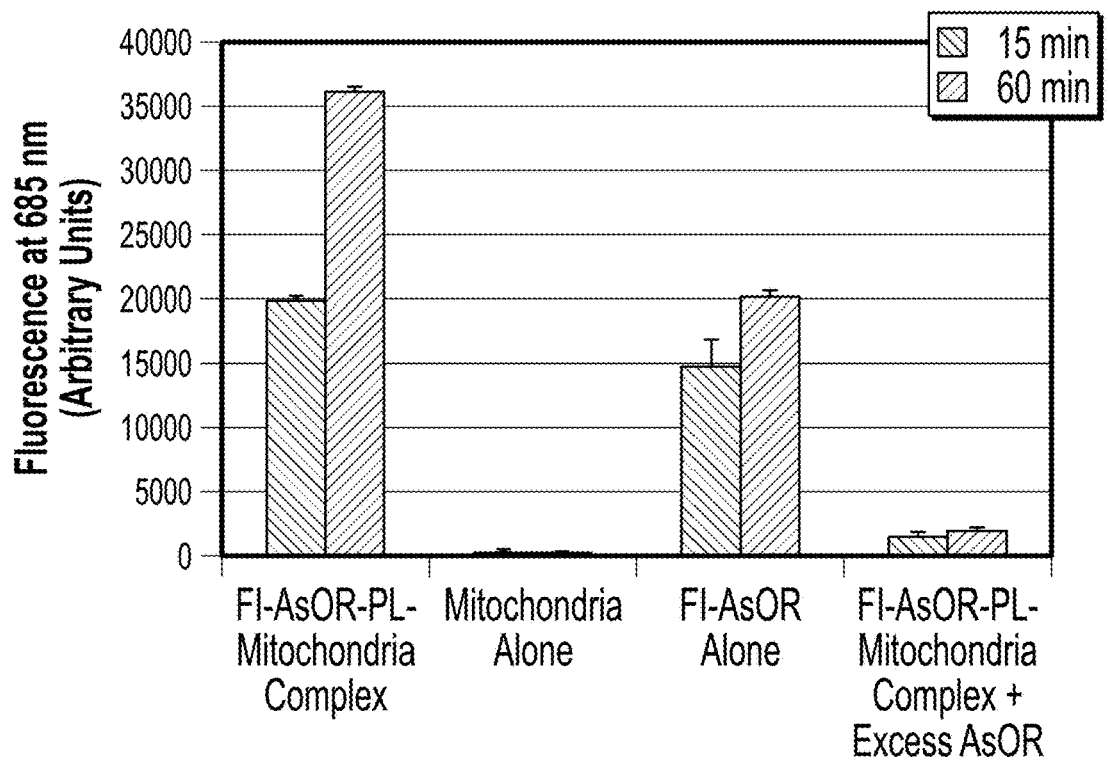
FIG. 10A, fluorescence levels in Huh 7 cells.
Figure 10B:
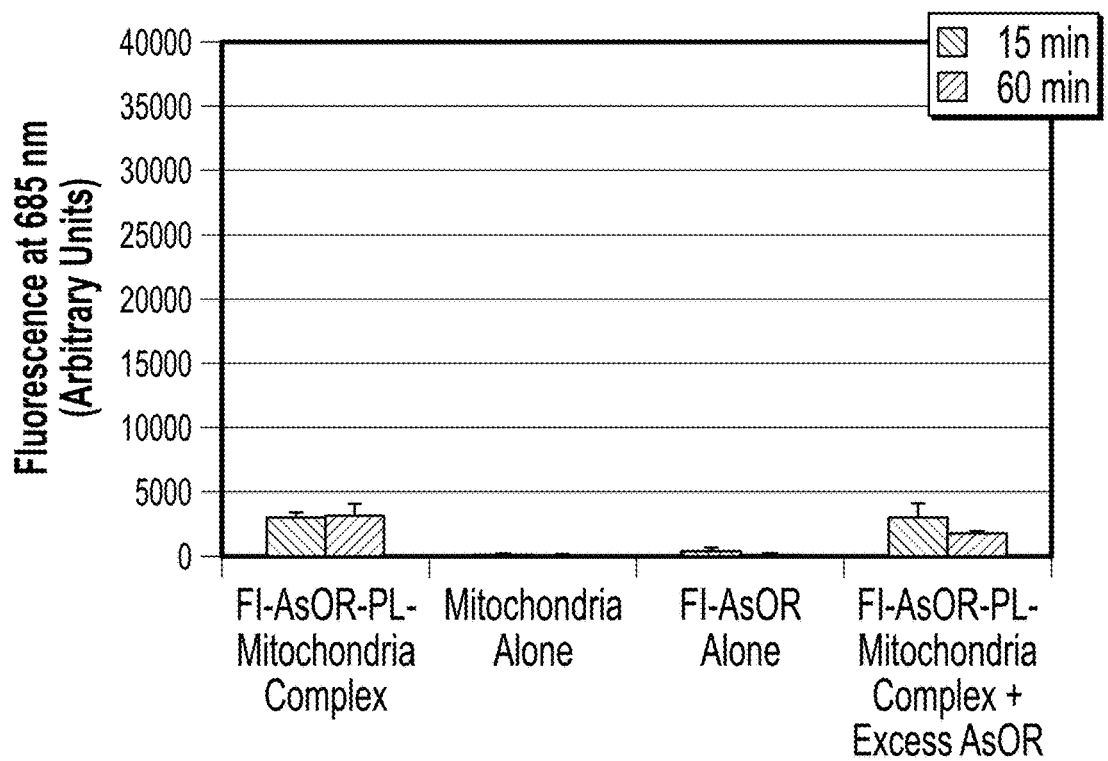
FIG. 10B, SK Hep 1 cells incubated with complexed mitochondria or controls. Mitochondrial DNA levels after incubation with FIG. 10C, Huh 7 cells.
Figure 10C:
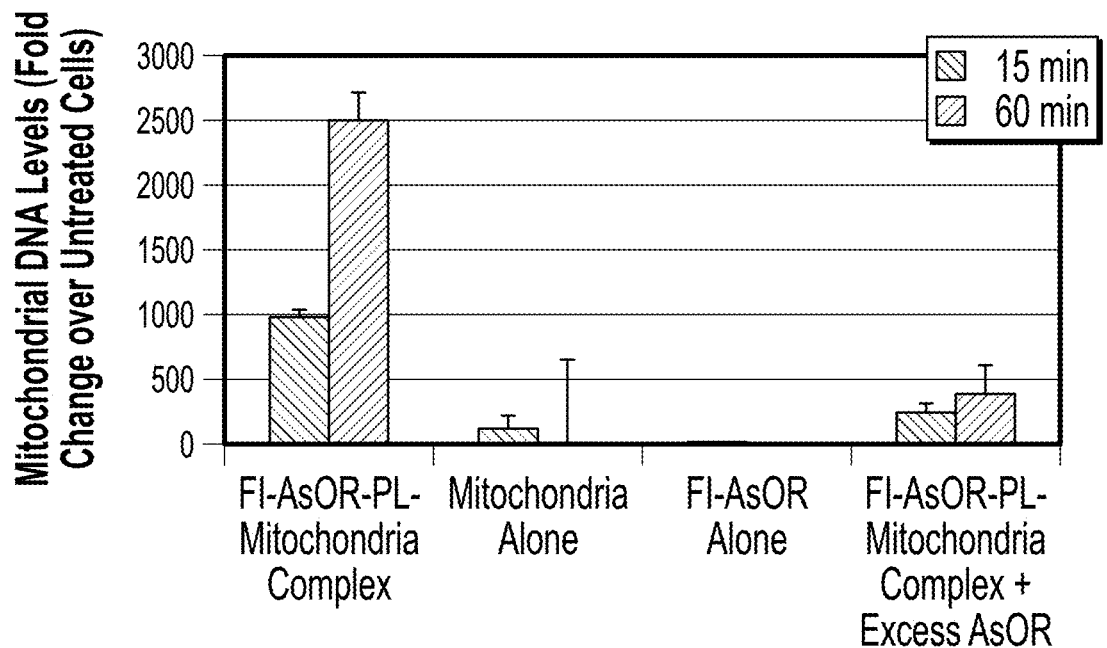
FIG. 10. Uptake of Fl-AsOR-PL-mitochondria complexes by Huh 7 and SK Hep1 cells as measured by fluorescence and qPCR. Cells were incubated separately with mitochondria alone, Fl-AsOR alone, Fl-AsOR-PL-mitochondria complex, or complexed mitochondria+excess AsOR for 1 h and collected for analysis at various time points.
FIG. 10D, SK Hep1 cells.
Figure 10D:
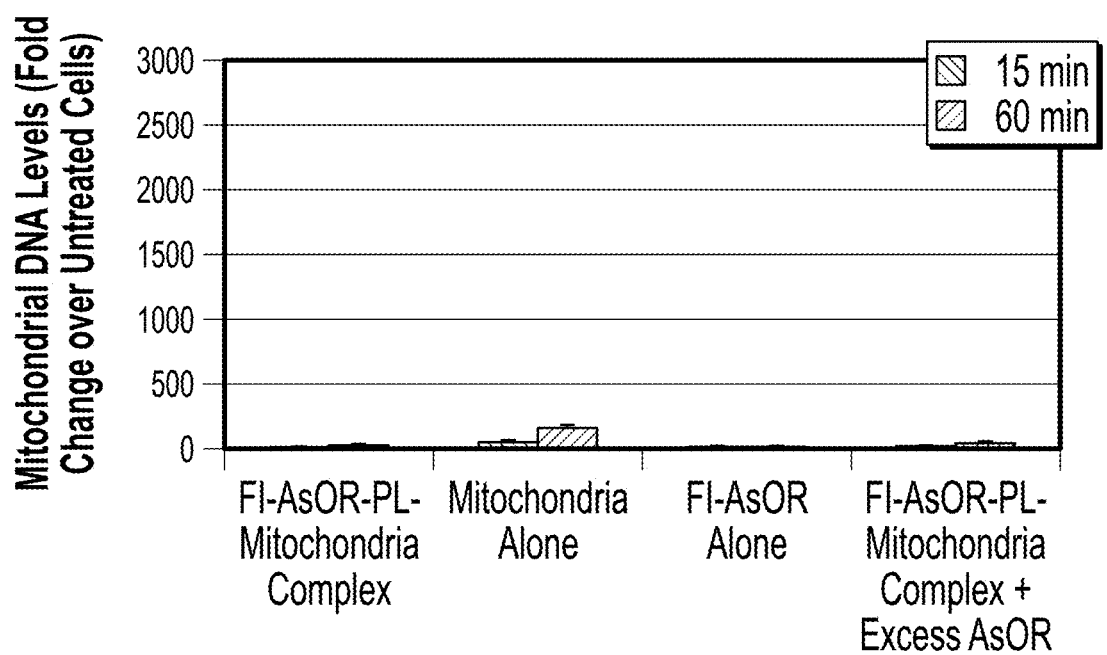

To measure uptake, Huh7 [AsG receptor (+)] and SK Hep1 [AsG receptor (−)] cells were separately incubated with Fl-AsOR-PL mitochondrial complexes, mitochondria alone, Fl-AsOR protein alone, and excess AsOR were added to compete with of Fl-AsOR-PL mitochondrial complexes at 37° C. as a function of time. FIG. 10A shows that fluorescence from AsOR in Huh7 cells reached 20,000 units at 15 minutes (min), and increased to 35,000 units at 1 h. This is similar to the levels of Fl-AsOR which reached 15,000 units at 15 min, and increased to 20,000 units at 1 h. In contrast, mitochondria alone, had no fluorescence. Furthermore, addition of a large molar excess of AsOR to complexed mitochondria resulted in less than 2500 units at both 15 min and 1 h. Uptake of fluorescence by SK Hep1 cells in the presence of Fl-AsOR-PL mitochondrial complexes did not exceed 2500 units, FIG. 10B. The lack of uptake by AsG receptor (−) cells and the competition inhibition of uptake by excess free AsG support the notion that the uptake in Huh7 cells was mediated by the AsG receptor. Huh 7 cells incubated with Fl-AsOR-PL-mitochondria complex resulted in a significant (p<0.004) increase, 990-fold, over HTC mitochondrial DNA levels, approximately 6-14 HTC mitochondria per cell, (based on reported copies of mitochondrial DNA/mitochondrion) compared to untreated cells at 15 min, and increased to more than double (approximately 14-36 HTC mitochondria per cell) (p<0.001) at 60 min, FIG. 10C. Huh 7 cells incubated with either mitochondria alone or Fl-AsOR alone had no significant HTC mitochondrial DNA levels. Exposure of Huh 7 cells to Fl-AsOR-PL-mitochondria complex with excess free AsOR resulted in HTC mitochondrial DNA levels in Huh 7 cells that were 76% (p<0.001) lower than complexes without excess AsOR. In contrast, HTC mitochondrial DNA levels in SK Hep1 cells were barely detectable under any condition, FIG. 10D. The data suggested that complexed mitochondria were taken up by Huh 7 cells specifically mediated by the AsGR.

Conclusions: AsOR-PL-mitochondrial complexes can be taken up by cells that possess AsG receptors, but not by those cells that do not. Mitochondria alone do not have measurable uptake indicating that the observed uptake was not due to non-specific mitochondrial binding to cells. The competition with excess AsOR confirms that the specificity of uptake is consistent with that of AsG receptors.

Uptake of AsOR-PL-Mitochondrial Complexes as Measured by Mitochondrial DNA

To confirm that the observed fluorescence results were not due to some non-specific association of fluorescence to cells, uptake of complexed mitochondria was measured by PCR of rat mitochondrial DNA. Table 1 shows the primers used to achieve specificity for rat mitochondrial DNA. Complexed mitochondria incubated with Huh7 cells resulted in DNA levels 1000 fold over untreated cells at 15 min, and increased to 2500 fold at 1 h, FIG. 10C. Neither mitochondria alone, AsOR-PL alone, FIG. 10C, nor complexed mitochondria with SK Hep1 cells, FIG. 10C, resulted in DNA levels that exceeded 250 over untreated controls.

TABLE 1

Sequences of Primers Used for Quantification

| Primers | Sequences | SEQ ID NO: |
|---|---|---|
| LDHA FW | 5' TAATGAAGGACTTGGCAGATGAACT 3' | 1 |
| LDHA RV | 5' ACGGCTTTCTCCCTCTTGCT 3' | 2 |
| HTC Mito FW | 5' AGGCTTAAAAGCAGCCATCA 3' | 3 |
| HTC Mito RV | 5' GACAATGGTTATCCGGGTTG 3' | 4 |

FW, forward; RV, reverse; LDHA, human lactate dehydrogenase A; mito, mitochondria.

Conclusions: Mitochondrial DNA associated with cells increased with time only in Huh7 [AsG receptor (+)] cells. Incubation of mitochondria alone had no significant association with either cell line confirming the fluorescence data that the association of rat mitochondrial DNA in the form of AsOR-PL complexes was associated only with AsG receptor (+) cells and increased with time.

The usual fate of substances entering the endocytotic pathway is degradation following fusion of endosomes with lysosomes. This would result in destruction of the targeted substances including mitochondria. Release from endosomes may occur, but is a rare event. However, it is known that several organisms have evolved mechanisms for escape from endosomes prior to fusion with lysosomes. For example, the bacterium, *Listeria monocytogenes*, has developed a protein, listeriolysin O (LLO), which it secretes when the organism is ingested within endosomes. In an acidic environment, listeriolysin has the property of creating pores in membranes. Shortly after endosomes form, the pH normally decreases. If LLO is present, the drop in pH results in perforation of the endosomal membrane, and endosomal rupture releasing the listeria.

Figure 11:
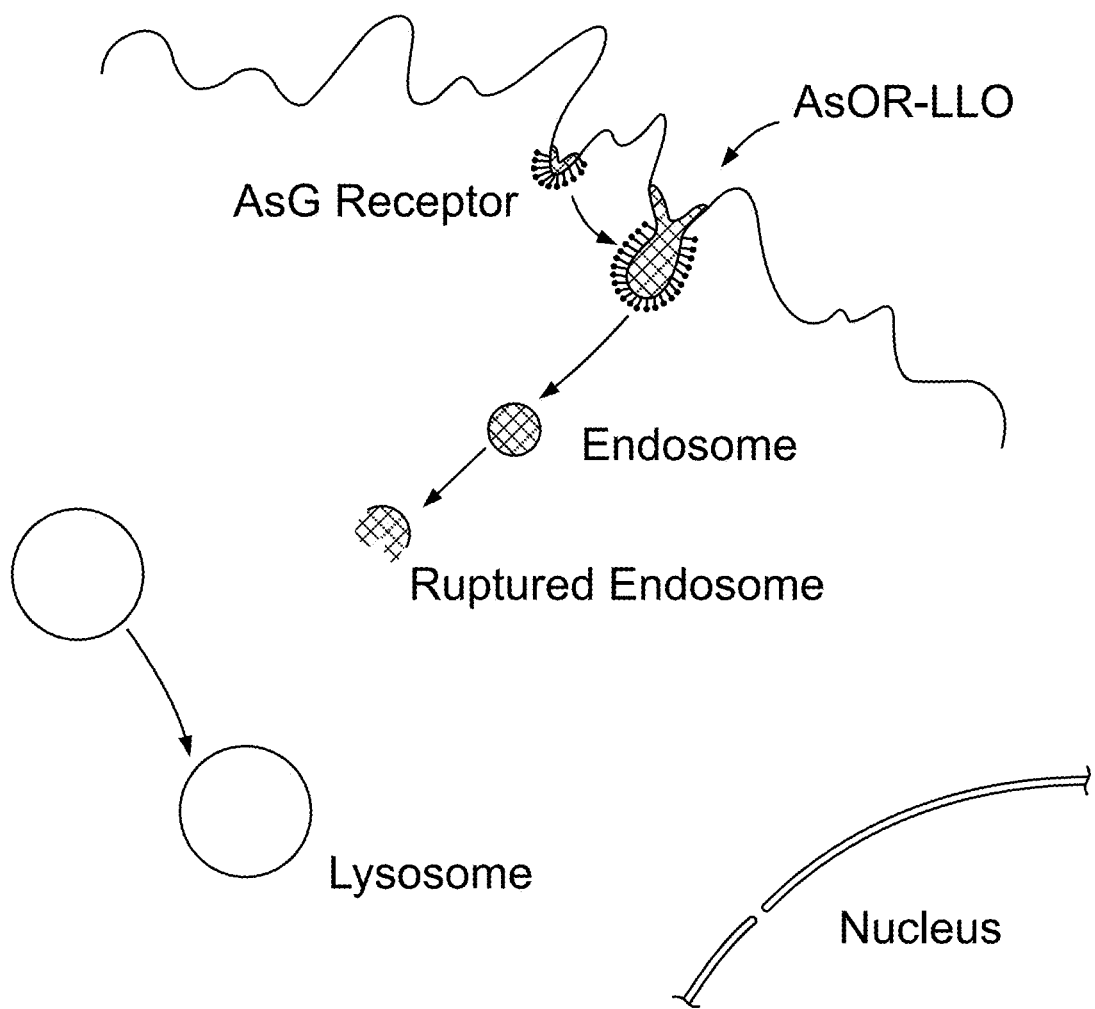
FIG. 11. A diagram of targeted listeriolysin (LLO)-mediated endosomal rupture.
Figure 12:
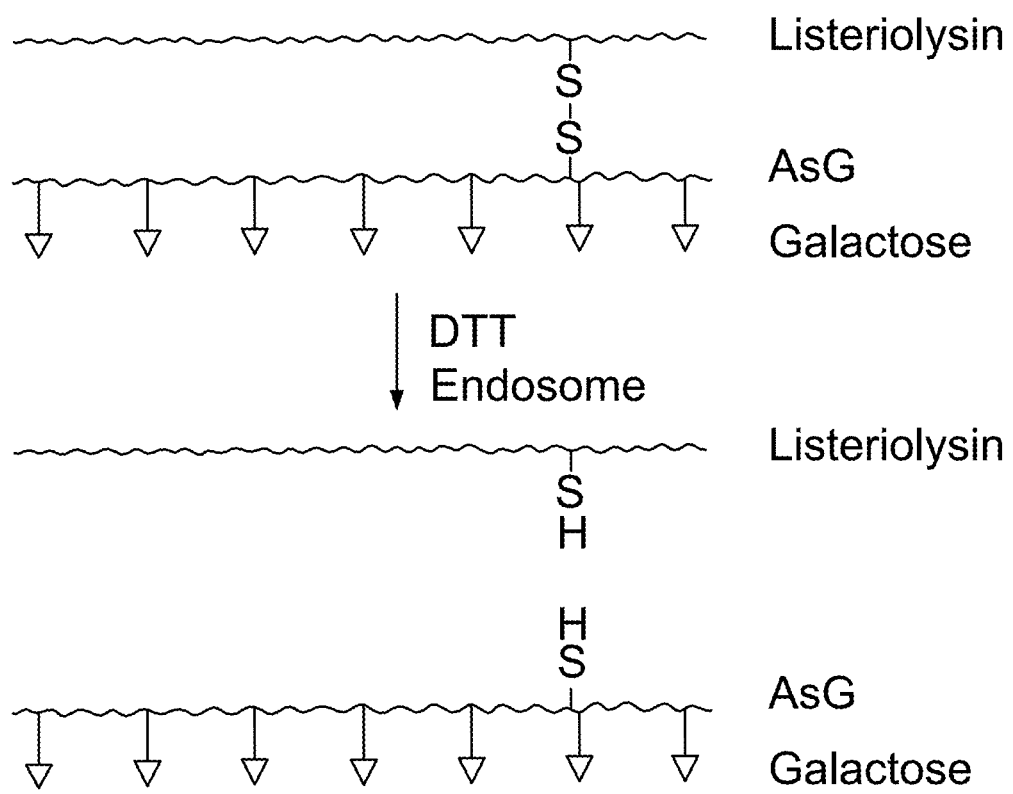
FIG. 12. A diagram of a cleavable covalent linkage of AsOR to listeriolysin (LLO).

If both mitochondrial complexes, and LLO conjugate could be made to enter the same endosomes, LLO could rupture endosomes releasing complexed mitochondria in a fashion analogous to that of listeria, FIG. 11. However, chemical linkage of LLO to AsOR might inactivate LLO. Therefore, LLO was covalently linked to AsOR through a disulfide bond. This bond is known to be cleaved in the endosomal environment, and would be expected to release intact LLO in endosomes, FIG. 12.

A Cleavable Covalent Linkage of ASOR to Listeriolysin (LLO)

Figure 13:
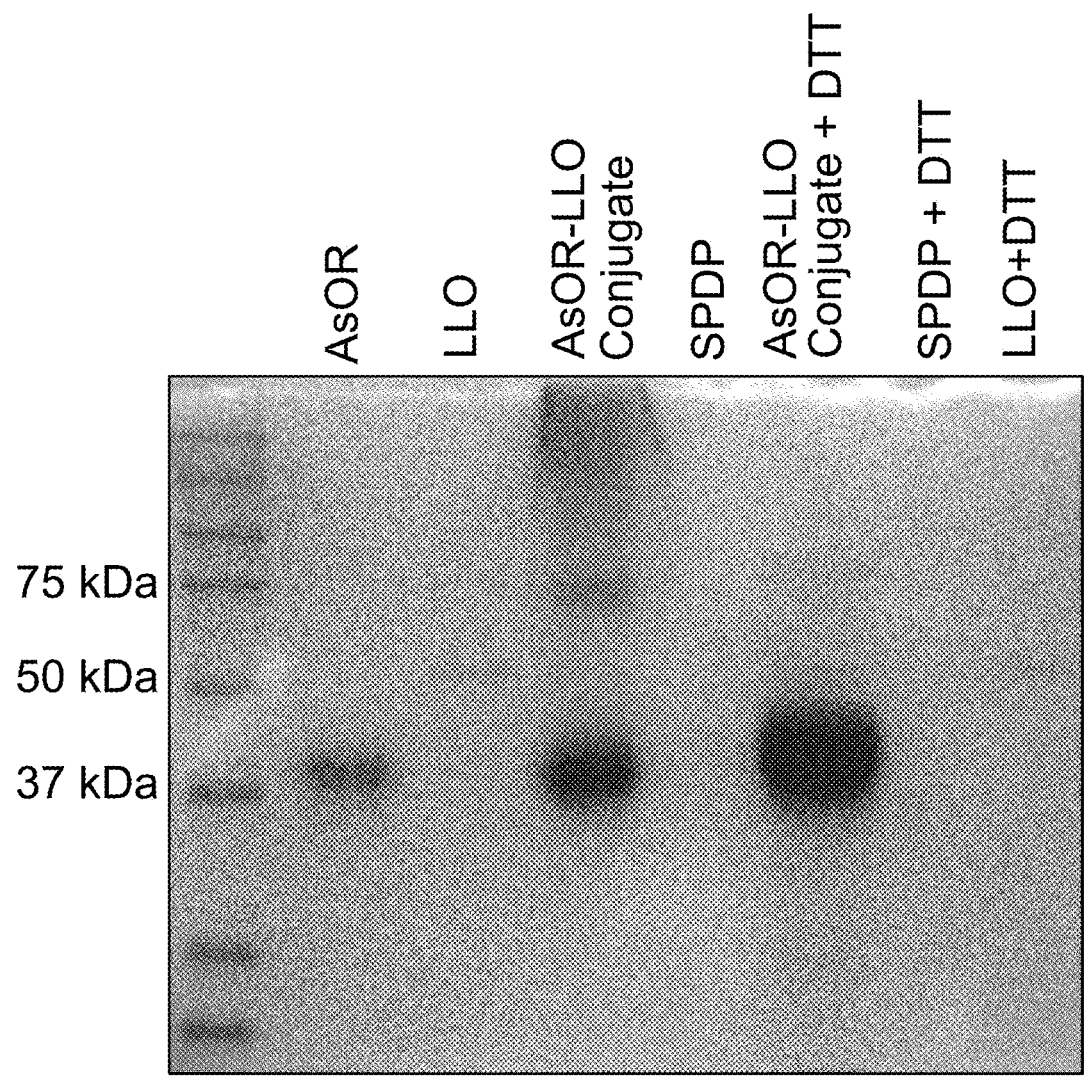
FIG. 13. SDS-PAGE of AsOR-LLO conjugate and components stained with Coomassie Brilliant Blue. Proteins were run on a 10% SDS-PAGE and stained with Coomassie blue. Lanes: 1, AsOR-LLO conjugate reduced with DTT; 2, AsOR-LLO conjugate; 3, LLO; 4, AsOR.

To deliver LLO in its natural unmodified state, AsOR was linked to LLO by SPDP, a disulfide linker known to be cleaved under reducing conditions as exist in endosomes and in the presence of dithiotheitol (DTT). FIG. 13 shows by polyacrylamide gel that AsOR-LLO conjugate was found to migrate in a position consistent with a mass of 75 kDa, larger than either AsOR or LLO. In this sample, there was a large amount of free AsOR, but no free LLO. In the presence of a reducing agent, DTT, the AsOR-LLO conjugate disappeared, the AsOR band increased, and the LLO band reappeared. These data indicate that AsOR was stably coupled to LLO by SPDP, and LLO is released from bondage to AsOR under reducing conditions.

Retention of Membranolytic Properties of LLO

To determine whether the AsOR-LLO conjugate retained membrane active properties, hemolysis assays were performed. Red blood cells exposed to LLO at low pH are known to be ruptured due to pore formation, releasing hemoglobin. Fresh human red blood cells were incubated with AsOR-LLO conjugates and controls, at neutral and low pH, with and without DTT, and hemolysis measured at 37° C. Table 2 shows that at low concentrations (below 0.1 µg/200 µl), LLO was less than 18%. At 0.1 µg/200 µl, hemolytic activity was higher 32.8% at pH 5.6 compared to 0.87% at pH 7.4. Hemolytic activity was much higher, 88.6% in the presence of a reducing agent, DTT, compared to 32.8% without. Similarly, the AsOR-LLO conjugate hemolytic activity at concentrations below 1.5 was less than 14%. At 1.5, and in presence of DTT, and the AsOR-LLO conjugate was more active, 55.3% at pH 5.6 compared to 32.7% at pH 7.4. Cholesterol inhibited the activity of both LLO and AsOR-LLO complex. 50% Hemolytic complement (CH50) activity of both LLO and AsOR-LLO conjugate were calculated.

TABLE 2

Hemolytic activity of LLO and AsOR-LLO conjugate. Values represent % hemolysis in water

| | Protein (μg/200 μl) | Conditions at pH 7.4 | | | | Conditions at pH 5.6 | | | |
|---|---|---|---|---|---|---|---|---|---|
| | | PBS | DTT | Cholesterol | DTT + Cholesterol | PBS | DTT | Cholesterol | DTT + Cholesterol |
| LLO | 0.001 | 0.00 | 0.09 | 0.34 | 6.69 | 1.30 | 1.03 | 0.10 | 0.01 |
| | 0.01 | 0.12 | 10.2 | 0.22 | 6.29 | 16.0 | 17.6 | 0.89 | 0.25 |
| | 0.1 | 0.87 | 68.7 | 0.00 | 0.72 | 32.8 | 88.6 | 0.00 | 0.00 |
| AsOR-LLO | 0.6 | 0.00 | 5.96 | 0.96 | 1.35 | 0.00 | 2.81 | 0.00 | 0.00 |
| | 1 | 0.00 | 14.0 | 0.11 | 0.80 | 0.00 | 12.5 | 0.00 | 0.00 |
| | 1.5 | 0.00 | 32.7 | 0.00 | 0.98 | 0.00 | 55.3 | 0.00 | 0.00 |

Conclusions: Conjugation of LLO to AsOR resulted in retention of hemolytic activity, and pH dependence. However, the hemolytic activity was concentration dependent.

Effects of AsOR-LLO on Uptake of Targetable Mitochondrial Complexes

Figure 14A:
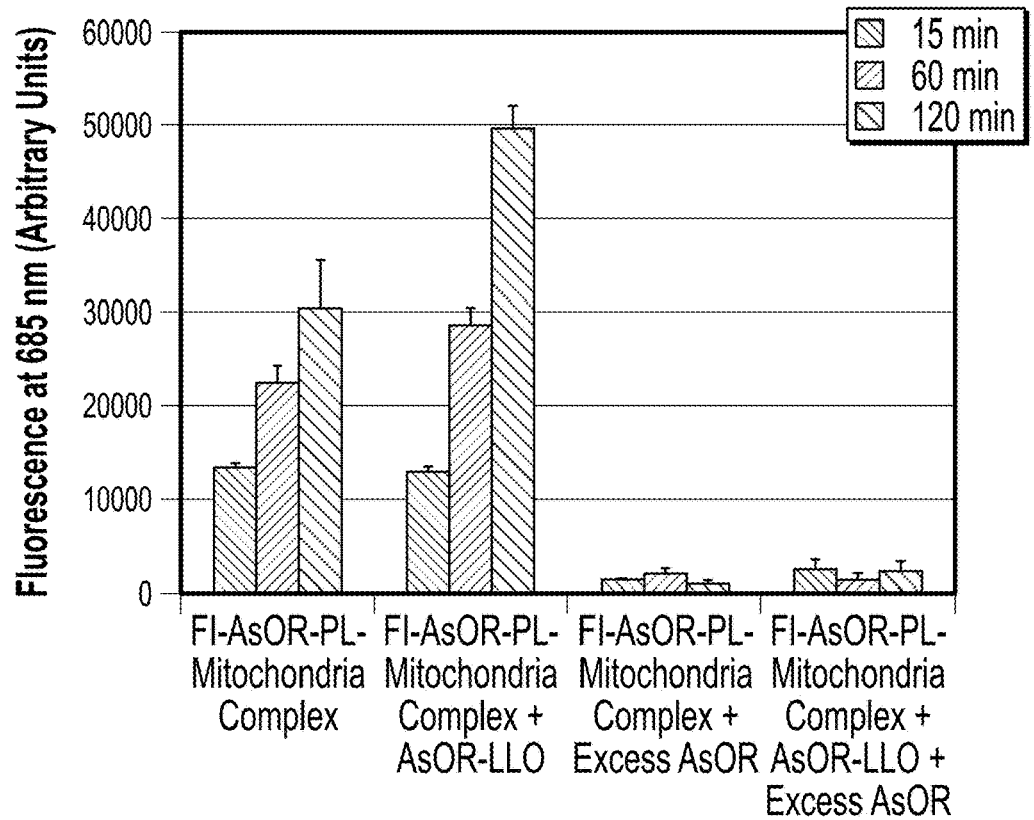
FIG. 14A, fluorescence levels in Huh 7 cells.
Figure 14B:
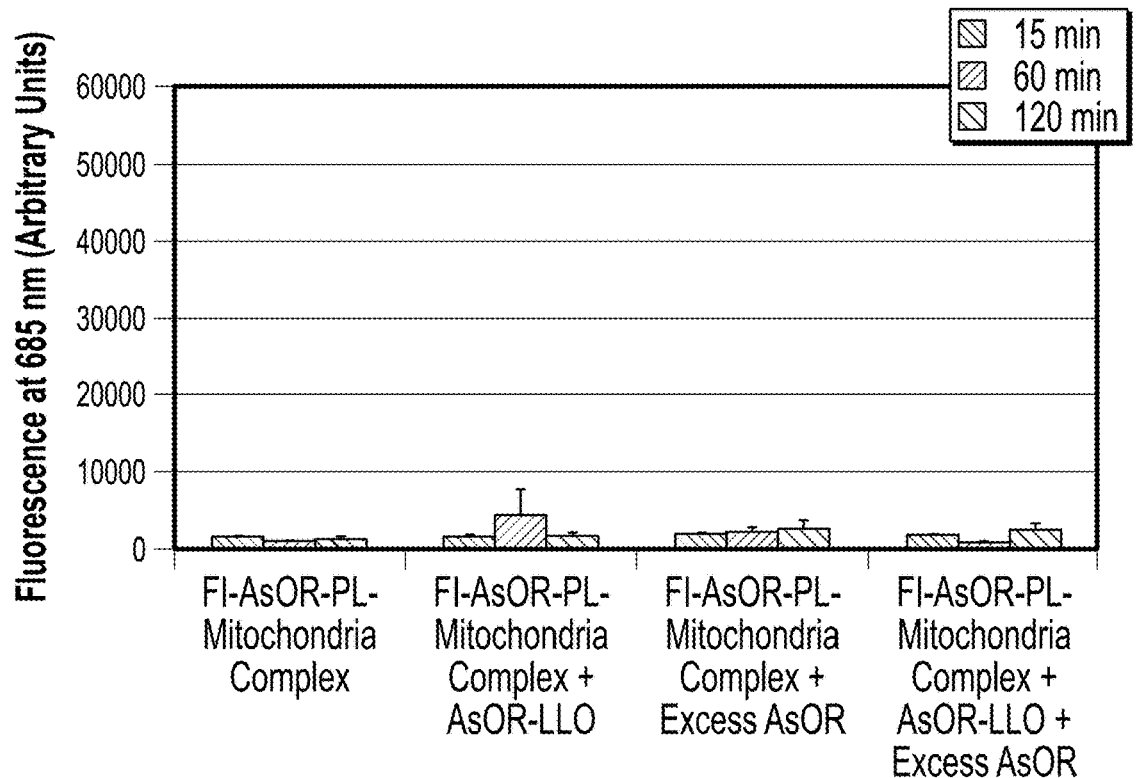
FIG. 14B, SK Hep 1 cells incubated with complexed mitochondria or controls. Mitochondrial DNA levels after incubation of AsOR-LLO conjugate with FIG. 14C, Huh 7 cells.
Figure 14C:
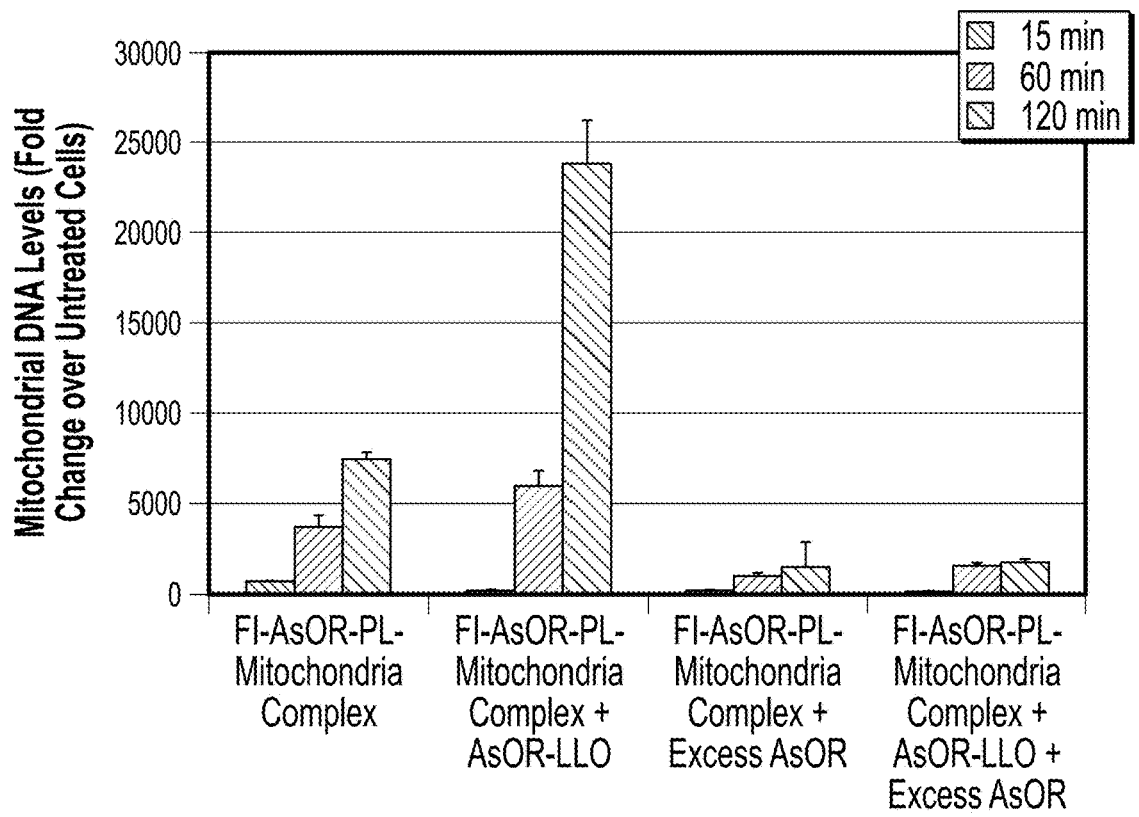
FIG. 14. Uptake of Fl-AsOR-PL-mitochondria complexes by Huh 7 and SK Hep1 cells in presence of AsOR-LLO conjugate as measured by fluorescence and qPCR. Cells were incubated separately with Fl-AsOR-PL-mitochondria complex, complexed mitochondria and AsOR-LLO, complexed mitochondria+excess AsOR or complexed mitochondria+AsOR-LLO+excess AsOR for 2 h and collected for analysis at various time points.
FIG. 14D, SK Hep1 cells.
FIG. 14E, Huh7 cells treated with colchicine.
FIG. 14F, incubated at 4° C.
Figure 14D:
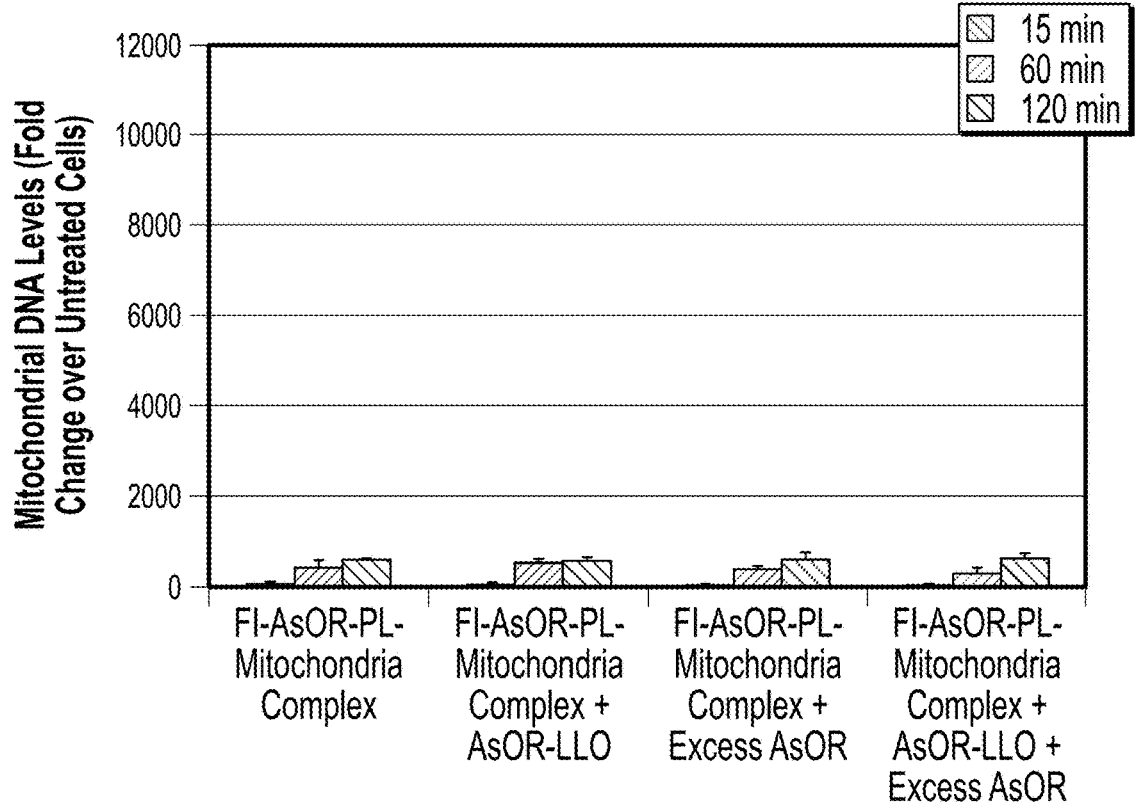
Figure 14E:
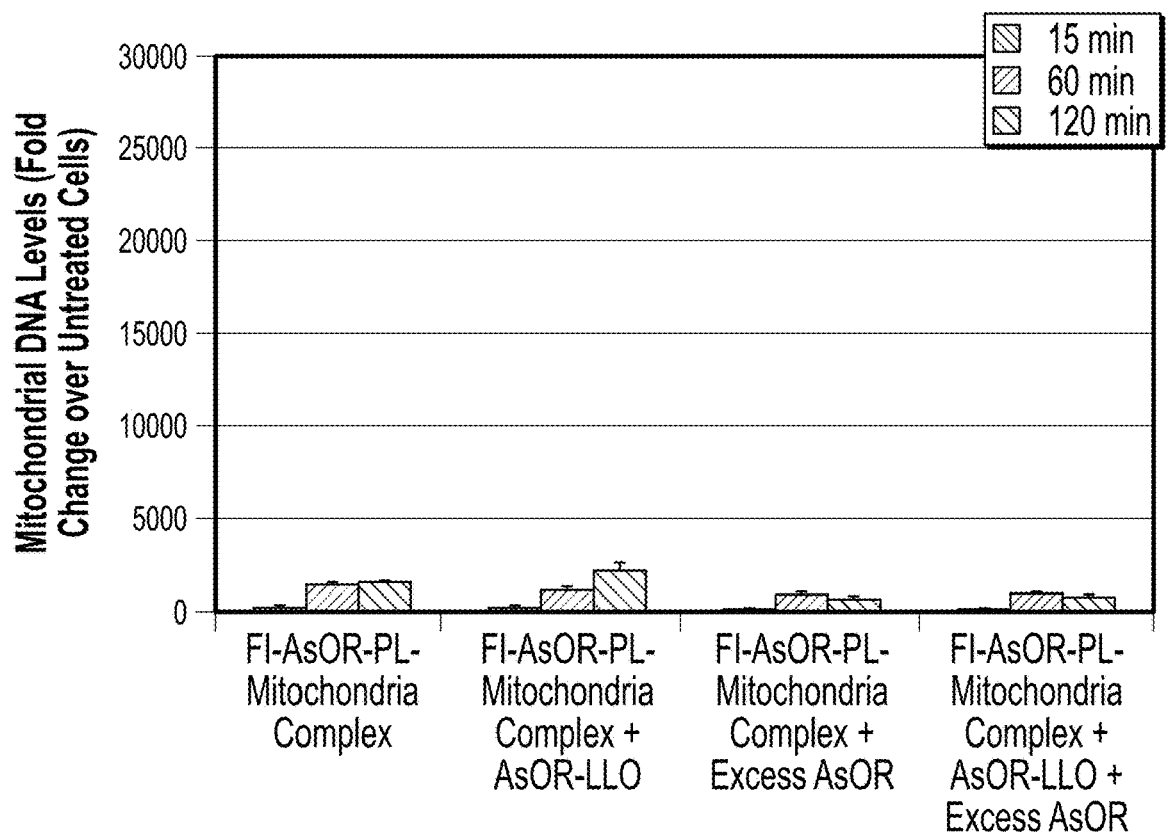
Figure 14F:
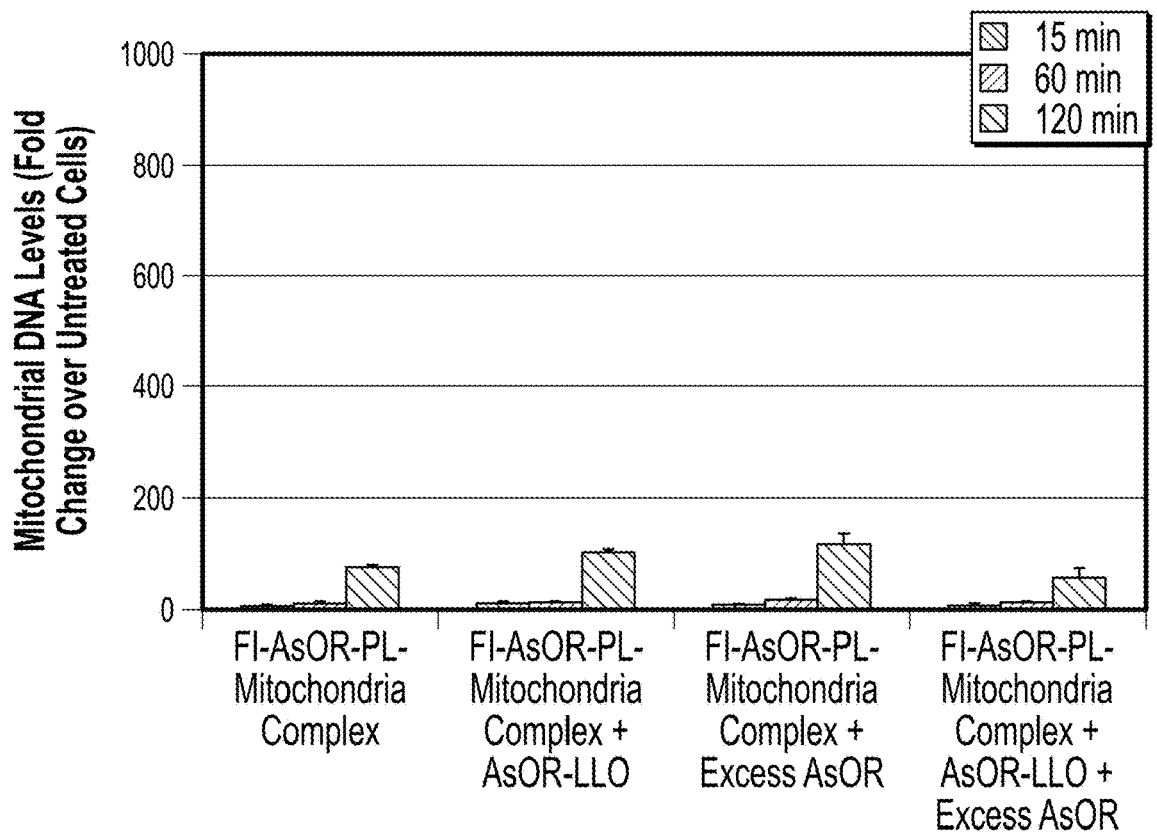

To determine if AsOR-LLO conjugate could enhance delivery of mitochondria to hepatocytes, AsOR-LLO conjugate was mixed with AsOR-PL-mitochondria complex, and incubated with Huh7 and SK HEP1 cells at 37° C. Rat mitochondrial DNA levels were measured by real time PCR as a function of time. FIG. 14C shows that mitochondrial DNA levels in Huh7 cells exposed to mitochondrial complex alone increased from 4,000 at 1 h to 7,000 at 2 h. Mixing AsOR-LLO with complexed mitochondria increased mitochondrial DNA from 6,000 at 1 h to 24,000 at 2 h. There were no significant HTC mitochondrial DNA levels in Huh7 cells when a large molar excess of AsOR was added to compete with complexed mitochondria for uptake. FIG. 14D shows that there were also no significant levels of HTC mitochondrial DNA in SK Hep1 cells incubated with complexed mitochondria at 37° C. Uptake by endocytosis is known to cease at 0° C., and in the presence of an alkaloid, colchicine. Huh7 cells at 0° C., FIG. 14E, and colchicine-treated Huh7 cells, FIG. 14F, did not have significant levels of mitochondrial DNA.

Conclusions: Mitochondria in the form of AsOR-PL complexes can be taken up specifically by AsG receptors on Huh7 cells, and that uptake can be enhanced at least 4-fold when mixed with AsOR-LLO conjugate. Lack of uptake at 0° C. and in the presence of colchicine support the conclusion that the uptake was receptor-mediated.

HTC Mito-GFP Cell Line

Figure 15:
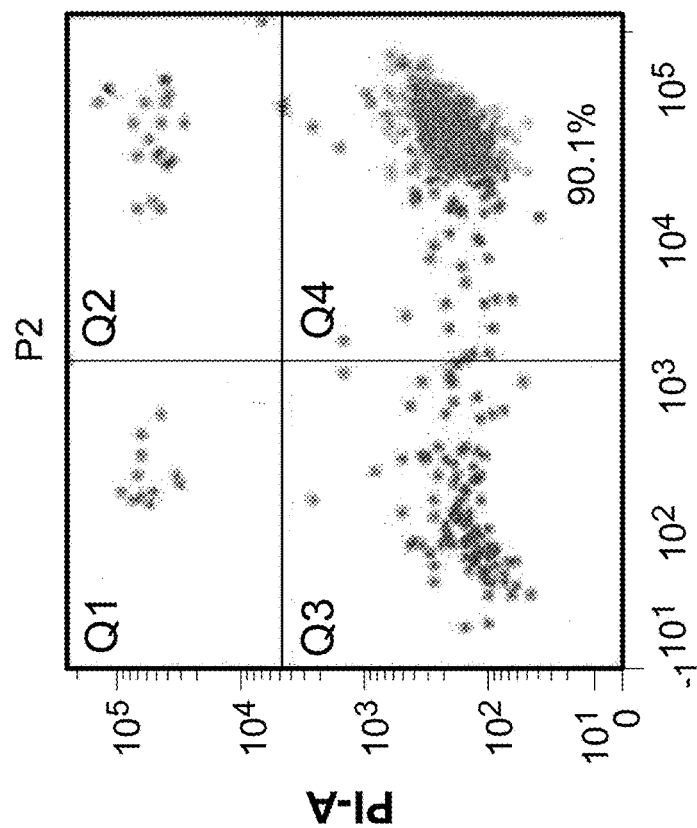
FIG. 15. Fluorescence-activated cell sorting (FACS) of GFP-labeled mitochondria. HTC cells stably expressing GFP-labelled mitochondria were sorted to isolate a stable mito-GFP cell line and kept in G418 media for selection.
Figure 15:
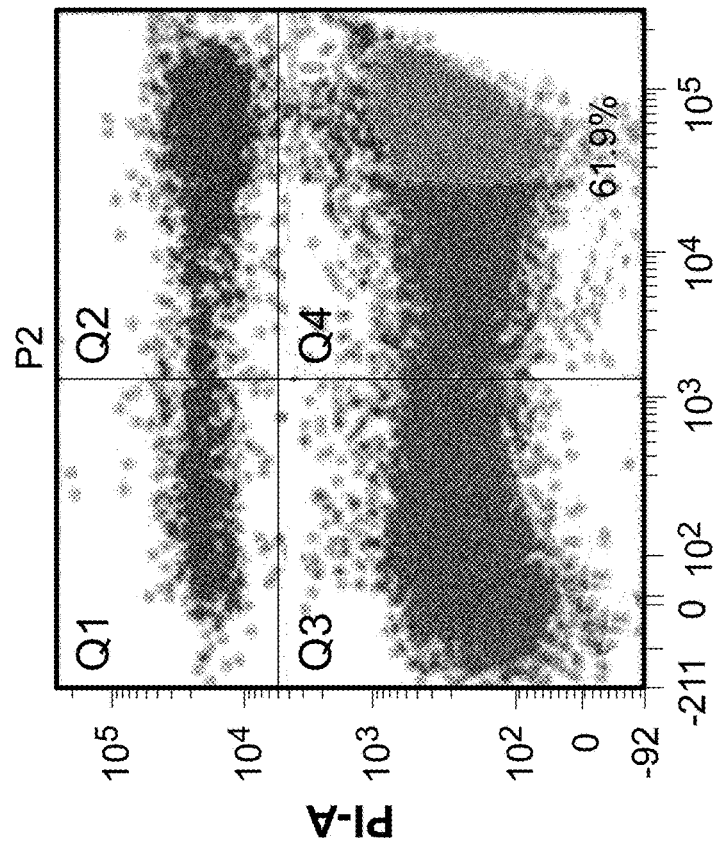

To verify that mitochondrial complexes were truly entering cells and not simply adhering to the cell surface, confocal microscopy was used to examine the location of mitochondria in Z-stack slices through cells. To facilitate this study, an HTC cell line was developed, HTC mito-GFP, which stably expresses GFP in its mitochondria under antibiotic selection pressure. Fluorescence-activated cell sorting (FACS) was used to identify and sort the fluorescent cells. As shown in FIG. 15, FACS was able to isolate fluorescent cells.

Intracellular Localization of Targeted Mito-GFP Mitochondria

Figure 16:
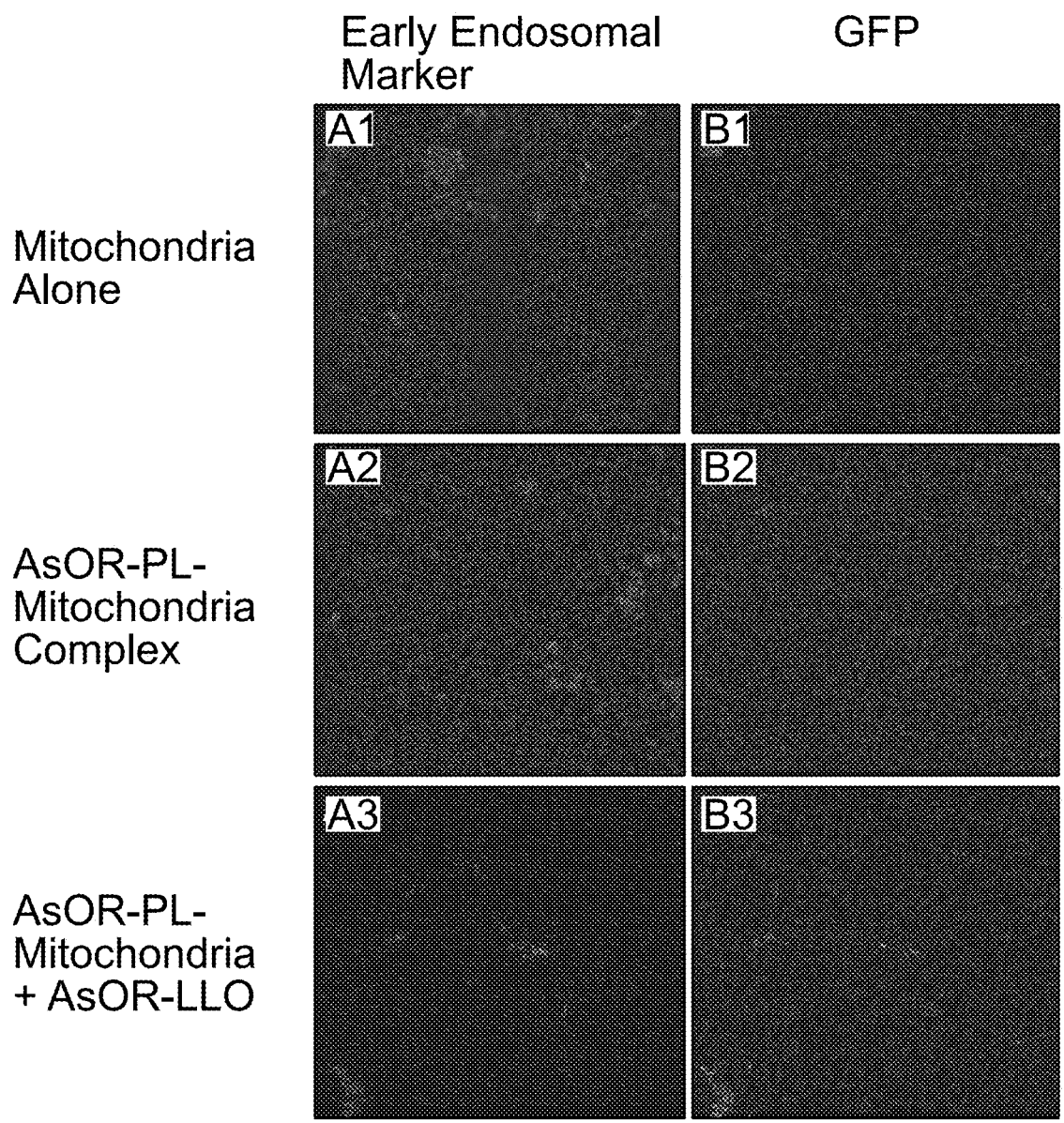
FIG. 16. Confocal microscopic localization of various forms of mitochondria-GFP incubated with Huh7 cells at 37° C. for 2 h, then incubated in media without additives for 6 h. Cells were stained with DAPI for nuclei, and EEA1-Alexa 594, an early endosomal marker, and viewed by confocal microscopy.
Figure 17:
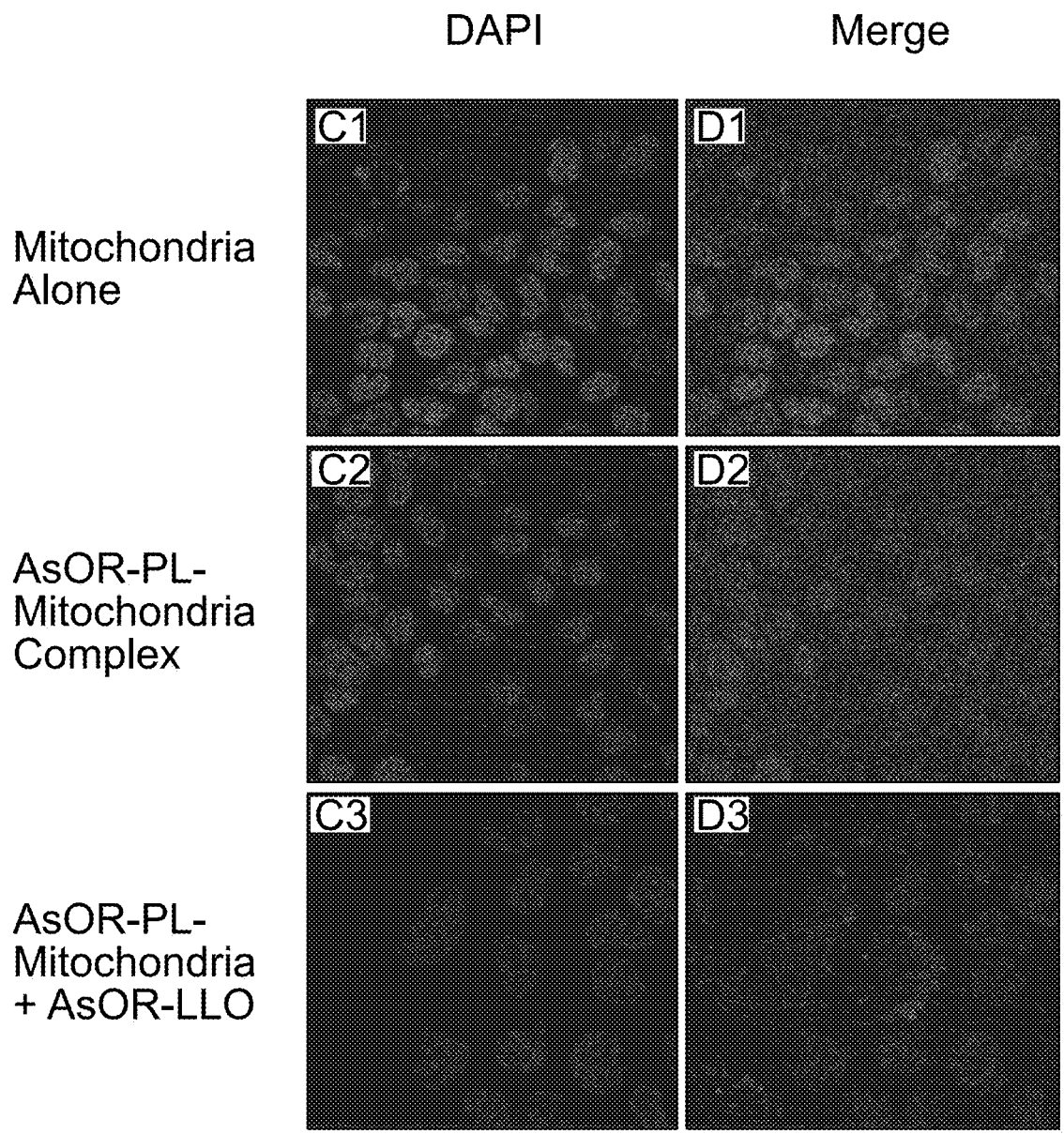
FIG. 17. Confocal microscopic localization of various forms of mitochondria-GFP incubated with Huh7 cells at 37° C. for 2 h, then incubated in media without additives for 6 h. Cells were stained with DAPI for nuclei, and an early endosomal marker, EEA1-Alexa 594.

HTC Mito-GFP, was used as the source of mitochondria for uptake experiments. Huh 7 cells were incubated with complexes and controls for 120 min, washed with EDTA-PBS, and maintained in DMEM 10% FBS. Six h later, cells were stained with an early endosomal marker (EEA1-Alexa Fluor 594). Huh 7 cells incubated with GFP-labeled HTC mitochondria alone showed endosomal (red) staining, FIG. 16A1, but no GFP staining, FIG. 16B1. Cells incubated with AsOR-PL-mitochondria complex showed endosomal staining, FIG. 16A2, and some GFP fluorescence, FIG. 16B2. Those GFP-stained structures that were present overlapped Alexa Fluor 594 in the merged view, FIG. 17D2, suggesting co-localization of mitochondria and endosomes. Cells incubated with both AsOR-PL-mitochondria complex and AsOR-LLO conjugate also showed endosomal, FIG. 16A3, and considerable GFP staining FIG. 16B3, overlapping Alexa Fluor 594 staining, FIG. 17D3. However, there were also large quantities of non-overlapped GFP surrounding nuclei, FIG. 17D3 in the merged view, suggesting the presence of mitochondria not co-localized with endosomes.

Conclusions: Mitochondria alone incubated with Huh7 cells did not reveal detectable uptake. AsOR-PL mitochondria-complexes incubated with Huh7 cells resulted in co-localization of mitochondria with endosomes. The data confirm that the complexed mitochondria were located in an intracellular compartment.

Figure 21:
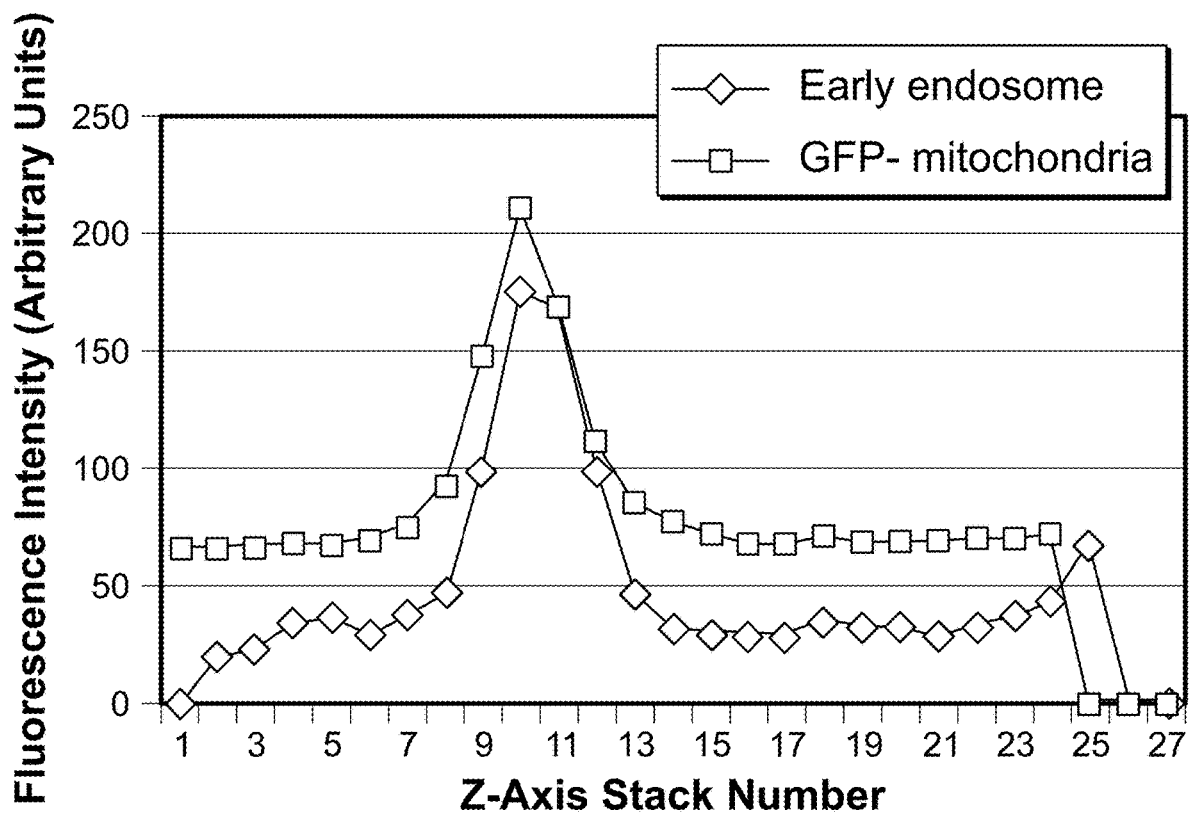
FIG. 21. A plot of fluorescence intensities of confocal microscopic images versus stack number from sample used for FIG. 19. Fluorescence intensities of early endosomal marker EEA1 and GFP-mitochondria were plotted according to depth, stack number, of confocal microscopic images of Huh 7 cells, 6 h post-incubation with AsOR-PL-mitochondria-GFP complexes at 37° C.

If the mitochondria were in endosomes, the peaks of fluorescence should occur at the same location in the cells. By measuring the intensities of two wavelengths of fluorescence as a function of the depth of the plane through the cells, the location of the peaks could be determined as shown in FIG. 21. The mitochondrial and endosomal peak fluorescence both occurred in the same stack, stack 10, supporting the conclusion that the mitochondria and endosomes were co-localized.

Example 3

Figure 9:
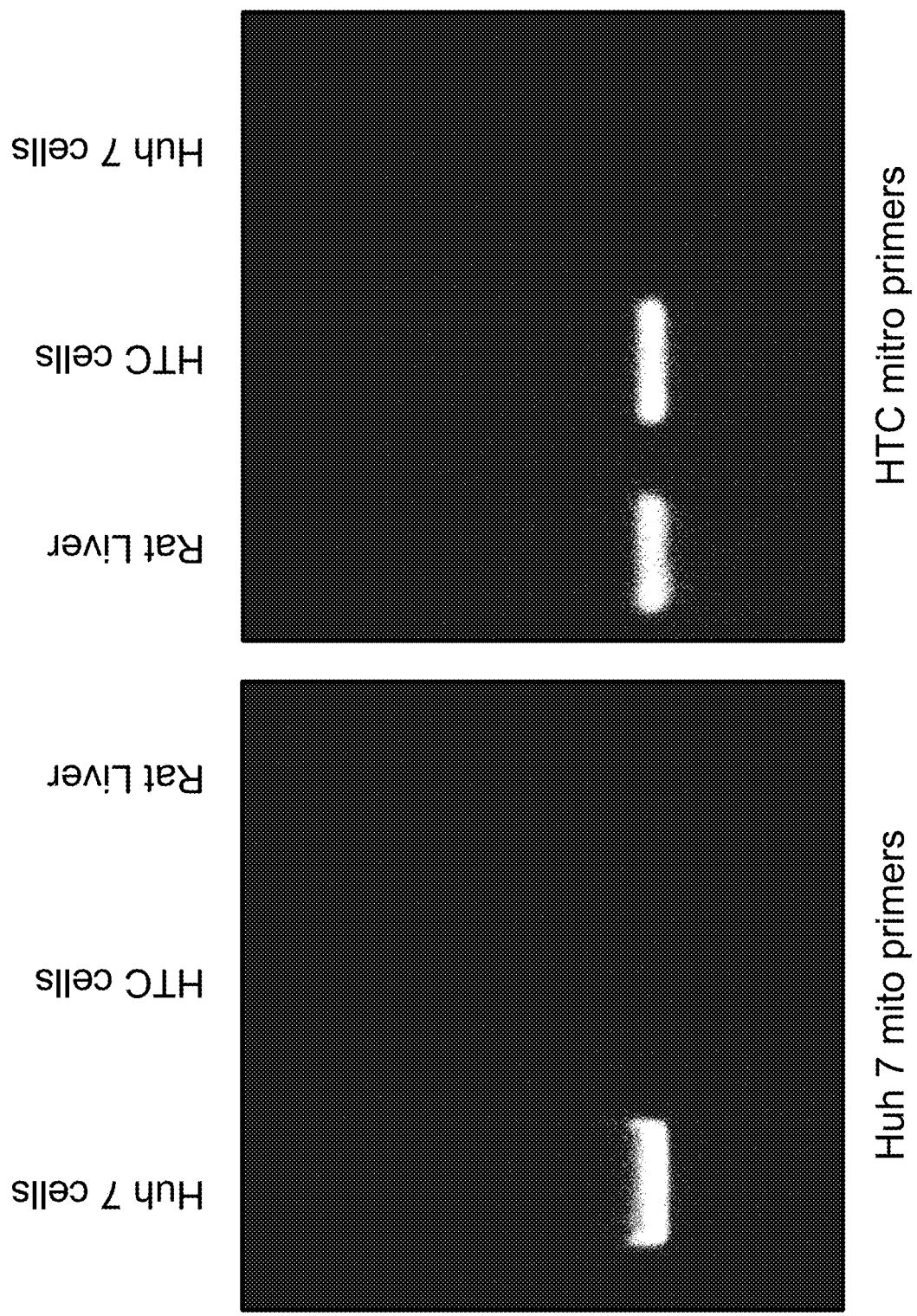
FIG. 9. Primer specificity for mitochondrial DNA by amplification. Primers were designed using Primer 3 and Primer-BLAST to amplify Huh 7 mitochondrial DNA or HTC and rat liver mitochondrial DNA specifically. Huh7 and HTC cell mitochondrial DNA and rat liver cell DNA were used to determine the specificity of primers. PCR amplified products on gels showed that Huh 7 mitochondrial primers, and HTC mitochondrial primers specifically amplified only Huh 7 mitochondrial DNA and HTC (rat) mitochondrial DNA, respectively.

Targeting of Mitochondria to Hepatocytes: Uptake of Mitochondria into Huh-7 Receptor (+) Mito (−) Cells Grown in Supplement-Free Media Primers were designed using Primer 3 and Primer-BLAST to amplify Huh 7 mitochondrial DNA or HTC and rat liver mitochondrial DNA specifically, FIG. 9.

Figure 22:
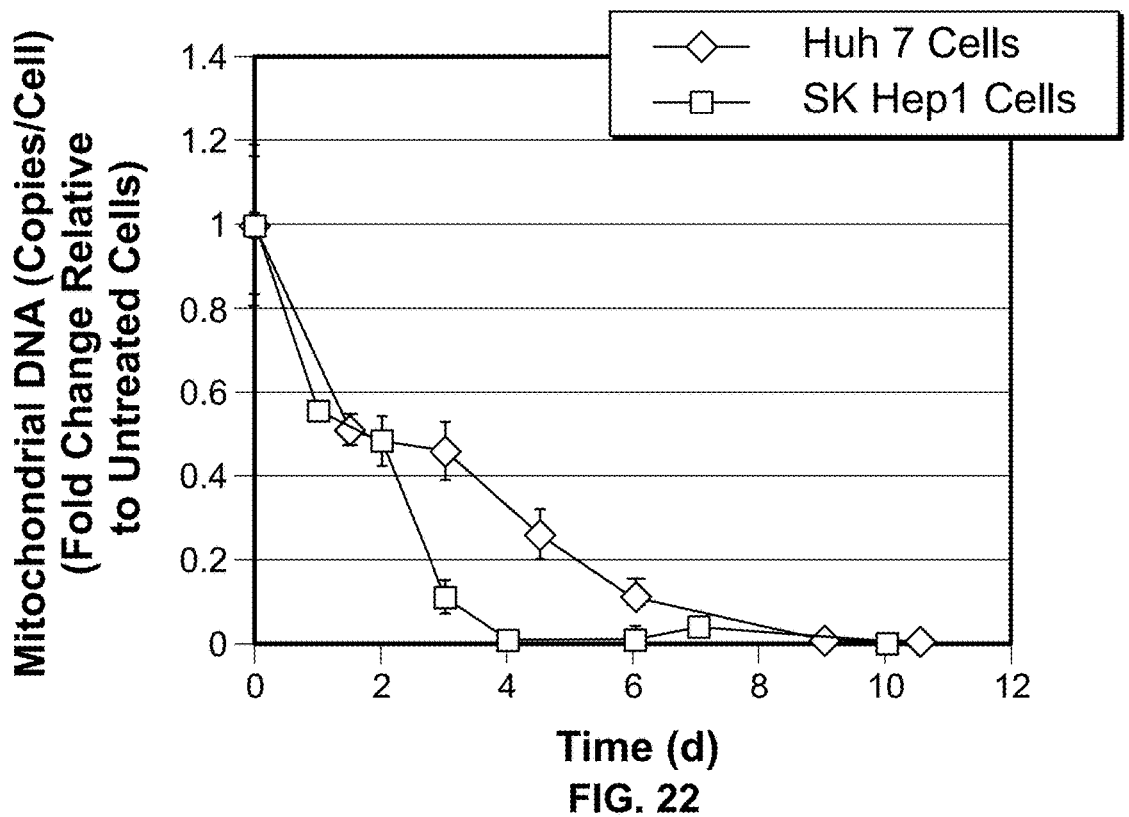
FIG. 22. Mitochondrial DNA levels in Huh 7 and SK Hep1 cells treated with dideoxycytidine (ddC). Huh 7 and SK Hep1 cells were treated with ddC for 3 weeks and mitochondrial DNA levels were determined by qPCR with time.

To create a model of mitochondrial toxicity, Huh 7 and SK Hep1 cells at 20% confluence, were exposed to 10 μM 2',3'-dideoxycytidine (ddC) (Sigma-Aldrich) for 3 weeks. Mitochondrial DNA levels determined by qPCR decreased steadily with time, FIG. 22. Cells lacking detectable mitochondria were propagated in supplemental media, and used as a model for mitochondrial transplantation in which there was no background host mitochondrial DNA.

An asialoglycoprotein, AsOR, was linked to polylysine to create a conjugate AsOR-PL, and complexed with healthy mitochondria. Huh 7 [AsGR (+)] and SK Hep1 [AsGR (−)] cells were treated with a mitochondrial toxin to form Huh 7-Mito (−) and SK Hep1-Mito (−) cells, lacking detectable mitochondrial DNA. An endosomolytic peptide, LLO, was coupled to AsOR to form AsOR-LLO. Co-incubation of complexed mitochondria and AsOR-LLO with Huh7-mito (−) cells increased mitochondrial DNA to >9,700-fold over control at 7 d (p<0.001), and increased mitochondrial oxygen consumption rates to >90% of control by 10 d.

Rescue of mitochondria-damaged hepatocytes can be achieved by targeted uptake of normal mitochondria through receptor-mediated endocytosis.

Figure 25A:
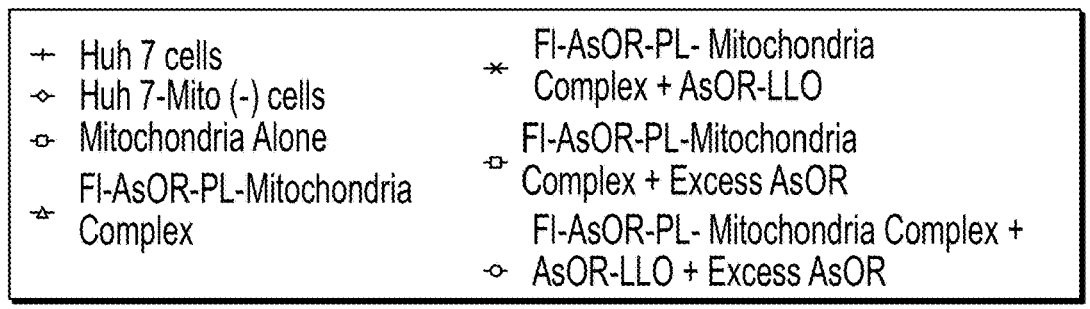
FIG. 25A, Huh 7-Mito (−) cells.
Figure 25A:
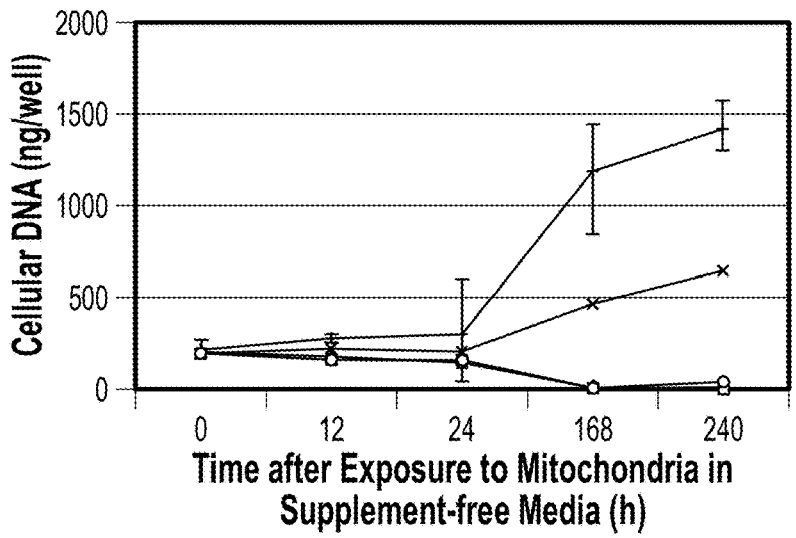
Figure 25B:
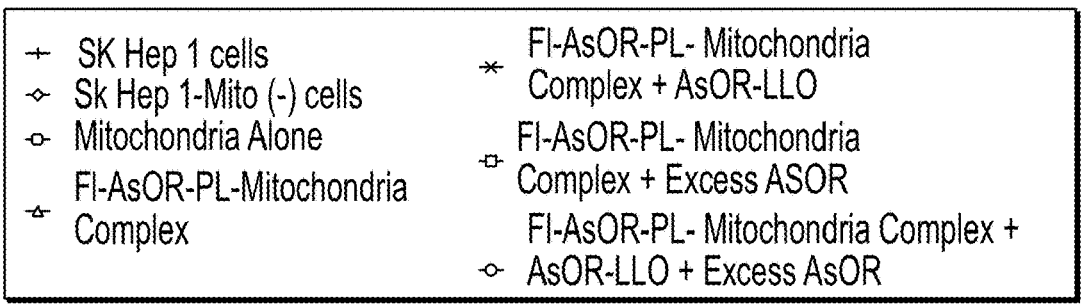
FIG. 25B, SK Hep1-Mito (−) cells. Total cellular DNA in cells after incubation with mitochondria alone, Fl-AsOR-PL-mitochondria complex, complexed mitochondria plus AsOR-LLO conjugate, complexed mitochondria plus excess AsOR or complexed mitochondria plus AsOR-LLO conjugates plus excess AsOR at 37° C. Cellular DNA levels were measured a function of time in supplement-free media as an estimate of the numbers of cells present.
Figure 25B:
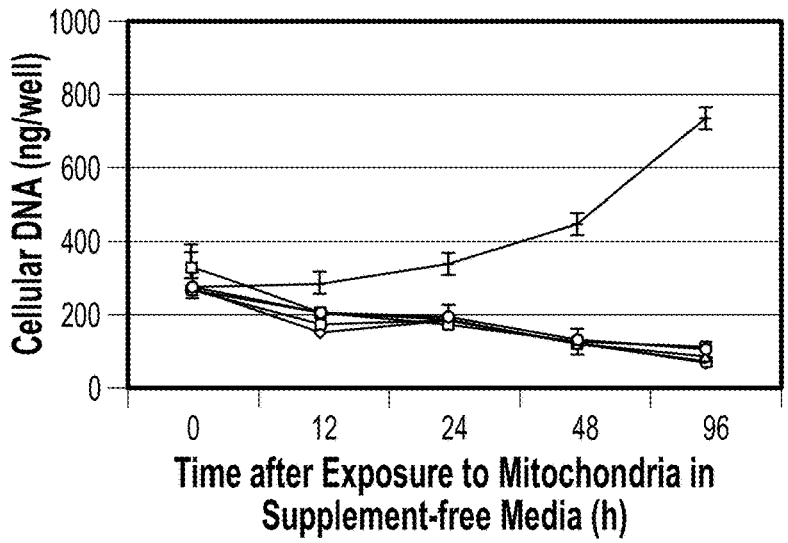

Huh 7-Mito (−) and SK Hep1-Mito (−) cells lacking mitochondrial DNA were used as models of cells with mitochondrial damage. These cells require supplemental media to survive. Exposure of Huh7 AsGR (+) cells to Fl-AsOR-PL-mitochondria plus targetable endosomolytic agent, AsOR-LLO, increased fluorescence and mitochondrial DNA levels in cells, but not controls, FIG. 23A-F. Exposure of Huh7 AsGR (+) cells to Fl-AsOR-PL-mitochondria plus targetable endosomolytic agent, AsOR-LLO, rescued Huh7 Mito (−) cells, resulting in proliferation in supplement-free medium, FIG. 25A. The content and ratio of mitochondrial DNA per cell rose rapidly after exposure and remained constant, but not in controls. Rescue was not observed in SK Hep1 Mito (−) cells, FIG. 25B.

Experimental Procedures

Protein Preparation

Orosomucoid (OR) was isolated from human serum (American Red Cross) as described previously (Whitehead P H, Sammons H G. *Biochim Biophys Acta* 1966; 124:209-211). OR was de-sialylated with neuraminidase (Sigma-Aldrich, St. Louis, Mo., USA) (12) to make asialoorosomucoid (AsOR), and labeled with dylight 650, a fluorescent label, using an NHS ester reaction (Thermo Fisher Scientific Inc., Rockford, Ill. USA) according to manufacturer's instructions. AsOR and fluorescence-labeled AsOR (Fl-AsOR) were separately reacted with a carbodiimide cross-linker (Sigma-Aldrich, St. Louis, Mo., USA) followed by addition of poly L-lysine (PL) (Sigma-Aldrich, St. Louis, Mo., USA) in 1 ml of 0.1 M 2-(N-morpholino)ethanesulfonic acid (MES), pH 6, for 24 h at 25° C. Excess PL was removed using an exclusion column (10,000 MWCO) (EMD Millipore, Billerica, Mass., USA). Fluorescence intensities of Fl-AsOR and Fl-AsOR-PL, 1 µg each in 100 µl in phosphate-buffered saline (PBS), were measured by an XFLUOR4SAFIREII Version: V 4.62n spectrophotometer.

Mass Spectrometry

AsOR, Fl-AsOR and Fl-AsOR-PL were diluted to 1, 0.1, 0.025 and 0.001 mg/ml, respectively. Matrix, 3, 5-dimethoxy-4-hydroxycinnamic acid (sinapinic acid), (Sequazym Peptide Mass Standards Kit, Applied Biosystems, Thermo Fisher Scientific, Rockford, Ill., USA) was mixed with various concentrations of proteins with or without controls according to manufacturer's instructions, and submitted for mass spectrophotometry (Voyager-MALDI)

Preparation and Purification of Mitochondria

Mitochondria were isolated from HTC or Huh 7 cells using a mitochondria isolation kit for mammalian cells (Thermo Fisher Scientific, Waltham, Mass.) according to manufacturer's instructions. The mitochondrial pellets were washed with, and kept in isolation kit reagent C on ice until further use.

Preparation and Stability of Fl-AsOR-PL-Mitochondria Complexes

Rat (HTC) cell mitochondria, 800 µl (1.6 µg/µl total mitochondrial protein) were incubated with 100 µg of Fl-AsOR-PL or Fl-AsOR protein (in 52 µl PBS) on ice for 45 min. Samples were repeatedly spun at 4000 rpm for 8-10 min at 4° C., and re-suspended in mitochondria isolation kit reagent C (Thermo Fisher Scientific, Waltham, Mass.). After each spin, the mitochondrial pellets and supernatants were collected, and fluorescence measured at 685 nm. Experiments were conducted in triplicate, and repeated 3 times. The results were expressed as mean±standard error of arbitrary fluorescence units per equal numbers of cells.

Preparation of Listeriolysin

Listeriolysin 0 (LLO) was purified from *L. monocytogenes*, (D. A. Portnoy, Stanford University), as described previously (Walton C M, Wu C H, Wu G Y. *Protein Expr Purif* 1999; 15:243-245) except that supernatants were concentrated using centrifugal devices (EMD Millipore Centricon® Plus-70 Centrifugal Filter Units, membrane NMWL 30,000), washed with 3 liter (L) ice-cold distilled water, and concentrated to 400-600 ml. Supernatants were passed through a DEAE-Sephacel column, and purified LLO was washed, and then desalted with PD-10 columns (Sephadex G-25 M, Pharmacia Biotech). Purified LLO stored at −20° C. until further use. AsOR-LLO conjugates were synthesized using an SPDP crosslinker (Thermo Fisher Scientific) according to manufacturer's instructions. LLO-SPDP was reduced with DTT, and separated from excess DTT with a PD-10 column equilibrated with PBS. Reduced LLO-SPDP was mixed with AsOR-SPDP, and incubated for 18 h at 4° C. to form AsOR-LLO conjugate. Final concentrations of proteins were measured using a Bio-Rad protein assay (BIO RAD) according to manufacturer's instructions. Purity and size of proteins was determined by 10% SDS-PAGE.

Hemolysis Assay

To measure hemolytic activity, varying concentrations of LLO and AsOR-LLO conjugate were incubated with or without DTT, and approximately 5 million human RBCs in 10 µl at pH 7.4 or 5.6 for 30 min at 37° C. Effects of cholesterol on hemolytic activity was determined as described previously (Jacobs T et al., Mol Microbiol 1998; 28:1081-1089). The amounts of protein required for 50% hemolysis (CH50) were calculated (Costabile M. J Vis Exp 2010 Mar. 29; (37). pii: 1923. doi: 10.3791/1923.). Assays were performed in 4 independent replicates, and the results are expressed as percent relative to hemolysis of RBCs in distilled water.

Cell Culture

Human hepatocellular carcinoma cells, Huh 7 AsGR (+), SK Hep1 cells AsGR (−), and rat HTC cells were maintained in Dulbecco's Modified Eagle Medium (DMEM) (Gibco) supplemented with antibiotic/antimycotic solution (Invitrogen), 10% fetal bovine serum (FBS) (Invitrogen) (Choi J et al., *Hepatology* 2004; 39:81-89). To create GFP-labeled mitochondria, HTC cells were transfected with pAcGFP1-Mito plasmid (Clontech Laboratories) using lipofectamine (Life Technologies) according to manufacturer's instructions. pAcGFP1-mito plasmid encodes a mitochondrial targeting sequence (derived from the precursor of subunit VIII of human cytochrome C oxidase) fused to the N-terminus of green fluorescent protein (GFP) from *Aequorea coerulescens* (AcGFP). Fluorescence-activated cell sorting (FACS) was used to separate GFP-labeled cells. HTC GFP cells were maintained in DMEM supplemented with antibiotic/antimycotic solution, 10% FBS and 1.5 mg/ml G418 (Calbiochem). GFP labeling was determined using MitoTracker RED FM (Molecular Probes—Life Technologies) according to the manufacturer's instructions. In brief, 200 nM MitoTracker red probe in Opti-MEM I medium (Invitrogen) was incubated with HTC mito-GFP cells. Cells were washed with PBS, fixed with 4% paraformaldehyde and with PBS.

Labeled cells were mounted in ProLong® Gold reagent (Life Technologies) and used for fluorescent microscope imaging.

Preparation of Mito (−) Cells

To create a model of mitochondrial toxicity, Huh 7 and SK Hep1 cells at 20% confluence, were exposed to 10 µM 2',3'-dideoxycytidine (ddC) (Sigma-Aldrich) for 3 weeks (Chariot P, Drogou I et al., *J Hepatol* 1999; 30:156-160). Cells were maintained in DMEM supplemented with antibiotic/antimycotic solution, 10% dialyzed FBS, 2 mM L-glutamine, 100 mg/ml sodium pyruvate (Thermo Fisher Scientific), and 50 mg/ml uridine (Sigma-Aldrich) (Hashiguchi K, Zhang-Akiyama QM. Methods Mol Biol 2009; 554:383-391). Mitochondrial DNA levels were determined by qPCR at various time points, and cells lacking detectable mitochondrial DNA were designated Mito (−). Huh 7-Mito (−) and SK Hep1-Mito (−) cells were frozen at −80° C. until needed.

AsGR Uptake Assay

Cells were plated at 50% confluence on tissue culture plates or sterile cover slips 2-3 days before assay. When 95% confluent, cells were washed with PBS (Mg2+- and Ca2+-free) and maintained in phosphate-free DMEM with high glucose (Thermo Fisher Scientific) for 16 h. Mitochondria were isolated from donor cells (HTC or Huh7 or HTC mito-GFP cells) using a mitochondria isolation kit for mammalian cells (Thermo Fisher Scientific) according to manufacturer's instructions, and kept on ice in mitochondria isolation kit Reagent C. Uptake assays were conducted at 37° C. or 4° C. in DMEM, 2.8 mM Ca2+(Hui E et al., *Cell* 2009; 138:709-721) to which was added either 20 µg/ml mitochondria alone, 4 µg/ml Fl-AsOR-PL alone, 25 µl/ml Fl-AsOR-PL-mitochondria complex, 25 µl/ml Fl-AsOR-PL-mitochondria complex+0.15 µg/ml AsOR-LLO conjugate, 25 µl/ml Fl-AsOR-PL-mitochondria complex+200 µg/ml AsOR (100-fold molar excess added 4 min prior to uptake) or 25 µl/ml Fl-AsOR-PL-mitochondria complex+0.15 µg/ml AsOR-LLO conjugate+200 µg/ml AsOR (100-fold molar excess added 4 min prior to uptake). Cells were washed 3 times with 10 mM EDTA in ice-cold PBS (Mg2+ and Ca2+ free) followed by ice-cold PBS at each time point or at 2 h for extended experiments. Cells were either trypsinized with 0.05% trypsin-EDTA (Thermo Fisher Scientific) and collected by centrifugation at 800 rpm for 4 min at 4° C. or lysed with 200 µl lysis buffer (Buffer A, mitochondria isolation kit, Thermo Fisher Scientific). Fluorescence intensity of Fl-AsOR-PL in lysed cells was measured using XFLUOR4SAFIREII Version: V 4.62n spectrophotometer. Trypsinized cells or cell lysates were used to determine and quantitate donor mitochondrial DNA levels by qPCR. Experiments were conducted in triplicate, and repeated at least 3 times, and the means±standard error were expressed as arbitrary fluorescence units per equal numbers of cells.

Inhibitors of Endocytosis

To determine the effects of colchicine, cells were incubated with colchicine 1 µM for 2 h prior to uptake and during the uptake assay (Piasek A, Thyberg J. *J Cell Biol* 1979; 81:426-437). To determine the effects of low temperature, uptake studies were performed at 4° C. using ice-cold phosphate- and bicarbonate-free DMEM.

Quantitative PCR (qPCR)

To measure uptake of mitochondria, primers (Table 1) were designed to distinguish donor from host cell mitochondria using Primer3 (Untergasser A et al., a, al, *Nucleic Acids Res* 2012; 40:e115) and Primer-BLAST (Ye J et al., *BMC Bioinformatics* 2012; 13:134) and specifically amplifying human Huh 7 mitochondrial DNA or rat liver (HTC) mitochondrial DNA. Primer specificity was determined by PCR using DNA extracted from Huh 7 cells and HTC cells with QIAamp DNA mini kit (Qiagen, Valencia, Calif.) according to the manufacturer's instructions.

Quantitation of Mitochondrial and Nuclear DNA by qPCR

For uptake studies, whole cell DNA was isolated using QIAamp DNA mini kit (Qiagen) and mitochondrial DNA levels were quantified by qPCR with Power SYBR Green PCR Master Mix (Applied Biosystems, Thermo Fisher Scientific) according to manufacturer's instructions. Human lactate dehydrogenase A (LDHA) DNA levels were quantified using human LDHA specific primers, and the results used to normalize mitochondrial DNA levels (Table 1). The qPCR conditions were: one cycle of 2 min at 50° C., and 10 min at 95° C.; 40 cycles of 15 sec at 95° C., and 1 min at 60° C. followed by one cycle of 10 min at 55° C. Melt curves were obtained following each qPCR, and the specificity of the reaction analyzed under the following conditions: 15 sec at 95° C., 15 sec at 60° C. and 15 sec at 95° C. Assays were repeated with 3 independent replicates, and the results expressed as means±standard error as fold change of mitochondrial DNA levels in cells compared to untreated controls, and estimates of mitochondrial DNA copies per cell.

Cell Proliferation Assay

Cells were maintained in DMEM supplemented with antibiotic/antimycotic solution, 1% dialyzed FBS after uptake for 2 h. DNA levels were determined at each time point with CyQUANT Cell proliferation assay kit (Molecular Probes, Thermo Fisher Scientific) according to manufacturer's instructions. Experiments were conducted in triplicate, and repeated twice. Results were expressed as mean±standard error of arbitrary fluorescence intensity units per equal numbers of cells.

Confocal Microscopy

AsOR-PL-Mito-GFP complex, Mito-GFP, and AsOR-PL-Mito-GFP complex+AsOR-LLO conjugate was incubated separately with cells for 2 h at 37° C. Cells were washed with EDTA-PBS and maintained in DMEM supplemented with antibiotic/antimycotic solution, and 10% FBS for 6 h. Cells were fixed with 4% paraformaldehyde for 30 min, and permeabilized with 0.25% Triton X-100 (Sigma-Aldrich) in PBS for 10 min followed by blocking solution (1% goat serum, 5% BSA, 0.3 M glycine) for 1 h at 25° C. Cells were incubated with anti-EEA1 antibody [1G11] (early endosome marker) (Abcam Inc, Cambridge, Mass., USA) overnight at 4° C. Alexa Fluor 594 goat anti-mouse (Thermo Fisher Scientific) secondary antibody was added for 1 h. Nuclei were stained with DAPI (Thermo Fisher Scientific) for 20 min. Cells were mounted and imaged under confocal microscope, and images were analyzed with Image J. Cells without first antibody served as controls. To determine the localization of endosomes and mitochondria in the Z-plane, four areas were randomly selected on the images taken by confocal microscopy, and GFP and Alexa Fluor 594 intensities were measured from each slice of Z-stacks of the image. Intensities were plotted against slice numbers. High fluorescence intensity of both GFP and Alexa Fluor 594 in close proximity was taken to represent co-localization of HTC mitochondria and early endosomes in the Z-plane.

After uptake of Fl-AsOR-PL for 1 h at 37° C., cells were fixed with 4% paraformaldehyde for 10 min, and stained with DAPI for 20 min. Cells were mounted and imaged under a fluorescence microscope, and presented as single wavelength, and merged wavelength images.

Mitochondria Respiration Assay

Cells were plated in XF24 cell culture microplates (Seahorse Bioscience, North Billerica, Mass.) 2 days before uptake assays. Complexed mitochondria and controls were incubated with cells for 2 h. Cells were washed and maintained in DMEM supplemented with antibiotic/antimycotic solution, 1% dialyzed FBS for respiration assays performed using an XF Cell Mito Stress Kit (Seahorse Bioscience, North Billerica, Mass.) at various time points according to manufacturer's instructions. Oxygen consumption rates (OCR) per well normalized to DNA levels were determined. Assays were performed in triplicate, and results were expressed as mean±standard error of OCR per group in units of pmol/min/DNA level at each time point.

Results

Asialoglycoprotein Conjugate Binding to Mitochondria

Asialo-orosomucoid (AsOR) was fluorescently labeled (Fl-AsOR), and covalently linked to poly-L-lysine (PL) creating Fl-AsOR-PL. After purification, AsOR, and AsOR-PL were shown to be fluorescently labeled FIG. 3. Mass spectrometric data showed that an average of two fluorescent tags, and two PL chains were bound per Fl-AsOR-PL molecule, FIG. 4. An agarose gel showed that AsOR and Fl-AsOR were negatively charged. However, Fl-AsOR-PL was positively charged, FIG. 5.

Conclusions: Covalent linkage of a polycation such as polylysine can convert a negatively charged glycoprotein such a as AsOR into a positively charged one.

To test whether chemical linkage of PL to AsOR might have altered AsOR recognition by AsG receptors, binding of AsOR-PL to AsG receptors was studied using [AsG receptor (+)], SK Hep1 [AsG receptor (−)] cells. Fl-AsOR-PL was incubated with cells for 1 hour (h) at 37° C., and fluorescence microscopy was performed. DAPI was used to stain nuclei a different color (green) compared to that of AsOR (red). Huh7 [AsG receptor (+)] cells incubated with Fl-AsOR-PL resulted in numerous small punctate red structures, FIG. 6 upper left panel. Some structures surrounded nuclei shown in the lower panel indicating that those structures were intracellular, and the size suggested endosomal vesicles, FIG. 6 lower left panel. In contrast, SK Hep1 cells [AsG receptor (−)] lacked any detectable small punctate red structures, FIG. 6 upper and lower right panels.

Conclusions: The punctate pattern is consistent with entry of AsOR-PL into endosomes. Fluorescence appeared only in Huh7 [AsG receptor (+)], but not SK Hep1 cells [AsG receptor (−)] which is consistent with uptake of the former by AsG receptors.

Isolated HTC (rat) mitochondria were mixed with Fl-AsOR-PL to form complexes. The stability of the Fl-AsOR-PL-mitochondria complexes was determined by repeated centrifugation and re-suspension of the complexes in fresh medium. As shown in FIG. 1A, fluorescence of the Fl-AsOR-PL associated with the pelleted mitochondria, decreased by about 15% after the second spin, and then remained constant at approximately 27,000 units through three spins. In contrast, the mitochondria pellet-associated fluorescence after mixing of mitochondria with Fl-AsOR (lacking PL) was significantly less, 4,000 units. The supernatant contained >90% of fluorescence of the Fl-AsOR alone after the first spin, but was no longer detected in pelleted mitochondria after the 2nd and 3rd spins, FIG. 7A. Fluorescence in the supernatants of Fl-AsOR-PL mixed with mitochondria decreased to 24% from 32000 to 7900 units in supernatant after 1st spin, and remained low in subsequent spins, FIG. 7B. Conclusions: These data suggest that Fl-AsOR-PL bound mitochondria, and that the binding was stable under the conditions of re-suspension and centrifugation. Particle size analysis of mitochondria alone revealed a mean diameter of 700±57.8 nm, while purified Fl-AsOR-PL-mitochondrial complexes had a mean diameter 1000±62 nm, FIG. 8. Conclusions: Incubation followed by repeated centrifugation and resuspension resulted in Fl-AsOR-PL-mitochondrial complexes with mean diameters which were about 30% larger than those of mitochondrial alone. The fact that the diameters were not multiples of 700 nm suggests that the increase in size was not due to aggregation of mitochondria.

Targeting of Mitochondria Specifically to Hepatocytes by AsGR

To determine whether complexed mitochondria could be recognized by AsGR, Huh 7 cells and SK Hep1 cells were incubated separately with Fl-AsOR-PL-mitochondria complex, mitochondria alone, Fl-AsOR protein alone or Fl-AsOR-PL-mitochondria complex with an excess AsOR at 37° C. The fluorescence level in Huh 7 AsGR (+) cells, incubated with Fl-AsOR alone was approximately 15,000 units at 15 min, and increased significantly (p<0.001) to more than 20,000 units at 60 min, FIG. 10A. Similarly, fluorescence in Huh 7 cells incubated with Fl-AsOR-PL-mitochondria complex was 20,000 units at 15 min, and increased significantly (p<0.001) to more than 35,000 units at 60 min. As expected, no fluorescence was detected in Huh 7 cells after incubation of mitochondria alone. A large molar excess of AsOR with Fl-AsOR-PL-mitochondria complex decreased fluorescence levels to less than 2,500 units at both 15 min and 60 min in Huh 7 cells, FIG. 2A. Fluorescence in SK Hep1, AsGR (−) cells was barely detectable under all conditions, FIG. 10B. Conclusions: Fluorescence associated with Fl-AsOR-PL-mitochondria complexes increased only in AsGR(+), not AsGR (−) cells. Competition by excess free AsOR supports involvement of the AsGR.

However, because the fluorescent tag was on the Fl-AsOR-PL carrier, it is possible that the carrier alone, without mitochondria, was internalized. To determine whether complexed mitochondria were actually taken up by Huh 7 cells, primers were designed, Table 1, and shown to specifically distinguish rat from Huh 7 (human) mitochondrial DNA, FIG. 9. Huh 7 cells incubated with Fl-AsOR-PL-mitochondria complex resulted in a significant (p<0.004) increase, 990-fold of HTC mitochondrial DNA levels, approximately 6-14 HTC mitochondria per cell, (based on reported copies of mitochondrial DNA per mitochondrion) compared to untreated cells at 15 min, and increased to more than double (approximately 14-36 HTC mitochondria per cell) (p<0.001) at 60 min, FIG. 10C. Huh 7 cells incubated with either mitochondria alone or Fl-AsOR alone had no significant HTC mitochondrial DNA levels. Exposure of Huh 7 cells to Fl-AsOR-PL-mitochondria complex with excess free AsOR resulted in HTC mitochondrial DNA levels in Huh 7 cells that were 76% (p<0.001) lower than complexes without excess AsOR. In contrast, HTC mitochondrial DNA levels in SK Hep1 cells were barely detectable under any condition, FIG. 10D. Conclusions: The data suggest that not only the AsOR-PL component of complexed mitochondria, but the mitochondria themselves, as determined by HTC donor mitochondrial DNA in the form of complexes were taken up by Huh 7 cells specifically mediated by the AsGR.

Endosomolytic Agents and Cytoplasmic Delivery of Mitochondria in Hepatocytes

AsGR-mediated endocytosis is a degradative pathway. Therefore, mitochondria internalized by Huh 7 cells would be expected to be digested by lysosomal enzymes, FIG. 1. To facilitate endosomal escape of internalized mitochondria into the cytoplasm prior lysosomal digestion, advantage was taken of a bacterial protein, listeriolysin 0 (LLO), which produces pores in endosomal membranes under conditions that exist in endosomes. Such pores result in rupture of endosomes releasing the contents into the cytoplasm, FIG. 11. To target LLO to hepatocyte endosomes, an AsOR-LLO conjugate, AsOR was chemically coupled to LLO using a disulfide linker to allow cleavage under reducing conditions of endosomes, FIG. 12. In the presence of DTT simulating reducing conditions in endosomes, ASOR-LLO was completely cleaved into its constituents. Using hemolysis as a measure of membrane-disruptive activity, LLO alone at pH 5.6 resulted in hemolysis of 32.8% of red blood cells, and this increased significantly ($p<0.001$) to 88.6% in the presence of a reducing agent, DTT, TABLE 2.

To determine whether the AsOR-LLO conjugate could enhance intra-cytoplasmic delivery of mitochondria to hepatocytes, uptake assays of complexed mitochondria were performed using Huh 7 cells and SK Hep1 cells with or without AsOR-LLO conjugates. After incubation with Fl-AsOR-PL-mitochondria complex alone, fluorescence levels in Huh 7 cells were 13,400 units at 15 min, and increased to more than 30,000 units at 120 min, FIG. 14A. However, co-administration of AsOR-LLO conjugate with complexed mitochondria significantly ($p<0.001$) increased fluorescence levels in Huh 7 cells from 13,000 units at 15 min to approximately 50,000 units at 120 min. Pre-incubation of a large molar excess of AsOR resulted in a >90% decrease in fluorescence in Huh 7 cells exposed to complexed mitochondria with and without AsOR-LLO. In contrast, SK Hep1 cells did not have significant levels of fluorescence under any condition or time point, FIG. 14B. Co-administration of AsOR-LLO conjugate with complexed mitochondria also resulted in significantly increased HTC mitochondrial DNA levels in Huh 7 cells from 110-fold (approximately 1-2 HTC mitochondria per cell) at 15 min to approximately 23,800-fold (approximately 140-340 HTC mitochondria per cell) over untreated controls ($p<0.001$) at 120 min FIG. 14C. Incubation of Fl-AsOR-PL-mitochondria complex alone led to significantly increased, but lower HTC mitochondrial DNA levels from 690-fold ($p<0.004$) (approximately 4-10 HTC mitochondria per cell) at 15 min to 7,500-fold (approximately 40-110 HTC mitochondria per cell) over untreated controls at 120 min in Huh 7 cells ($p<0.001$). Incubation with excess AsOR decreased HTC mitochondrial DNA levels by 75% in Huh 7 cells exposed to complexed mitochondria with or without AsOR-LLO. No significant levels of HTC mitochondrial DNA were found in SK Hep1 cells under any condition, FIG. 14D. Huh7 cells at 0° C., FIG. 14E, and in the presence of colchicine, FIG. 14F, did not have significant levels of mitochondrial DNA.

Localization of Internalized Mitochondria

To determine intracellular distribution of complexed mitochondria, a cell line stably expressing GFP-labeled mitochondria, HTC Mito-GFP, was used as the source of mitochondria for uptake experiments. HTC cells stably expressing GFP-labeled mitochondria were sorted with FACS to establish an HTC mito-GFP cell line which was subsequently maintained in 1.5 mg/ml G418 media for selection, FIG. 15. Huh 7 cells were incubated with complexes and controls for 120 min, washed with EDTA-PBS, and maintained in DMEM 10% FBS. Six h later, cells were stained with an early endosomal marker (EEA1-Alexa Fluor 594). Huh 7 cells incubated with GFP-labeled HTC mitochondria alone showed endosomal staining, FIG. 16A1, but no GFP staining, FIG. 16B1. Cells incubated with AsOR-PL-mitochondria complex showed endosomal staining, FIG. 16A2, and some GFP fluorescence, FIG. 16B2. Those GFP-stained structures that were present revealed overlapping (yellow) GFP and Alexa Fluor 594 in the merged view, FIG. 17D2, suggesting co-localization of mitochondria and endosomes. Co-localization of GFP and Alexa Fluor 594 was further supported by fluorescence plot intensities in Z-axis of cell images from random fields, FIG. 18. Cells incubated with both AsOR-PL-mitochondria complex and AsOR-LLO conjugate also showed endosomal, FIG. 16A3, and some GFP, FIG. 16 B3, overlapping Alexa Fluor 594 staining, FIG. 17D3. However, there were also large quantities of non-overlapped GFP surrounding nuclei, FIG. 17D3 in the merged view, suggesting the presence of mitochondria not co-localized with endosomes. A plot of fluorescence intensities of early endosomal marker EEA1 and GFP-mitochondria, showed coincidence of the peak stack number EEA1 and GFP confocal microscopic images of Huh 7 cells, 6 h post incubation with AsOR-PL-mitochondria-GFP complexes at 37° C., FIG. 18. Conclusions: In the absence of AsOR-LLO, mitochondria-associated GFP co-localized with endosomal marker. Co-administration of AsOR-LLO with complexed mitochondria resulted in separation of GFP and endosomal markers, supporting endosomal escape of mitochondria.

Figure 18:
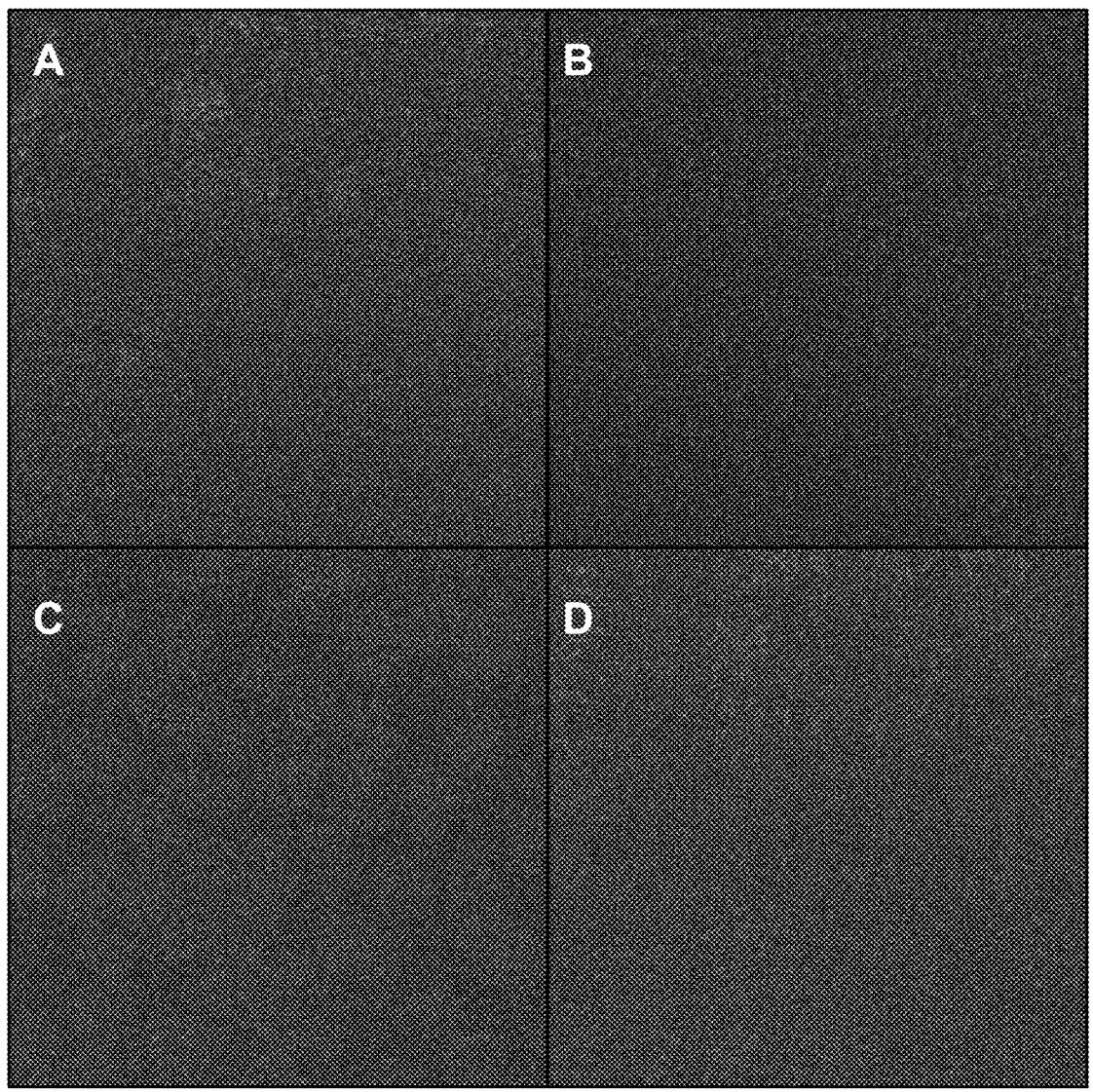
FIG. 18. Other examples mitochondria-GFP alone incubated with Huh7 cells at 37° C. for 2 h, then incubated in media without additives for 6 h. Cells were stained with DAPI for nuclei, and an early endosomal marker, EEA1-Alexa 594.

Another example of mitochondria-GFP alone incubated with Huh7 cells at 37° C. for 2 h, then incubated in media without additives for 6 h is shown in FIG. 18. Cells were stained with DAPI for nuclei, and an early endosomal marker, EEA1-Alexa 594. FIG. 18A showed endosomal, but no GFP staining, FIG. 18B. FIG. 18C, shows DAPI nuclei, and FIG. 18D merged views.

Figure 19:
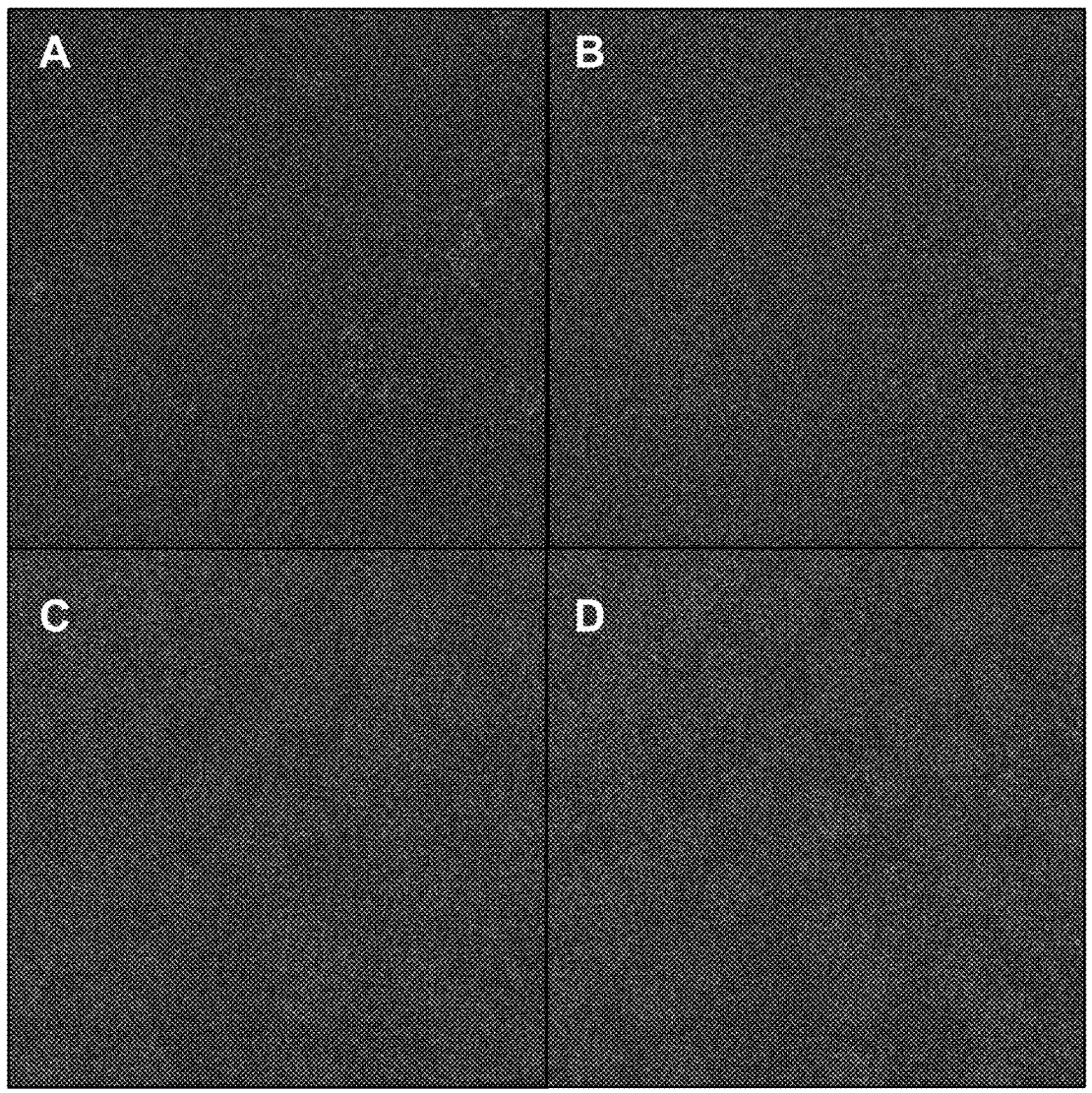
FIG. 19. Other examples AsOR-PL-mitochondria-GFP incubated with Huh7 cells at 37° C. for 2 h, then incubated in media without mitochondria for 6 h. Huh 7 cells were changed to media without mitochondria for 6 h, and then stained for early-endosome marker EEA1. Cells were imaged under a confocal fluorescence microscope 6 hr later.

Another example of AsOR-PL-mitochondria-GFP incubated with Huh7 cells at 37° C. for 2 h, then incubated in media without additives for 6 h is shown in FIG. 19. Endosomal staining was seen, FIG. 19A, (anti-EEA1-Alexa Fluor 594), and some GFP staining, FIG. 19B. However, the merged view, FIG. 18D showed that the GFP staining seen in FIG. 19B, merged with EEA1-Alexa Fluor 594, FIG. 19D.

Figure 20:
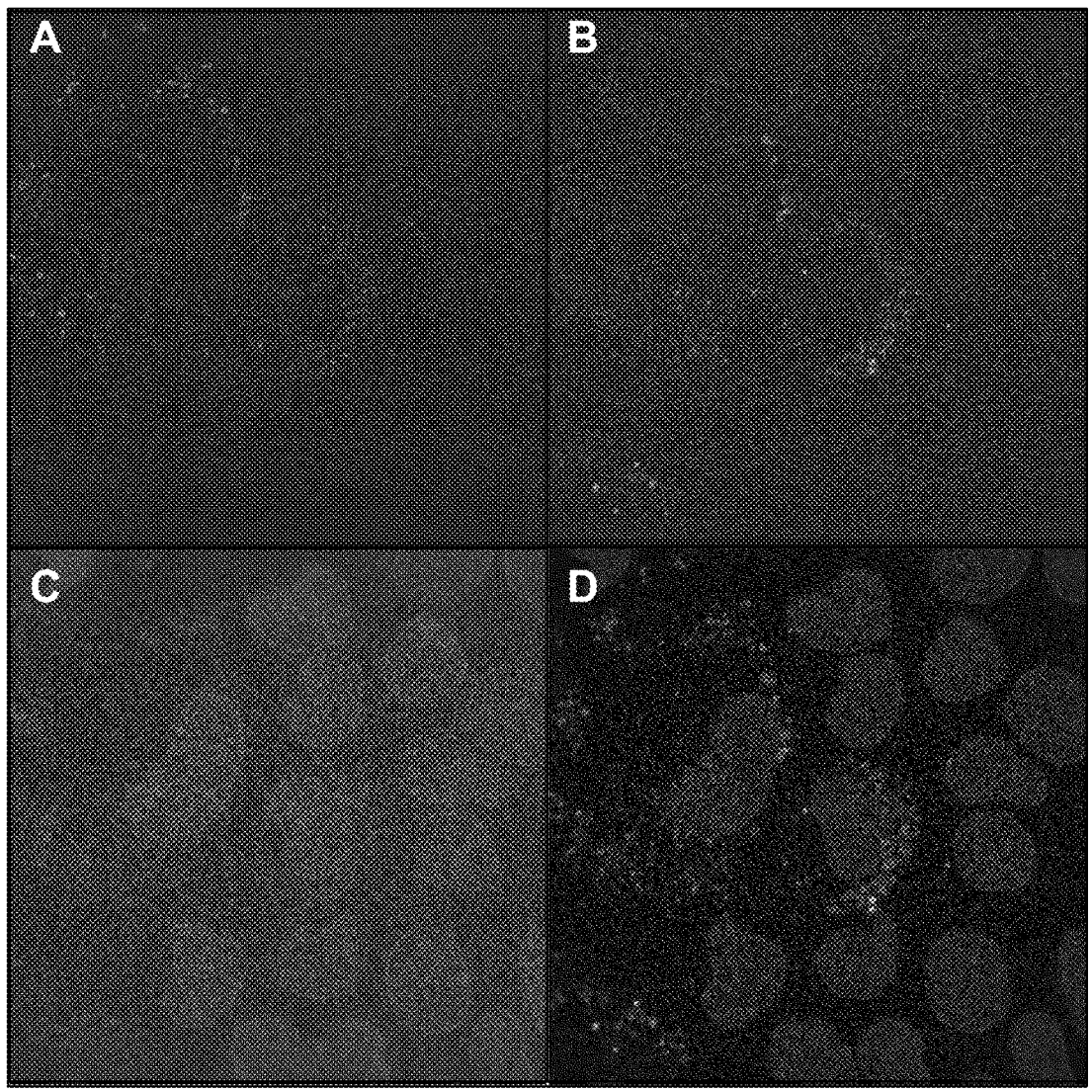
FIG. 20. Other examples AsOR-PL-mitochondria-GFP and ASOR-LLO incubated with Huh7 cells at 37° C. for 2 h, then incubated in media without additives for 6 h FIG. 20A, DAPI nuclei.

Another example of AsOR-PL-mitochondria-GFP and ASOR-LLO incubated with Huh7 cells at 37° C. for 2 h, then incubated in media without additives for 6 h is shown in FIG. 20. There was endosomal staining, FIG. 20A, and considerable GFP staining, FIG. 20B. However, the majority of the GFP staining did not merge with the EEA1-Alexa Fluor 594, FIG. 20D merged.

Changes in AsG-Associated Fluorescence and Mitochondrial DNA Levels after Exposure of Complexed Mitochondria to Mito (−) Cells Huh 7-Mito (−) and SK Hep1-Mito (−) cells lacking mitochondrial DNA were created by incubation of cells with ddC. Mitochondrial DNA declined and became undetectable by PCR by 9 d, FIG. 22. These cells required supplemental medium containing compensatory nutrients to survive.

Administration of complexed Huh7-derived mitochondria alone to Huh 7-Mito (−) cells resulted in fluorescence levels that significantly ($p<0.01$) increased from 6,400 units at 60 min to more than 11,000 units at 120 min. After co-administration of complexed mitochondria with AsOR-LLO conjugate, fluorescence levels in Huh 7-Mito (−) cells significantly ($p<0.001$) increased from 14,000 units at 60 min to more than 30,000 units at 120 min. These fluorescence levels decreased by >90% after incubation with excess AsOR, FIG. 23A. However, fluorescence levels were not stable in Huh 7-Mito (−) cells, and continued to decrease from 7,000 units at 12 h to 300 units by 7 d. Co-administration of complexed mitochondria and AsOR-LLO conjugate resulted in fluorescence levels that decreased from 27,000 units at 12 h to 11,000 units at 10 d, FIG. 23B. Excess AsOR resulted in no significant levels of fluorescence in Huh 7-Mito (−) cells after exposure to complexed mitochondria with or without AsOR-LLO conjugate. There was no significant fluorescence in SK Hep1-Mito (−) cells under any condition, FIG. 23C and FIG. 23D. Conclusions: Co-administration of AsOR-LLO with complexed mitochondria increased uptake as measured by both protein label and mitochondrial DNA.

Figure 23A:
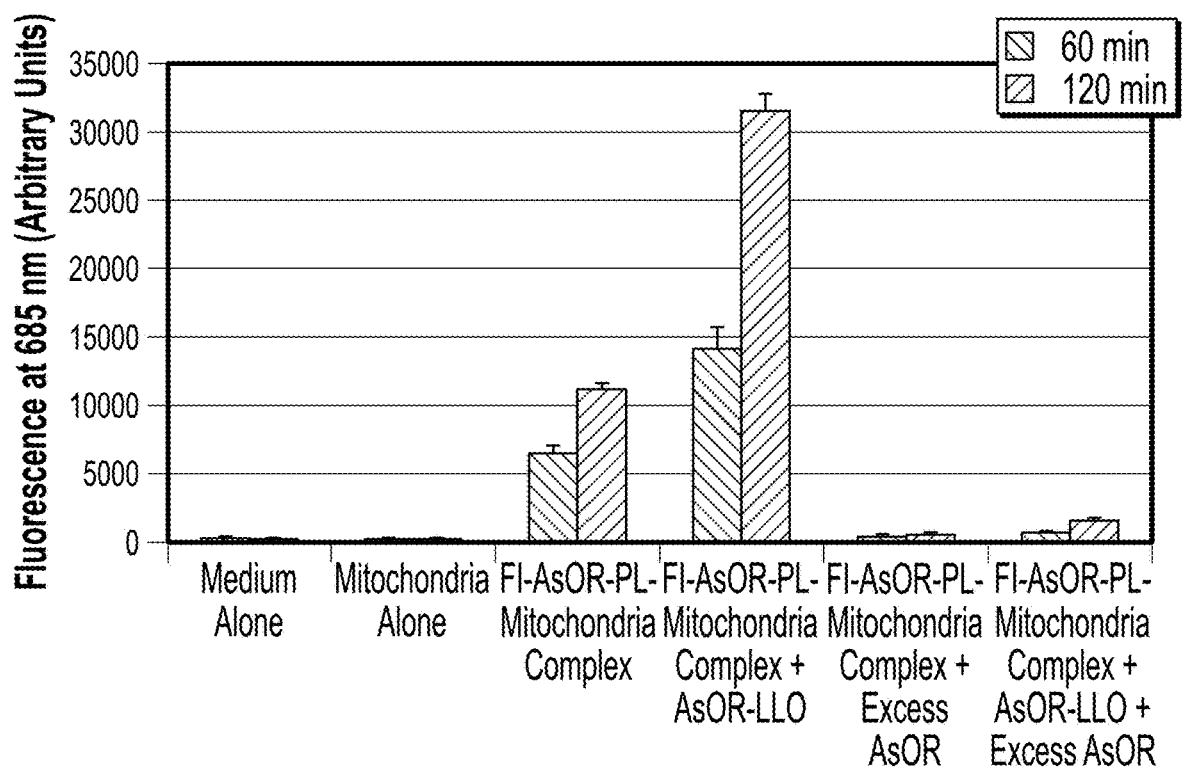
FIG. 23A, fluorescence levels in Huh 7-Mito (−) cells at 120 min.
Figure 23B:
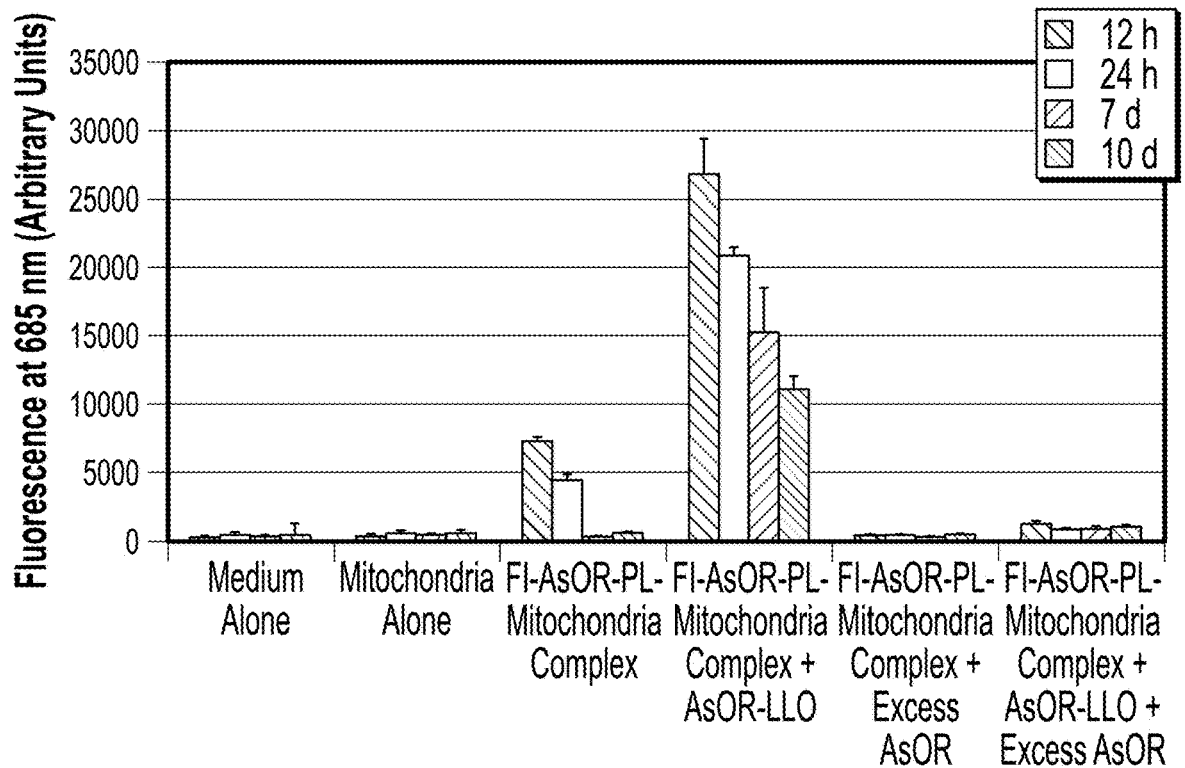
Figure 23C:
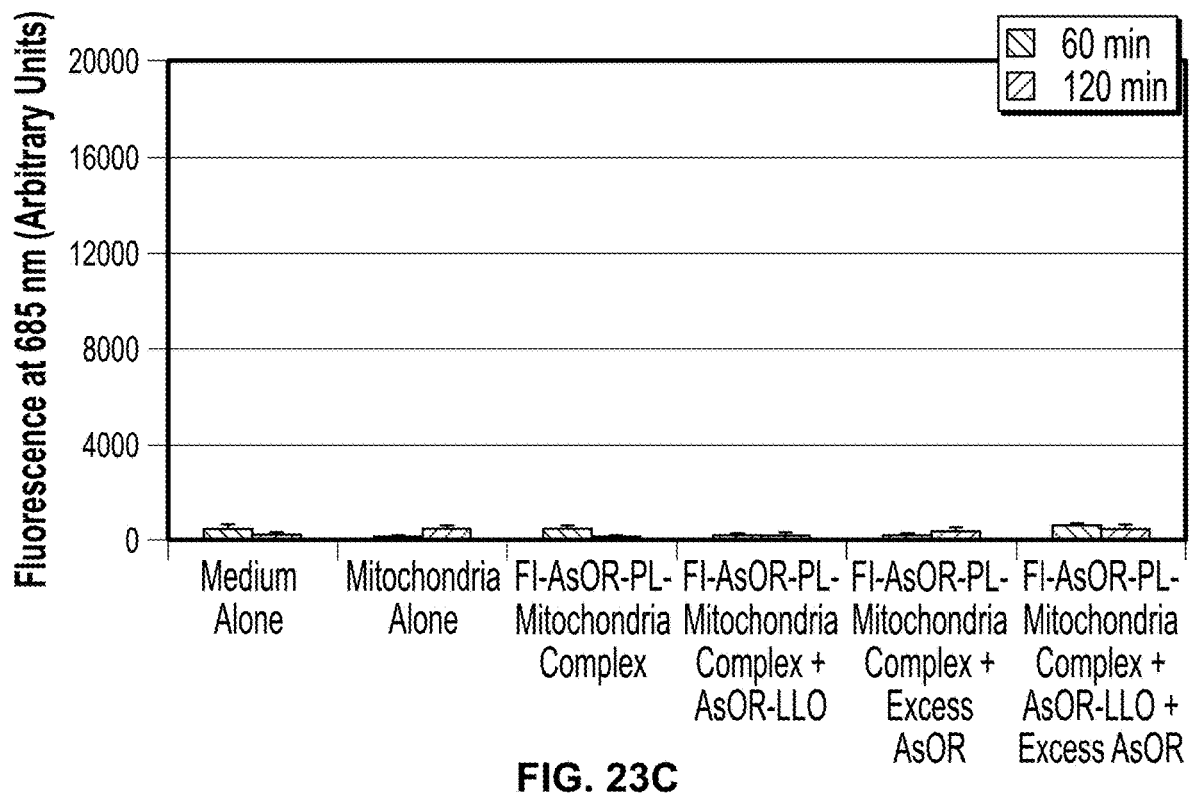
FIG. 23C, SK Hep1-Mito (−) cells at 120 min.
Figure 23D:
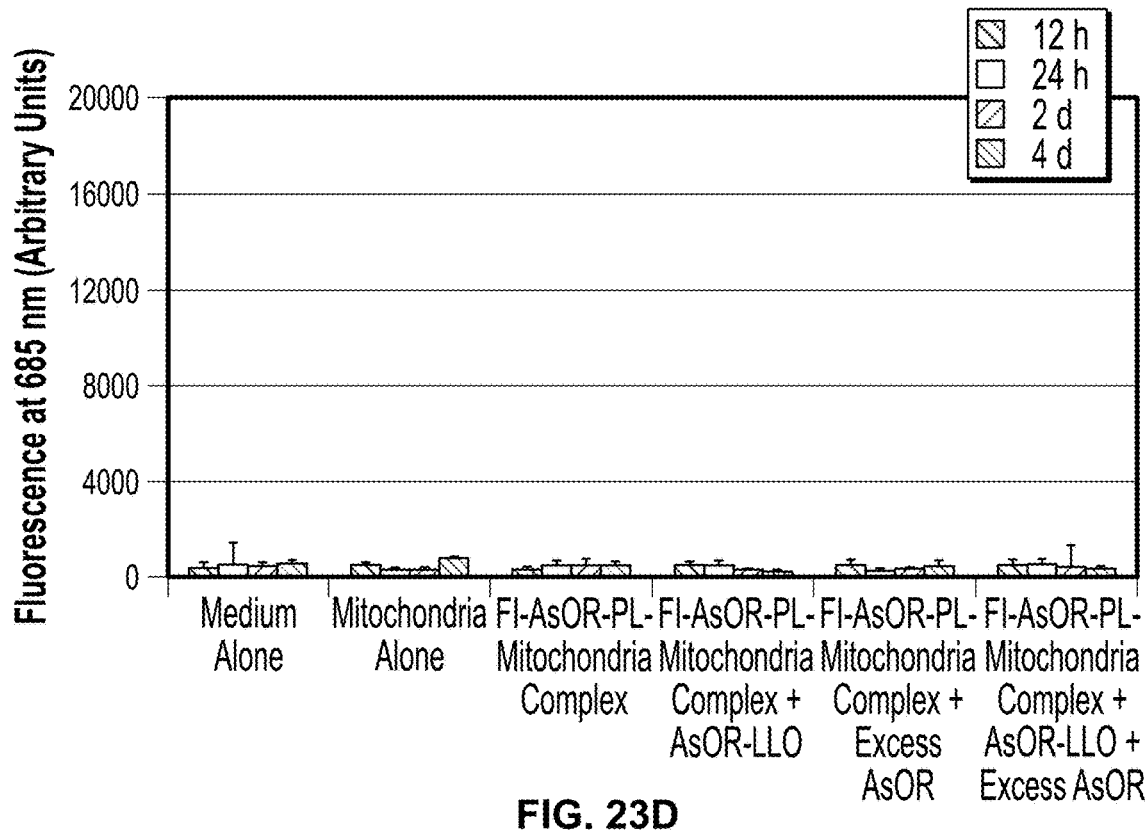
Figure 23E:
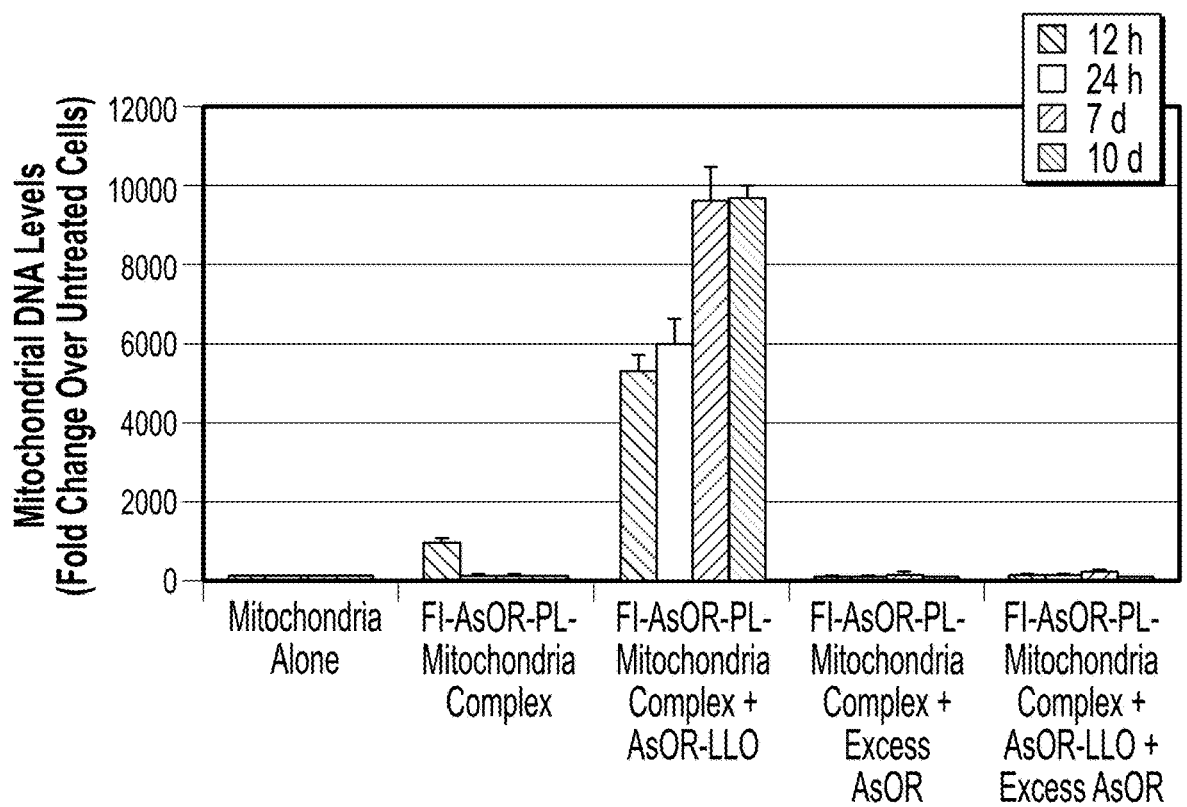
Figure 23F:
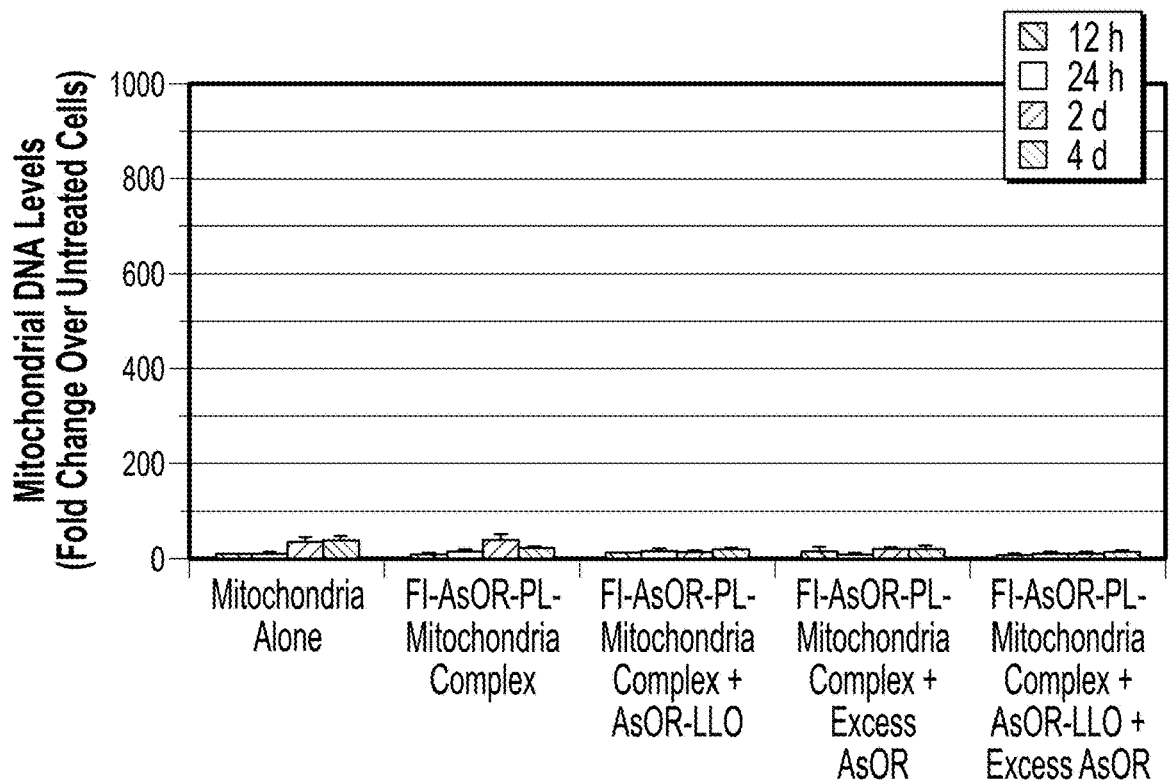
FIG. 23F, SK Hep1-Mito (−) cells at 4 d. Bars correspond to mean±S.E. of arbitrary fluorescence units per equal number of cells.

Changes in AsG-Associated Fluorescence and DNA Levels after Exposure of Complexed Mitochondria to Mito (−) Cells To determine whether mitochondrial DNA levels declined in a manner similar to the fluorescence, Huh 7 mitochondrial DNA levels were assayed by qPCR. In contrast to the fluorescence data, complexed mitochondria co-administered with AsOR-LLO conjugate to Huh 7-Mito (−) cells resulted in a significant ($p<0.001$) increase in mitochondrial DNA levels from 5,300-fold (30-70 mitochondria per cell) over control at 12 h to more than 9,700-fold (60-140 mitochondria per cell) ($p<0.001$) over control at 7 d, and remained stable up to 10 d in supplement-free media. Exposure to complexed mitochondria in the absence of AsOR-LLO conjugate resulted in mitochondrial DNA levels 900-fold over (5-10 mitochondria per cell) control at 12 h, and barely detectable levels at 24 h, FIG. 23E. Mitochondrial DNA levels in SK Hep1-Mito (−) cells were barely detectable under any condition. FIG. 23F. Conclusions: The protein marker decreased while mitochondrial DNA levels increased after co-administration of complexed mitochondria and AsOR-LLO conjugate indicates that intracellular fates of protein carrier and internalized mitochondria were different, probably due separation of the two components some time within 8 h after internalization.

Cell Proliferation of Mito (−) Cells Exposed to Complexed Mitochondria

Figure 24:
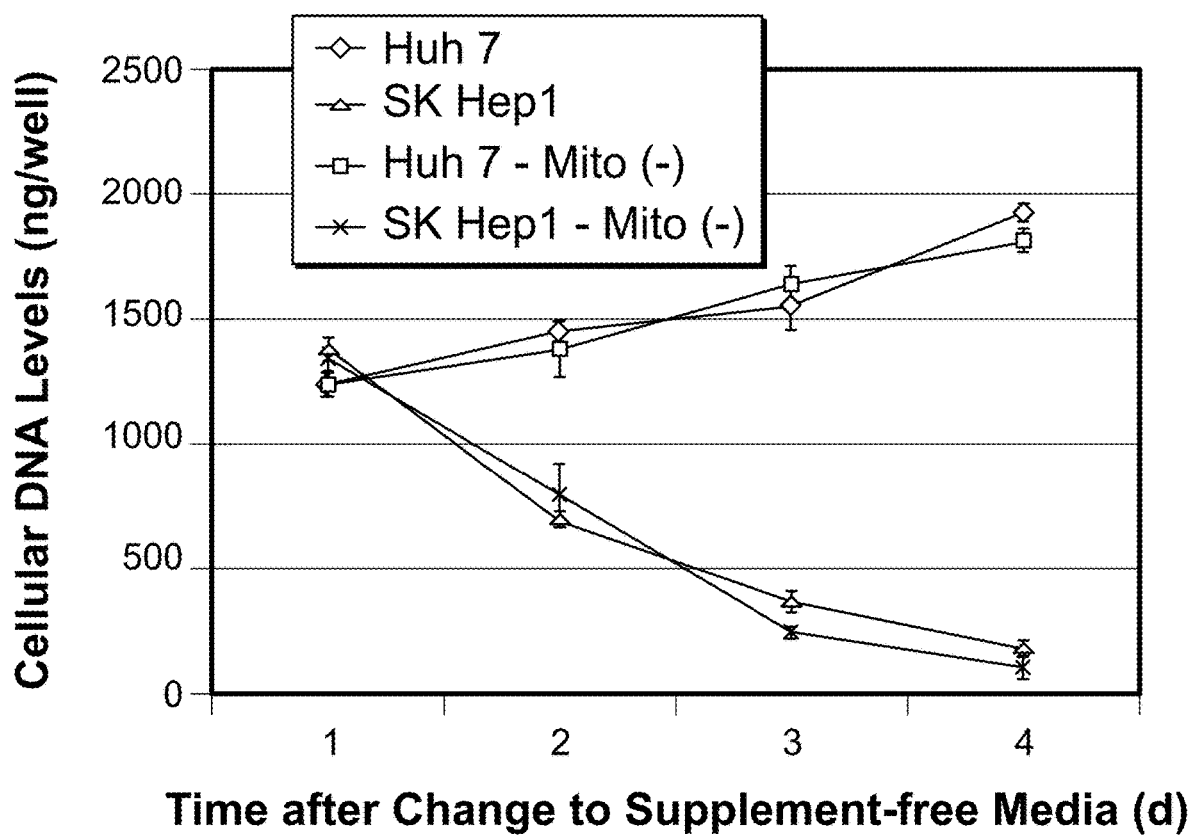
FIG. 24. Cellular DNA levels in cells after change to supplement-free media. Mito (−) cells were grown in supplemental media, and then changed to supplement-free media. DNA levels were measured by qPCR as a function of time.

To determine whether uptake of mitochondria by Mito (−) cells affected cell proliferation in supplement-free media, cell numbers were assayed by cellular DNA as a function of time after exposure to complexed mitochondria. Removal of supplemental media from Mito (−) cells resulted in an 85% decrease in mitochondrial DNA for both Huh 7-Mito (−), and SK Hep1 (−Mito (−). Mito (+) cells grew normally, FIG. 24. Co-administration of complexed mitochondria and AsOR-LLO conjugate resulted in a significant increase in cell DNA to 3.5-fold ($p<0.001$) over baseline by 10 d, FIG. 25A. In contrast, in untreated cells, DNA decreased to 0.03-fold over baseline ($p<0.004$). SK Hep1-Mito (−) cell numbers decreased under all conditions, FIG. 25B. The data suggested that co-administration of complexed mitochondria and AsOR-LLO conjugate to Huh 7-Mito (−) cells increased cell numbers in supplement-free media. Rescued Huh 7-Mito (−) cells proliferated and were passaged in supplement-free media for at least 8 weeks (data not shown).

Aerobic Respiration of Mito (−) Cells Exposed to Complexed Mitochondria

Figure 26A:
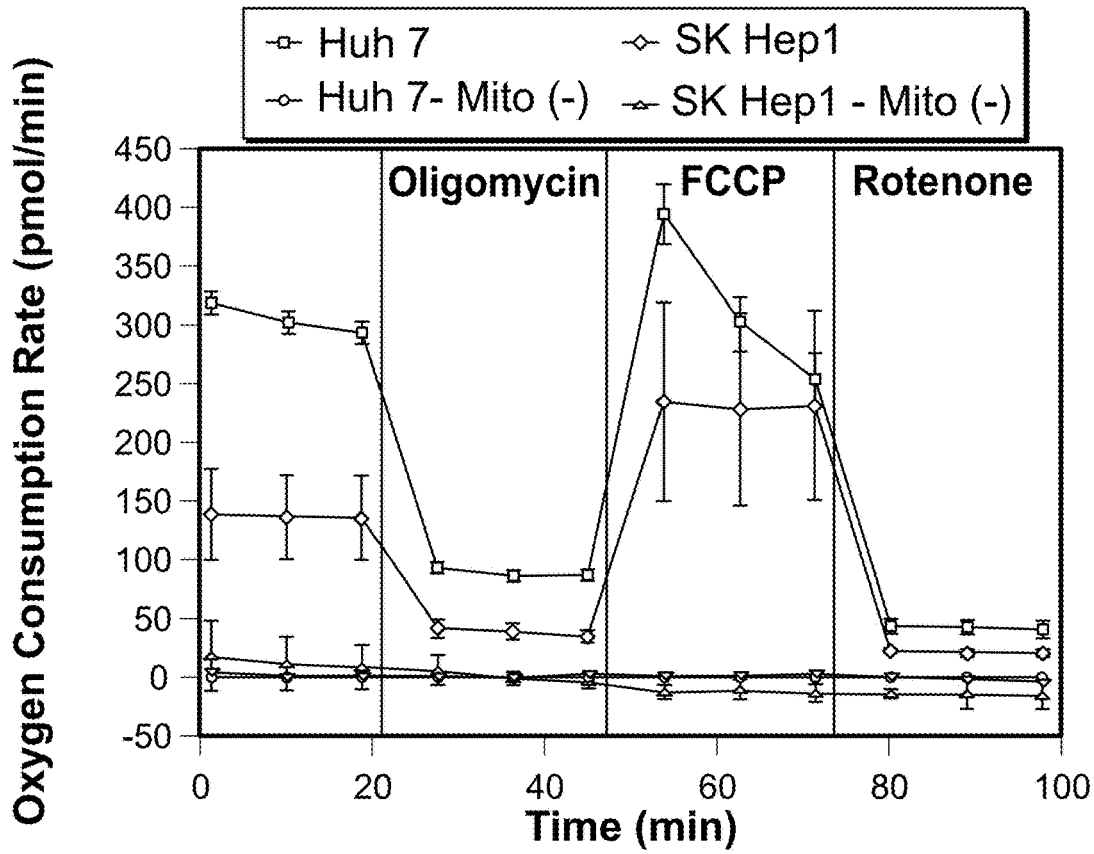
Figure 26B:
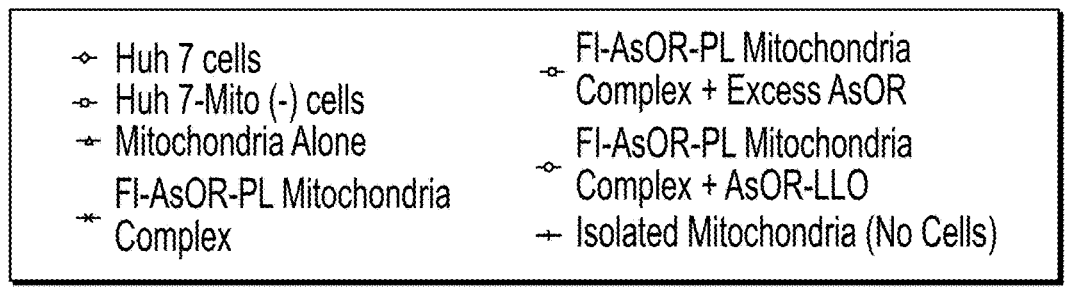
Figure 26B:
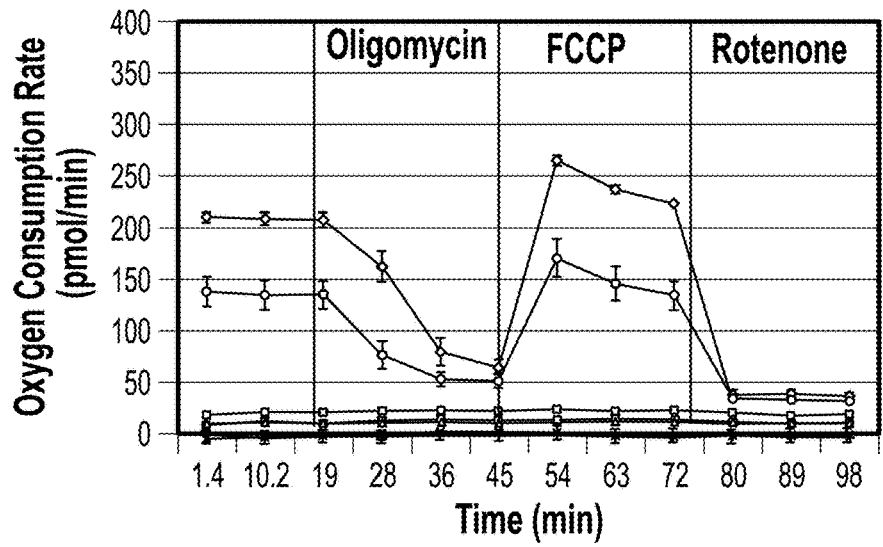
Figure 26C:
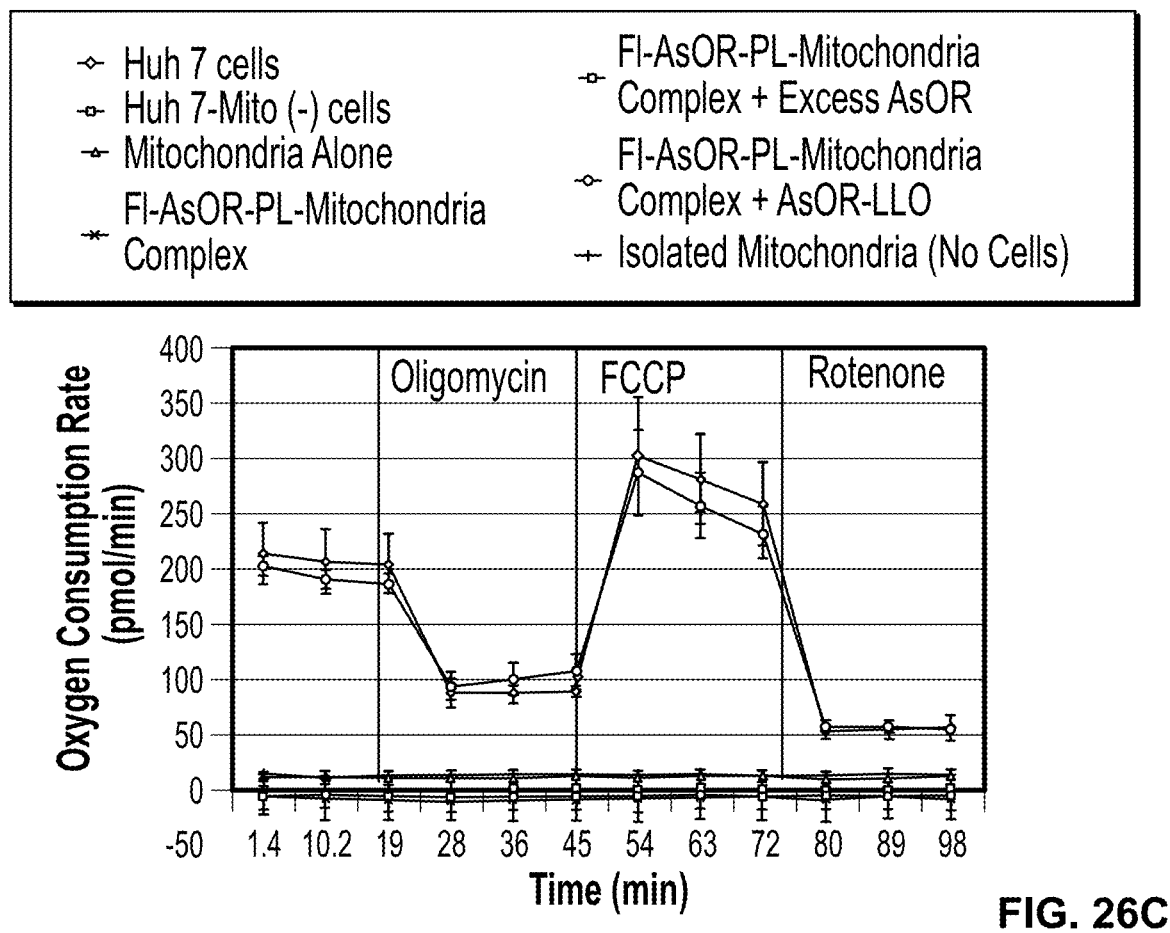

If transplanted mitochondria were functional, they should affect oxygen consumption of recipient cells. Therefore, the oxygen consumption rate (OCR) was measured to quantitate mitochondrial respiration levels in cells. While Huh 7-Mito (−) and SK Hep1-Mito (−) cells showed no measurable mitochondrial respiration, Huh 7 and SK Hep1 cells showed high basal OCR which changed with the addition of oligomycin, carbonyl cyanide-p-trifluoromethoxyphenyl-hydrazon (FCCP) and rotenone, consistent with mitochondrial respiration, FIG. 26A. Twelve h after co-administration of complexed mitochondria and AsOR-LLO conjugate to Huh 7-Mito (−) cells, there was an increase in OCR to 70% compared to parental Mito (+) cells. This increase was blocked by a large molar excess of AsOR, FIG. 26B. Ten d after co-administration of complexed mitochondria and AsOR-LLO conjugate, Huh 7-Mito (−) cells had levels of mitochondrial respiration/cell comparable to (>90%) that of the parental Huh 7 cells, FIG. 26C.

Discussion

This example shows that mitochondria can be targeted for uptake by a specific cell type, and that co-internalization of an endosomolytic protein can result in intracellular release of functional mitochondria. That the observed internalization of mitochondria was not simply due to phagocytosis is indicated by the fact that exposure of AsGR (+) cells to isolated mitochondria alone, and exposure of complexed mitochondria to AsGR (−) cells both failed to result in internalization under identical conditions. The data on targeted transplantation of mitochondria into AsGR (+) Mito (−) cells showed that those cells were not only able to survive in supplement-free media, but were able to proliferate. The amount of mitochondrial DNA per cell also increased.

Exposure of mitochondria to LLO conjugate at low pH did not cause significant mitochondrial membrane damage in the absence of reducing conditions. The combination of reducing conditions and low pH did result in some mitochondrial membrane damage in the test tube suggesting that upon release, LLO can damage mitochondrial membranes in a concentration-dependent manner. However, the fact that co-internalization of complexed mitochondria and LLO conjugate resulted in internalized mitochondria with normal oxygen consumption, suggests that if damage to targeted mitochondria had occurred, the effects were not sufficient to prevent those mitochondria from meeting the energy requirements of the host cells.

Besides minimizing background host mitochondrial DNA, the use of ddC served as a model for actual drug-induced mitochondrial toxicity. ddC is an agent that had been originally approved by the FDA and used clinically until substantial side effects due to mitochondrial damage were observed, greatly limiting its use currently. A limitation of the model is that the extent of mitochondrial damage in the current studies exceeds that which is typically observed in clinical drug reactions. However, the fact that targeted mitochondrial transplantation was able to rescue cells with no detectable preexisting mitochondrial DNA suggests that targeted mitochondrial transplantation in cells with less extreme toxicity might result in at least similar rescue from the effects of drug-induced mitochondrial toxicity.

The co-internalization of complexed mitochondria and targeted endosomolytic agents by hepatocytes in culture can result in internalization of functional mitochondria capable of rescuing cells whose mitochondria are damaged by drug toxicity. Such a transplantation system might be useful in the study of the regulation of mitochondrial proliferation, and function in normal and pathological states.

Other Embodiments

The foregoing description discloses only exemplary embodiments of the invention.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the appended claims. Thus, while only certain features of the invention have been illustrated and described, many modifications and changes will occur to those skilled in the art. It is therefore to be understood that the appended claims are intended to cover all such modifications and changes as fall within the true spirit of the invention.

What is claimed is:

1. A pharmaceutical composition comprising:
   an asialoglycoprotein (AsG) covalently attached to a polycation; and
   functional mammalian mitochondria that are at least partially purified;
   wherein the AsG, covalently attached to the polycation, is complexed electrostatically to the mitochondria.

2. The composition of claim 1, wherein the AsG comprises asialoorosomucoid (AsOR).

3. The composition of claim 1, wherein the polycation is highly positively charged and is selected from the group of polycations consisting of polylysine (PL), polyarginine, and polyornithine.

4. The composition of claim 3, wherein the polycation is polylysine (PL).

5. The composition of claim 1, further comprising an endosomolytic agent.

6. The composition of claim 5, wherein the endosomolytic agent is listeriolysin.

7. The composition of claim 5, wherein the endosomolytic agent is covalently attached to the AsG by a bond cleavable under conditions that exist in an endosome.

8. The composition of claim 7, wherein the bond cleavable under conditions that exist in an endosome is an acid-labile bond.

9. The composition of claim 8, wherein the acid-labile bond is an imino-, acetal, or lactone bond.

10. The compositions of claim 1, wherein the mitochondria are obtained from a cell from a healthy donor or isolated from a mammalian cell or tissue.

11. The composition of claim 10, wherein the mitochondria are isolated from a mammalian cell, and wherein the mammalian cell is a hepatocyte, white blood cell, stem cell or tissue.

12. The composition of claim 1, wherein the mitochondria are human or rat mitochondria.

13. A kit comprising a pharmaceutical composition that comprises an asialoglycoprotein (AsG) covalently attached to a polycation; functional mammalian mitochondria, at least partially purified; and instruction for using said composition to treat a liver disease.

14. The kit of claim 13, wherein said composition further comprises an endosomolytic agent covalently attached to a separate AsG by a cleavable bond.

15. A method of making a composition comprising:
   at least partially purifying functional mitochondria from a cell;
   allowing an AsG to be covalently attached to a polycation, wherein the polycation is highly positively charged and is selected from the group of polycations consisting of polylysine (PL), polyarginine, and polyornithine; and
   allowing the AsG, covalently attached to the polycation, to complex electrostatically to the mitochondria.

16. The method of claim 15, wherein the polycation is polylysine (PL).

17. The method of claim 15, wherein the AsG comprises asialoorosomucoid (AsOR).

18. The method of claim 15, further comprising allowing an endosomolytic agent to be covalently attached to the AsG by a bond cleavable by conditions within endosomes.

19. The method of claim 18, wherein the endosomolytic agent is listeriolysin.

20. A method of transplanting mitochondria into a hepatocyte, comprising providing a composition comprising functional mammalian mitochondria complexed with AsG-PL electrostatically, and an endosomolytic agent that is covalently attached to a separate AsG by a cleavable bond; and delivering said composition to a hepatocyte.

21. The methods of claim 20, wherein the AsG in the AsG-PL comprises asialoorosomucoid (AsOR).

22. The method of claim 20, wherein the endosomolytic agent is listeriolysin.

* * * * *